United States Patent
Germeroth

(10) Patent No.: US 12,331,318 B2
(45) Date of Patent: Jun. 17, 2025

(54) NON-IMMUNOGENIC ENGINEERED TISSUE AND METHODS OF PRODUCING AND USING THE SAME

(71) Applicant: Lothar Germeroth, Goettingen (DE)

(72) Inventor: Lothar Germeroth, Goettingen (DE)

( * ) Notice: Subject to any disclaimer, the term of this patent is extended or adjusted under 35 U.S.C. 154(b) by 383 days.

(21) Appl. No.: 17/259,900

(22) PCT Filed: Jul. 15, 2019

(86) PCT No.: PCT/EP2019/068944
§ 371 (c)(1),
(2) Date: Jan. 12, 2021

(87) PCT Pub. No.: WO2020/012033
PCT Pub. Date: Jan. 16, 2020

(65) Prior Publication Data
US 2021/0284965 A1    Sep. 16, 2021

(30) Foreign Application Priority Data
Jul. 13, 2018 (EP) .................................... 18183294

(51) Int. Cl.
*C12N 5/077* (2010.01)

(52) U.S. Cl.
CPC ........ *C12N 5/0657* (2013.01); *C12N 2500/90* (2013.01); *C12N 2510/00* (2013.01)

(58) Field of Classification Search
None
See application file for complete search history.

(56) References Cited

U.S. PATENT DOCUMENTS

| | | |
|---|---|---|
| 2008/0219956 A1 | 9/2008 | Russell et al. |
| 2018/0094245 A1 | 4/2018 | Kamp et al. |
| 2021/0363487 A1* | 11/2021 | Kamp ................. C12N 5/0606 |

FOREIGN PATENT DOCUMENTS

| | | |
|---|---|---|
| WO | 9209688 A1 | 6/1992 |
| WO | 2007054286 A1 | 5/2007 |
| WO | 2012/145384 A1 | 10/2012 |
| WO | 2013047639 A1 | 4/2013 |
| WO | 2013/158292 A1 | 10/2013 |
| WO | 2015025030 A1 | 2/2015 |
| WO | 2015040142 A1 | 3/2015 |

OTHER PUBLICATIONS

Hoare et al. Subtle changes in peptide conformation profoundly affect recognition of the non-classical MHC class I molecule HLA-E by the CD94-NKG2 natural killer cell receptors. J Mol Biol. Apr. 11, 2008;377(5):1297-303. doi: 10.1016/j.jmb.2008.01.098. Epub Feb. 12, 2008. PMID: 18339401. (Year: 2008).*

Kim K, et al. Epigenetic memory in induced pluripotent stem cells. Nature. Sep. 16, 2010;467(7313):285-90. doi: 10.1038/nature09342. PMID: 20644535; PMCID: PMC3150836. (Year: 2010).*

International Search Report issued in PCT/EP2019/068944 on Sep. 10, 2019 (5 pages).

Written Opinion of the ISA issued in PCT/EP2019/068944 on Sep. 10, 2019 (6 pages).

Written Opinion of the IPEA issued in PCT/EP2019/068944 on Oct. 20, 2020 (21 pages).

Karabekian et al., "HLA Class I Depleted hESC as a Source of Hypoimmunogenic Cells for Tissue Engineering Applications", Tissue Engineering: Part A, vol. 21, Nos. 19 and 20, 2015, DOI: 10.1089/ten.tea.2015.0105.

Lu et al., "Generating Hypoimmunogenic Human Embryonic Stem Cells by the Disruption of Beta 2-Microglobulin", Stem Cell Reviews and Reports, 9, 806-813 (2013) (Abstract only).

Baghbaderani et al., cGMP-Manufactured Human Induced Pluripotent Stem Cells Are Available for Pre-clinical and Clinical Applications. Stem Cell Reports. Oct. 13, 2015;5(4):647-659.

Chou et al., Efficient human iPS cell derivation by a non-integrating plasmid from blood cells with unique epigenetic and gene expression signatures. Cell Res. Mar. 2011;21(3):518-529.

Didié et al., Parthenogenetic stem cells for tissue-engineered heart repair. J Clin Invest. Mar. 2013;123(3):1285-1298.

Ewart et al., Application of Microphysiological Systems to Enhance Safety Assessment in Drug Discovery. Annu Rev Pharmacol Toxicol. Jan. 6, 2018;58:65-82.

Gornalusse et al., HLA-E-expressing pluripotent stem cells escape allogeneic responses and lysis by NK cells. Nat Biotechnol. Aug. 2017;35(8):765-772.

Khan et al., AAV-mediated gene targeting methods for human cells. Nat Protoc. Apr. 2011;6(4):482-501.

Lancaster and Knoblich, Organogenesis in a dish: Modeling development and disease using organoid technologies. Science. Jul. 18, 2014;345(6194):1247125.

Lancaster et al., Cerebral organoids model human brain development and microcephaly. Nature. Sep. 19, 2013;501(7467):373-379.

Llonch et al., Organoid technology for retinal repair. Dev Biol. Jan. 15, 2018;433(2):132-143.

(Continued)

Primary Examiner — Allison M Fox
Assistant Examiner — Alyssa G Weston
(74) Attorney, Agent, or Firm — Michael A. Whittaker

(57) ABSTRACT

The invention provides a method of producing a non-immunogenic (bio)engineered tissue from pluripotent stem cells or pluripotent stem cell derivatives, the respective cells being deficient of MHC class I molecules and comprising an immunomodulatory protein on their surface, wherein the method comprises inducing the differentiation of the pluripotent stem cells into a cell type that is essential for the function of the engineered tissue under conditions that also allow the formation of the engineered tissue, thereby rendering the engineered tissue to be non-immunogenic to a recipient of the engineered tissue. The present invention further relates to an engineered tissue, a pharmaceutical composition comprising the engineered tissue, medical treatments using the engineered tissue and uses of the engineered tissue.

13 Claims, 21 Drawing Sheets

Specification includes a Sequence Listing.

(56) References Cited

OTHER PUBLICATIONS

Lu et al., A defined xeno-free and feeder-free culture system for the derivation, expansion and direct differentiation of transgene-free patient-specific induced pluripotent stem cells. Biomaterials. Mar. 2014,35(9):2816-2826.

Morizane et al., Concise Review: Kidney Generation with Human Pluripotent Stem Cells. Stem Cells. Nov. 2017;35(11):2209-2217.

Ogle et al., Distilling complexity to advance cardiac tissue engineering. Sci Transl Med. Jun. 8, 2016;8(342):342ps13.

Okita et al., A more efficient method to generate integration-free human iPS cells. Nat Methods. May 2011;8(5):409-412.

Ott et al., Perfusion-decellularized matrix: using nature's platform to engineer a bioartificial heart. Nat Med. Feb. 2008;14(2):213-221.

Pagliuca et al.,Generation of Functional Human Pancreatic B Cells In Vitro. Cell. Oct. 9, 2014;159(2):428-439.

Rao et al, Engineering human pluripotent stem cells into functional skeletal muscle tissue. Nat Commun. Jan. 9, 2018;9(1):126 (12 pages).

Sawa et al., Safety and Efficacy of Autologous Skeletal Myoblast Sheets (TCD-51073) for the Treatment of Severe Chronic Heart Failure Due to Ischemic Heart Disease. Circ J. 2015;79(5):991-999.

Shimizu et al., Fabrication of Pulsatile Cardiac Tissue Grafts Using a Novel 3-Dimensional Cell Sheet Manipulation Technique and Temperature Responsive Cell Culture Surfaces. Circ Res. Feb. 22, 2002;90(3):e40-e48.

Song et al., Vascular Tissue Engineering: Progress, Challenges, and Clinical Promise. Cell Stem Cell. Mar. 1, 2018;22(3):340-354.

Soong et al., Cardiac differentiation of human embryonic stem cells and their assembly into engineered heart muscle. Curr Protoc Cell Biol. Jun. 2012;Chapter 23:Unit 23.8.

Sudo, Multiscale tissue engineering for liver reconstruction. Organogenesis. Apr.-Jun. 2014;10(2):216-224.

Takahashi and Yamanaka, Induction of Pluripotent Stem Cells from Mouse Embryonic and Adult Fibroblast Cultures by Defined Factors. Cell. Aug. 25, 2006;126(4):663-676.

Thomson et al., Embryonic Stem Cell Lines Derived from Human Blastocysts. Science. Nov. 6, 1998;282(5391):1145-1147.

Tiburcy et al., Collagen-based engineered heart muscle. Methods Mol Biol. 2014;1181:167-176.

Tiburcy et al., Defined Engineered Human Myocardium With Advanced Maturation for Applications in Heart Failure Modeling and Repair. Circulation. May 9, 2017;135(19):1832-1847.

Yang et al., Induced Neuronal Cells: How to Make and Define a Neuron. Cell Stem Cell. Dec. 2, 2011;9(6):517-525.

Ye et al., Patching the Heart: cardiac repair from within and outside. Circ Res. Sep. 13, 2013;113(7):922-932.

Zimmermann, Remuscularizing failing hearts with tissue engineered myocardium. Antioxid Redox Signal. Aug. 2009;11(8):2011-2023.

Zimmermann et al., Engineered heart tissue grafts improve systolic and diastolic function in infarcted rat hearts. Nat Med. Apr. 2006;12(4):452-458.

Cellosaurus, retrieved from https://www.cellosaurus.org/CVCL_RH36 on Oct. 11, 2023 (3 pages).

NIH News Release, Manufactured stem cells to advance clinical research, retrieved from https://www.nih.gov/news-events/manufactured-stem-cells-advance-clinical-research on Oct. 11, 2023 (4 pages).

Baghbaderani et al., "cGMP-Manufactured Human Induced Pluripotent Stem Cells Are Available for Pre-clinical and Clinical Applications", Stem Cell Reports. Oct. 13, 2015;5(4):647-59. doi: 10.1016/j.stemcr.2015.08.015. Epub Sep. 24, 2015.

Kim et al., "Epigenetic memory in induced pluripotent stem cells", Nature. Sep. 16, 2010;467(7313):285-90. doi: 10.1038/nature09342.

"Safety and Efficacy of Induced Pluripotent Stem Cell-derived Engineered Human Myocardium as Biological Ventricular Assist Tissue in Terminal Heart Failure (BioVAT-HF)"; ClinicalTrials.gov ID NCT04396899; Sponsor University Medical Center Goettingen Information provided by Karsten Gavenis, University Medical Center Goettingen (Responsible Party); Last Update Posted Mar. 27, 2023.

Polo et a., "Cell type of origin influences the molecular and functional properties of mouse induced pluripotent stem cells", Nat Biotechnol. Aug. 2010;28(8):848-55. doi: 10.1038/nbt.1667. Epub Jul. 19, 2010.

Poetsch et al., "Human Induced Pluripotent Stem Cells: From Cell Origin, Genomic Stability, and Epigenetic Memory to Translational Medicine", Stem Cells. Jun. 22, 2022;40(6):546-555. doi: 10.1093/stmcls/sxac020.

Raab et al., "A Comparative View on Human Somatic Cell Sources for iPSC Generation", Stem Cells Int. 2014:2014:768391. doi: 10.1155/2014/768391. Epub Nov. 6, 2014.

Office Action issued by the CIPO in related Canadian patent application No. 3105897 dated Jan. 29, 2025 (4 pages).

* cited by examiner

Figure 1 human B2M WT: Exon 1

```
  1 CGCACCCCAG ATCGGAGGGC GCCGATGTAC AGACAGCAAA CTCACCCAGT
 51 CTAGTGCATG CCTTCTTAAA CATCACGAGA CTCTAAGAAA AGGAAACTGA
101 AAACGGGAAA GTCCCTCTCT CTAACCTGGC ACTGCGTCGC TGGCTTGGAG
151 ACAGGTGACG GTCCCTGCGG GCCTTGTCCT GATTGGCTGG GCACGCGTTT
201 AATATAAGTG GAGGCGTCGC GCTGGCGGGC ATTCCTGAAG CTGACAGCAT
251 TCGGGCCGAG ATGTCTCGCT CCG*TGGCCT*T AGCTGTGCTC GCGCTACTCT
301 CTCTTTCTGG *CCT*GGAGGCT ATCCAGCGTG AGTCTCTCCT ACCCTCCCGC
351 TCTGGTCCTT CCTCTCCCGC TCTGCACCCT CTGTGGCCCT CGCTGTGCTC
401 TCTCGCTCCG TGACTTCCCT TCTCCAAGTT CTCCTTGGTG GCCCGCCGTG
451 GGGCTAGTCC AGGGCTGGAT CTCGGGGAAG CGGCGGGGTG GCCTGGGAGT
501 GGGGAAGGGG GTGCGCACCC GGGACGCGCG CTACTTGCCC CTTTCGGCGG
```
(SEQ ID NO: 8)

B2M_CR1 (71/rev): GAGTAGCGCGAGCACAGCTA*AGG* antisense (SEQ ID NO: 6)

B2M_CR2 (37/rev): ACTCACGCTGGATAGCCTCC*AGG* antisense (SEQ ID NO: 5)

B2M_CR3 (34/fw): GGCCGAGATGTCTCGCTCCG*TGG* sense (SEQ ID NO: 7)

Figure 2

B2M-#003 > 1bp insertion, hetero

```
201 AATATAAGTG GAGGCGTCGC GCTGGCGGGC ATTCCTGAAG CTGACAGCAT
251 TCGGGCCGAG ATGTCTCGCT CCGTGGCCTT AGCTGTGCTC GCGCTACTCT
301 CTCTTTCTGG CCTGGACGGCT ATCCAGCGTG AGTCTCTCCT ACCCTCCCGC
```
(SEQ ID NO: 9)

```
201 AATATAAGTG GAGGCGTCGC GCTGGCGGGC ATTCCTGAAG CTGACAGCAT
251 TCGGGCCGAG ATGTCTCGCT CCGTGGCCTT AGCTGTGCTC GCGCTACTCT
301 CTCTTTCTGG CCTGGAGGCT ATCCAGCGTG AGTCTCTCCT ACCCTCCCGC
```
(SEQ ID NO: 10)

B2M-#018 > 13bp deletion, 1bp deletion, compound hetero

```
201 AATATAAGTG GAGGCGTCGC GCTGGCGGGC ATTCCTGAAG CTGACAGCAT
251 TCGGGCCGAG ATGTCTCGCT CCGTGGCCTT AGCTGTGCTC GCGCTACTCT
301 CTCTTTCTGG CCTGG---------------TG AGTCTCTCCT ACCCTCCCGC
```
(SEQ ID NO: 11)

```
201 AATATAAGTG GAGGCGTCGC GCTGGCGGGC ATTCCTGAAG CTGACAGCAT
251 TCGGGCCGAG ATGTCTCGCT CCGTGGCCTT AGCTGTGCTC GCGCTACTCT
301 CTCTTTCTGG CCTGGA-GCT ATCCAGCGTG AGTCTCTCCT ACCCTCCCGC
```
(SEQ ID NO: 12)

B2M-#020 > 1bp deletion, homo

```
201 AATATAAGTG GAGGCGTCGC GCTGGCGGGC ATTCCTGAAG CTGACAGCAT
251 TCGGGCCGAG ATGTCTCGCT CCGTGGCCTT AGCTGTGCTC GCGCTACTCT
301 CTCTTTCTGG CCTGGA-GCT ATCCAGCGTG AGTCTCTCCT ACCCTCCCGC
```
(SEQ ID NO: 13)

```
201 AATATAAGTG GAGGCGTCGC GCTGGCGGGC ATTCCTGAAG CTGACAGCAT
251 TCGGGCCGAG ATGTCTCGCT CCGTGGCCTT AGCTGTGCTC GCGCTACTCT
301 CTCTTTCTGG CCTGGA-GCT ATCCAGCGTG AGTCTCTCCT ACCCTCCCGC
```
(SEQ ID NO: 14)

B2M-#034 > 2bp insertion, homo

```
201 AATATAAGTG GAGGCGTCGC GCTGGCGGGC ATTCCTGAAG CTGACAGCAT
251 TCGGGCCGAG ATGTCTCGCT CCGTGGCCTT AGCTCTGTGCTC GCGCTACTCT
301 CTCTTTCTGG CCTGGAGGCT ATCCAGCGTG AGTCTCTCCT ACCCTCCCGC
```
(SEQ ID NO: 15)

```
201 AATATAAGTG GAGGCGTCGC GCTGGCGGGC ATTCCTGAAG CTGACAGCAT
251 TCGGGCCGAG ATGTCTCGCT CCGTGGCCTT AGCTCTGTGCTC GCGCTACTCT
301 CTCTTTCTGG CCTGGAGGCT ATCCAGCGTG AGTCTCTCCT ACCCTCCCGC
```
(SEQ ID NO: 16)

Figure 4

Dimer sequence (SEQ ID NO: 17):

ACAGCAAACTCACCCAGTCTAGTGCATGCCTTCTTAAACATCACGAGACTCTAAGAAAAGGAAACTGAAAAC
GGGAAAGTCCCTCTCTCTAACCTGGCACTGCGTCGCTGGCTTGGAGACAGGTGACGGTCCCTGCGGGCCTTG
TCCTGATTGGCTGGGCACGCGTTTAATATAAGTGGAGGCGTCGCGCTGGCGGGCATTCCTGAAGCTGACAGC
ATTCGGGCCGAGATGTCTCGCTCCGTGGCCTTAGCTGTGCTCGCGCTACTCTCTCTTTCTGGCCTGGGAAGC
GGAGAGGGCAGAGGAAGTCTTCTAACATGCGGTGACGTGGAGGAGAATCCCGGCCCAATGTCACGATCTGTT
GCGCTGGCCGTGTTGGCTCTTCTGTCCCTGAGCGGCCTCGAGGCTATCCAGCGTACGCCAAAGATTCAGGTT
TACTCACGTCATCCAGCAGAGAATGGAAAGTCAAATTTCCTGAATTGCTATGTGTCTGGGTTTCATCCATCC
GACATTGAAGTTGACTTACTGAAGAATGGAGAGAGAATTGAAAAAGTGGAGCATTCAGACTTGTCTTTCAGC
AAGGACTGGTCTTTCTATCTCTTGTACTACACTGAATTCACCCCCACTGAAAAAGATGAGTATGCCTGCCGT
GTGAACCATGTGACTTTGTCACAGCCCAAGATAGTTAAGTGGGATCGCGACATGGGTGGTGGCGGTTCTGGT
GGTGGCGGTAGTGGCGGCGGAGGAAGCGGTGGTGGCGGTTCCGGATCTCACTCCTTGAAGTATTTCCACACT
TCCGTGTCCCGGCCCGGCCGCGGGGAGCCCCGCTTCATCTCTGTGGGCTACGTGGACGACACCCAGTTCGTG
CGCTTCGACAACGACGCCGCGAGTCCGAGGATGGTGCCGCGGGCGCCGTGGATGGAGCAGGAGGGGTCAGAG
TATTGGGACCGGGAGACACGGAGCGCCAGGGACACCGCACAGATTTTCCGAGTGAACCTGCGGACGCTGCGC
GGCTACTACAATCAGAGCGAGGCCGGGTCTCACACCCTGCAGTGGATGCATGGCTGCGAGCTGGGGCCCGAC
AGGCGCTTCCTCCGCGGGTATGAACAGTTCGCCTACGACGGCAAGGATTATCTCACCCTGAATGAGGACCTG
CGCTCCTGGACCGCGGTGGACACGGCGGCTCAGATCTCCGAGCAAAAGTCAAATGATGCCTCTGAGGCGGAG
CACCAGAGAGCCTACCTGGAAGACACATGCGTGGAGTGGCTCCACAAATACCTGGAGAAGGGGAAGGAGACG
CTGCTTCACCTGGAGCCCCCAAAGACACACGTGACTCACCACCCCATCTCTGACCATGAGGCCACCCTGAGG
TGCTGGGCTCTGGGCTTCTACCCTGCGGAGATCACACTGACCTGGCAGCAGGATGGGGAGGCCATACCCAG
GACACGGAGCTCGTGGAGACCAGGCCTGCAGGGGATGGAACCTTCCAGAAGTGGGCAGCTGTGGTGGTGCCT
TCTGGAGAGGAGCAGAGATACACGTGCCATGTGCAGCATGAGGGGCTACCCGAGCCCGTCACCCTGAGATGG
AAGCCGGCTTCCCAGCCCACCATCCCCATCGTGGGCATCATTGCTGGCCTGGTTCTCCTTGGATCTGTGGTC
TCTGGAGCTGTGGTTGCTGCTGTGATATGGAGGAAGAAGAGCTCAGGTGGAAAAGGAGGGAGCTACTATAAG
GCTGAGTGGAGCGACAGTGCCCAGGGGTCTGAGTCTCACAGCTTGTAAGCCTCGACTGTGCCTTCTAGTTGC
CAGCCATCTGTTGTTTGCCCCTCCCCGTGCCTTCCTTGACCCTGGAAGGTGCCACTCCCACTGTCCTTTCC
TAATAAAATGAGGAAATTGCATCGCATTGTCTGAGTAGGTGTCATTCTATTCTGGGGGGTGGGGTGGGGCAG
GACAGCAAGGGGGAGGATTGGGAAGACAATAGCAGGCATGCTGGGGATAAGGCTATCCAGCGTGAGTCTCTC
CTACCCTCCCGCTCTGGTCCTTCCTCTCCCGCTCTGCACCCTCTGTGGCCCTCGCTGTGCTCTCTCGCTCCG
TGACTTCCCTTCTCCAAGTTCTCCTTGGTGGCCCGCCGTGGGGCTAGTCCAGGGCTGGATCTCGGGGAAGCG
GCGGGGTGGCCTGGGAGTGGGGAAGGGGTGCGCACCCGGGACGCGCGCTACTTGCCCCTTTCGGCGGGGAG
CAGGGGAGACCTTTGGCCTACGGCGACGGGAGGGTCGGGACAAAGTTTAGGGCGTCGATAAGCGTCAGAGCG
CCGAGGTTGGGGGAGGGTTTCTCTTCCGCTCTTT

Figure 4 (continued)

Trimer sequence (SEQ ID NO: 19):

ACAGCAAACTCACCCAGTCTAGTGCATGCCTTCTTAAACATCACGAGACTCTAAGAAAAGGAAACTGAAAAC
GGGAAAGTCCCTCTCTCTAACCTGGCACTGCGTCGCTGGCTTGGAGACAGGTGACGGTCCCTGCGGGCCTTG
TCCTGATTGGCTGGGCACGCGTTTAATATAAGTGGAGGCGTCGCGCTGGCGGGCATTCCTGAAGCTGACAGC
ATTCGGGCCGAGATGTCTCGCTCCGTGGCCTTAGCTGTGCTCGCGCTACTCTCTCTTTCTGGCCTGGGAAGC
GGAGAGGGCAGAGGAAGTCTTCTAACATGCGGTGACGTGGAGGAGAATCCCGGCCCAATGTCACGATCTGTT
GCGCTGGCCGTGTTGGCTCTTCTGTCCCTGAGCGGCCTCGAGGCTGTTATGGCTCCGCGGACTTTAATTTTA
GGTGGTGGCGGATCCGGTGGTGGCGGTTCTGGTGGTGGCGGCTCCATCCAGCGTACGCCAAAGATTCAGGTT
TACTCACGTCATCCAGCAGAGAATGGAAAGTCAAATTTCCTGAATTGCTATGTGTCTGGGTTTCATCCATCC
GACATTGAAGTTGACTTACTGAAGAATGGAGAGAGAATTGAAAAAGTGGAGCATTCAGACTTGTCTTTCAGC
AAGGACTGGTCTTTCTATCTCTTGTACTACACTGAATTCACCCCCACTGAAAAAGATGAGTATGCCTGCCGT
GTGAACCATGTGACTTTGTCACAGCCCAAGATAGTTAAGTGGGATCGCGACATGGGTGGTGGCGGTTCTGGT
GGTGGCGGTAGTGGCGGCGGAGGAAGCGGTGGTGGCGGTTCCGGATCTCACTCCTTGAAGTATTTCCACACT
TCCGTGTCCCGGCCCGGCCGCGGGGAGCCCCGCTTCATCTCTGTGGGCTACGTGGACGACACCCAGTTCGTG
CGCTTCGACAACGACGCCGCGAGTCCGAGGATGGTGCCGCGGGCGCCGTGGATGGAGCAGGAGGGGTCAGAG
TATTGGGACCGGGAGACACGGAGCGCCAGGGACACCGCACAGATTTTCCGAGTGAACCTGCGGACGCTGCGC
GGCTACTACAATCAGAGCGAGGCCGGGTCTCACACCCTGCAGTGGATGCATGGCTGCGAGCTGGGGCCCGAC
AGGCGCTTCCTCCGCGGGTATGAACAGTTCGCCTACGACGGCAAGGATTATCTCACCCTGAATGAGGACCTG
CGCTCCTGGACCGCGGTGGACACGGCGGCTCAGATCTCCGAGCAAAAGTCAAATGATGCCTCTGAGGCGGAG
CACCAGAGAGCCTACCTGGAAGACACATGCGTGGAGTGGCTCCACAAATACCTGGAGAAGGGGAAGGAGACG
CTGCTTCACCTGGAGCCCCCAAAGACACACGTGACTCACCACCCCATCTCTGACCATGAGGCCACCCTGAGG
TGCTGGGCTCTGGGCTTCTACCCTGCGGAGATCACACTGACCTGGCAGCAGGATGGGGAGGGCCATACCCAG
GACACGGAGCTCGTGGAGACCAGGCCTGCAGGGATGGAACCTTCCAGAAGTGGGCAGCTGTGGTGGTGCCT
TCTGGAGAGGAGCAGAGATACACGTGCCATGTGCAGCATGAGGGGCTACCCGAGCCCGTCACCCTGAGATGG
AAGCCGGCTTCCCAGCCCACCATCCCCATCGTGGGCATCATTGCTGGCCTGGTTCTCCTTGGATCTGTGGTC
TCTGGAGCTGTGGTTGCTGCTGTGATATGGAGGAAGAAGAGCTCAGGTGGAAAAGGAGGGAGCTACTATAAG
GCTGAGTGGAGCGACAGTGCCCAGGGGTCTGAGTCTCACAGCTTGTAAGCCTCGACTGTGCCTTCTAGTTGC
CAGCCATCTGTTGTTTGCCCCTCCCCGTGCCTTCCTTGACCCTGGAAGGTGCCACTCCCACTGTCCTTTCC
TAATAAAATGAGGAAATTGCATCGCATTGTCTGAGTAGGTGTCATTCTATTCTGGGGGGTGGGTGGGGCAG
GACAGCAAGGGGGAGGATTGGGAAGACAATAGCAGGCATGCTGGGGATAAGGCTATCCAGCGTGAGTCTCTC
CTACCCTCCCGCTCTGGTCCTTCCTCTCCCGCTCTGCACCCTCTGTGGCCCTCGCTGTGCTCTCTCGCTCCG
TGACTTCCCTTCTCCAAGTTCTCCTTGGTGGCCCGCCGTGGGCTAGTCCAGGGCTGGATCTCGGGGAAGCG
GCGGGGTGGCCTGGGAGTGGGAAGGGGGTGCGCACCCGGGACGCGCGCTACTTGCCCCTTTCGGCGGGGAG
CAGGGGAGACCTTTGGCCTACGGCGACGGGAGGGTCGGGACAAAGTTTAGGGCGTCGATAAGCGTCAGAGCG
CCGAGGTTGGGGGAGGGTTTCTCTTCCGCTCTTT

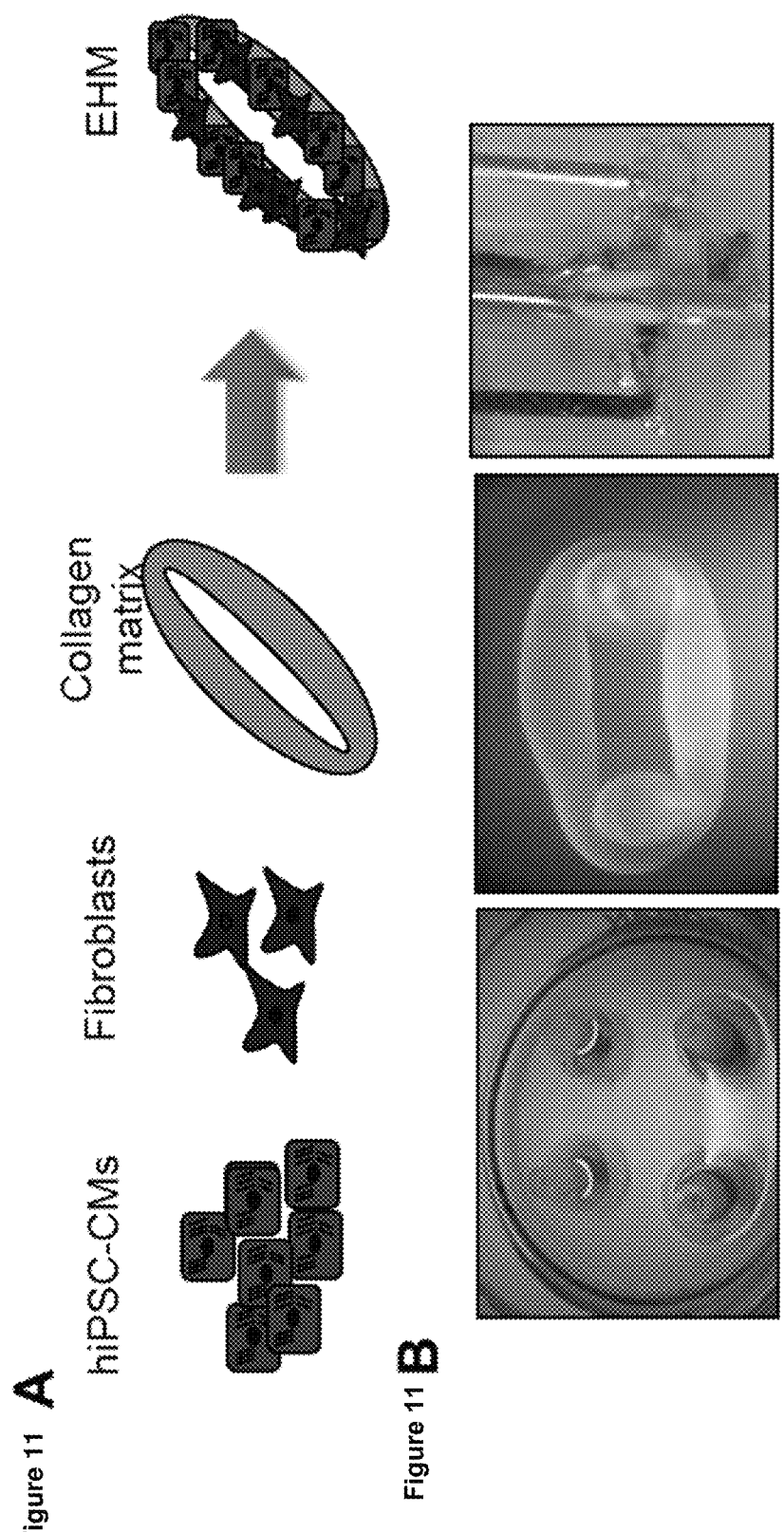

SEQUENCE LISTING

```
<160> NUMBER OF SEQ ID NOS: 30

<210> SEQ ID NO 1
<211> LENGTH: 9
<212> TYPE: PRT
<213> ORGANISM: Artificial
<220> FEATURE:
<223> OTHER INFORMATION: Peptide antigen

<400> SEQUENCE: 1

Val Met Ala Pro Arg Thr Leu Phe Leu
1               5
```

```
<210> SEQ ID NO 2
<211> LENGTH: 20
<212> TYPE: DNA
<213> ORGANISM: Artificial
<220> FEATURE:
<223> OTHER INFORMATION: BM2 crRNA #1

<400> SEQUENCE: 2
actcacgctg gatagcctcc                                              20

<210> SEQ ID NO 3
<211> LENGTH: 20
<212> TYPE: DNA
<213> ORGANISM: Artificial
<220> FEATURE:
<223> OTHER INFORMATION: B2M crRNA # 2

<400> SEQUENCE: 3
gagtagcgcg agcacagcta                                              20

<210> SEQ ID NO 4
<211> LENGTH: 20
<212> TYPE: DNA
<213> ORGANISM: Artificial
<220> FEATURE:
<223> OTHER INFORMATION: B2M crRNA #3

<400> SEQUENCE: 4
ggccgagatg tctcgctccg                                              20

<210> SEQ ID NO 5
<211> LENGTH: 23
<212> TYPE: DNA
<213> ORGANISM: Artificial
<220> FEATURE:
<223> OTHER INFORMATION: B2M crRNA # 1 + PAM

<400> SEQUENCE: 5
actcacgctg gatagcctcc agg                                          23

<210> SEQ ID NO 6
<211> LENGTH: 23
<212> TYPE: DNA
<213> ORGANISM: Artificial
<220> FEATURE:
<223> OTHER INFORMATION: B2M crRNA #2 + PAM

<400> SEQUENCE: 6
gagtagcgcg agcacagcta agg                                          23

<210> SEQ ID NO 7
<211> LENGTH: 23
<212> TYPE: DNA
<213> ORGANISM: Artificial
<220> FEATURE:
<223> OTHER INFORMATION: B2M crRNA #3 + PAM

<400> SEQUENCE: 7
ggccgagatg tctcgctccg tgg                                          23

<210> SEQ ID NO 8
<211> LENGTH: 550
<212> TYPE: DNA
<213> ORGANISM: Homo sapiens

<400> SEQUENCE: 8
```

```
cgcaccccag atcggagggc gccgatgtac agacagcaaa ctcacccagt ctagtgcatg      60
ccttcttaaa catcacgaga ctctaagaaa aggaaactga aaacgggaaa gtccctctct     120
ctaacctggc actgcgtcgc tggcttggag acaggtgacg gtccctgcgg gccttgtcct     180
gattggctgg gcacgcgttt aatataagtg gaggcgtcgc gctggcgggc attcctgaag     240
ctgacagcat tcgggccgag atgtctcgct ccgtggcctt agctgtgctc gcgctactct     300
ctctttctgg cctggaggct atccagcgtg agtctctcct accctcccgc tctggtcctt     360
cctctcccgc tctgcaccct ctgtggccct cgctgtgctc tctcgctccg tgacttccct     420
tctccaagtt ctccttggtg gcccgccgtg gggctagtcc agggctggat ctcggggaag     480
cggcggggtg gcctgggagt ggggaagggg gtgcgcaccc gggacgcgcg ctacttgccc     540
ctttcggcgg                                                            550
```

```
<210> SEQ ID NO 9
<211> LENGTH: 151
<212> TYPE: DNA
<213> ORGANISM: Artificial
<220> FEATURE:
<223> OTHER INFORMATION: First allelle of clone 3

<400> SEQUENCE: 9
aatataagtg gaggcgtcgc gctggcgggc attcctgaag ctgacagcat tcgggccgag      60
atgtctcgct ccgtggcctt agctgtgctc gcgctactct ctctttctgg cctggacggc     120
tatccagcgt gagtctctcc taccctcccg c                                    151
```

```
<210> SEQ ID NO 10
<211> LENGTH: 150
<212> TYPE: DNA
<213> ORGANISM: Artificial
<220> FEATURE:
<223> OTHER INFORMATION: 2nd allele of clone 3

<400> SEQUENCE: 10
aatataagtg gaggcgtcgc gctggcgggc attcctgaag ctgacagcat tcgggccgag      60
atgtctcgct ccgtggcctt agctgtgctc gcgctactct ctctttctgg cctggaggct     120
atccagcgtg agtctctcct accctcccgc                                      150
```

```
<210> SEQ ID NO 11
<211> LENGTH: 137
<212> TYPE: DNA
<213> ORGANISM: Artificial
<220> FEATURE:
<223> OTHER INFORMATION: 1st allele of clone 18

<400> SEQUENCE: 11
aatataagtg gaggcgtcgc gctggcgggc attcctgaag ctgacagcat tcgggccgag      60
atgtctcgct ccgtggcctt agctgtgctc gcgctactct ctctttctgg cctggtgagt     120
ctctcctacc ctcccgc                                                    137
```

```
<210> SEQ ID NO 12
<211> LENGTH: 149
<212> TYPE: DNA
<213> ORGANISM: Artificial
<220> FEATURE:
<223> OTHER INFORMATION: 2nd allele of clone 18

<400> SEQUENCE: 12
aatataagtg gaggcgtcgc gctggcgggc attcctgaag ctgacagcat tcgggccgag      60
```

```
atgtctcgct ccgtggcctt agctgtgctc gcgctactct ctctttctgg cctggagcta    120
tccagcgtga gtctctccta ccctcccgc                                      149
```

<210> SEQ ID NO 13
<211> LENGTH: 149
<212> TYPE: DNA
<213> ORGANISM: Artificial
<220> FEATURE:
<223> OTHER INFORMATION: 1st allele of clone 20

<400> SEQUENCE: 13

```
aatataagtg gaggcgtcgc gctggcgggc attcctgaag ctgacagcat tcgggccgag     60
atgtctcgct ccgtggcctt agctgtgctc gcgctactct ctctttctgg cctggagcta    120
tccagcgtga gtctctccta ccctcccgc                                      149
```

<210> SEQ ID NO 14
<211> LENGTH: 149
<212> TYPE: DNA
<213> ORGANISM: Artificial
<220> FEATURE:
<223> OTHER INFORMATION: 2nd allele of clone 20

<400> SEQUENCE: 14

```
aatataagtg gaggcgtcgc gctggcgggc attcctgaag ctgacagcat tcgggccgag     60
atgtctcgct ccgtggcctt agctgtgctc gcgctactct ctctttctgg cctggagcta    120
tccagcgtga gtctctccta ccctcccgc                                      149
```

<210> SEQ ID NO 15
<211> LENGTH: 152
<212> TYPE: DNA
<213> ORGANISM: Artificial
<220> FEATURE:
<223> OTHER INFORMATION: 1st allele of clone 34

<400> SEQUENCE: 15

```
aatataagtg gaggcgtcgc gctggcgggc attcctgaag ctgacagcat tcgggccgag     60
atgtctcgct ccgtggcctt agctctgtgc tcgcgctact ctctctttct ggcctggagg    120
ctatccagcg tgagtctctc ctaccctccc gc                                  152
```

<210> SEQ ID NO 16
<211> LENGTH: 152
<212> TYPE: DNA
<213> ORGANISM: Artificial
<220> FEATURE:
<223> OTHER INFORMATION: 2nd allele of clone 34

<400> SEQUENCE: 16

```
aatataagtg gaggcgtcgc gctggcgggc attcctgaag ctgacagcat tcgggccgag     60
atgtctcgct ccgtggcctt agctctgtgc tcgcgctact ctctctttct ggcctggagg    120
ctatccagcg tgagtctctc ctaccctccc gc                                  152
```

<210> SEQ ID NO 17
<211> LENGTH: 2338
<212> TYPE: DNA
<213> ORGANISM: Artificial
<220> FEATURE:
<223> OTHER INFORMATION: HLA-E Dimer sequence

<400> SEQUENCE: 17

```
acagcaaact cacccagtct agtgcatgcc ttcttaaaca tcacgagact ctaagaaaag      60
gaaactgaaa acgggaaagt ccctctctct aacctggcac tgcgtcgctg gcttggagac     120
aggtgacggt ccctgcgggc cttgtcctga ttggctgggc acgcgtttaa tataagtgga     180
ggcgtcgcgc tggcgggcat tcctgaagct gacagcattc gggccgagat gtctcgctcc     240
gtggccttag ctgtgctcgc gctactctct ctttctggcc tgggaagcgg agagggcaga     300
ggaagtcttc taacatgcgg tgacgtggag gagaatcccg cccaatgtc acgatctgtt      360
gcgctggccg tgttggctct tctgtccctg agcggcctcg aggctatcca gcgtacgcca     420
aagattcagg tttactcacg tcatccagca gagaatggaa agtcaaattt cctgaattgc     480
tatgtgtctg ggtttcatcc atccgacatt gaagttgact tactgaagaa tggagagaga     540
attgaaaaag tggagcattc agacttgtct ttcagcaagg actggtcttt ctatctcttg     600
tactacactg aattcacccc cactgaaaaa gatgagtatg cctgccgtgt gaaccatgtg     660
actttgtcac agcccaagat agttaagtgg atcgcgaca tgggtggtgg cggttctggt       720
ggtggcggta gtggcggcgg aggaagcggt ggtggcggtt ccggatctca ctccttgaag     780
tatttccaca cttccgtgtc ccggcccggc cgcggggagc cccgcttcat ctctgtgggc     840
tacgtggacg acacccagtt cgtgcgcttc gacaacgacg ccgcgagtcc gaggatggtg     900
ccgcgggcgc cgtggatgga gcaggagggg tcagagtatt gggaccggga gacacggagc     960
gccagggaca ccgcacagat tttccgagtg aacctgcgga cgctgcgcgg ctactacaat    1020
cagagcgagg ccgggtctca caccctgcag tggatgcatg gctgcgagct ggggcccgac    1080
aggcgcttcc tccgcgggta tgaacagttc gcctacgacg gcaaggatta tctcacccctg   1140
aatgaggacc tgcgctcctg gaccgcggtg gacacggcgg ctcagatctc cgagcaaaag    1200
tcaaatgatg cctctgaggc ggagcaccag agagcctacc tggaagacac atgcgtggag    1260
tggctccaca aatacctgga aaggggaag gagacgctgc ttcacctgga gcccccaaag     1320
acacacgtga ctcaccaccc catctctgac catgaggcca ccctgaggtg ctgggctctg    1380
ggcttctacc ctgcggagat cacactgacc tggcagcagg atggggaggg ccatacccag    1440
gacacggagc tcgtgagac caggcctgca ggggatggaa ccttccagaa gtgggcagct     1500
gtggtggtgc cttctggaga ggagcagaga tacacgtgcc atgtgcagca tgagggcta    1560
cccgagcccg tcaccctgag atggaagccg gcttcccagc ccaccatccc catcgtgggc    1620
atcattgctg gcctggttct ccttggatct gtggtctctg gagctgtggt tgctgctgtg    1680
atatggagga gaagagctc aggtggaaaa ggagggagct actataaggc tgagtggagc    1740
gacagtgccc aggggtctga gtctcacagc ttgtaagcct cgactgtgcc ttctagttgc    1800
cagccatctg ttgtttgccc ctcccccgtg ccttccttga ccctggaagg tgccactccc    1860
actgtccttt cctaataaaa tgaggaaatt gcatcgcatt gtctgagtag tgtcattct    1920
attctggggg gtggggtggg gcaggacagc aaggggggagg attgggaaga caatagcagg    1980
catgctgggg ataaggctat ccagcgtgag tctctcctac cctcccgctc tggtccttcc    2040
tctcccgctc tgcaccctct gtggccctcg ctgtgctctc tcgctccgtg acttcccttc    2100
tccaagttct cccttggtgg ccgccgtggg gctagtccag gctgatct cggggaagcg       2160
gcggggtggc ctgggagtgg ggaagggggt gcgcacccgg gacgcgcgct acttgcccct    2220
ttcggcgggg agcaggggag acctttggcc tacggcgacg ggaggtcgg acaaagttt      2280
agggcgtcga taagcgtcag agcgccgagg ttggggagg gtttctcttc cgctctttt     2338
```

<210> SEQ ID NO 18
<211> LENGTH: 515
<212> TYPE: PRT
<213> ORGANISM: Artificial
<220> FEATURE:
<223> OTHER INFORMATION: HLA-E Dimer protein sequence

<400> SEQUENCE: 18

```
Met Ser Arg Ser Val Ala Leu Ala Val Leu Ala Leu Leu Ser Leu Ser
1               5                   10                  15

Gly Leu Gly Ser Gly Glu Gly Arg Gly Ser Leu Leu Thr Cys Gly Asp
            20                  25                  30

Val Glu Glu Asn Pro Gly Pro Met Ser Arg Ser Val Ala Leu Ala Val
        35                  40                  45

Leu Ala Leu Leu Ser Leu Ser Gly Leu Glu Ala Ile Gln Arg Thr Pro
    50                  55                  60

Lys Ile Gln Val Tyr Ser Arg His Pro Ala Glu Asn Gly Lys Ser Asn
65                  70                  75                  80

Phe Leu Asn Cys Tyr Val Ser Gly Phe His Pro Ser Asp Ile Glu Val
                85                  90                  95

Asp Leu Leu Lys Asn Gly Glu Arg Ile Glu Lys Val Glu His Ser Asp
            100                 105                 110

Leu Ser Phe Ser Lys Asp Trp Ser Phe Tyr Leu Leu Tyr Tyr Thr Glu
        115                 120                 125

Phe Thr Pro Thr Glu Lys Asp Glu Tyr Ala Cys Arg Val Asn His Val
    130                 135                 140

Thr Leu Ser Gln Pro Lys Ile Val Lys Trp Asp Arg Asp Met Gly Gly
145                 150                 155                 160

Gly Gly Ser Gly Gly Gly Ser Gly Gly Gly Ser Gly Gly Gly Ser Gly Gly
                165                 170                 175

Gly Ser Gly Ser His Ser Leu Lys Tyr Phe His Thr Ser Val Ser Arg
            180                 185                 190

Pro Gly Arg Gly Glu Pro Arg Phe Ile Ser Val Gly Tyr Val Asp Asp
        195                 200                 205

Thr Gln Phe Val Arg Phe Asp Asn Asp Ala Ala Ser Pro Arg Met Val
    210                 215                 220

Pro Arg Ala Pro Trp Met Glu Gln Glu Gly Ser Glu Tyr Trp Asp Arg
225                 230                 235                 240

Glu Thr Arg Ser Ala Arg Asp Thr Ala Gln Ile Phe Arg Val Asn Leu
                245                 250                 255

Arg Thr Leu Arg Gly Tyr Tyr Asn Gln Ser Glu Ala Gly Ser His Thr
            260                 265                 270

Leu Gln Trp Met His Gly Cys Glu Leu Gly Pro Asp Arg Arg Phe Leu
        275                 280                 285

Arg Gly Tyr Glu Gln Phe Ala Tyr Asp Gly Lys Asp Tyr Leu Thr Leu
    290                 295                 300

Asn Glu Asp Leu Arg Ser Trp Thr Ala Val Asp Thr Ala Ala Gln Ile
305                 310                 315                 320

Ser Glu Gln Lys Ser Asn Asp Ala Ser Glu Ala Glu His Gln Arg Ala
                325                 330                 335

Tyr Leu Glu Asp Thr Cys Val Glu Trp Leu His Lys Tyr Leu Glu Lys
            340                 345                 350

Gly Lys Glu Thr Leu Leu His Leu Glu Pro Pro Lys Thr His Val Thr
        355                 360                 365

His His Pro Ile Ser Asp His Glu Ala Thr Leu Arg Cys Trp Ala Leu
```

```
                370               375               380
Gly Phe Tyr Pro Ala Glu Ile Thr Leu Thr Trp Gln Gln Asp Gly Glu
385               390               395               400

Gly His Thr Gln Asp Thr Glu Leu Val Glu Thr Arg Pro Ala Gly Asp
              405               410               415

Gly Thr Phe Gln Lys Trp Ala Ala Val Val Pro Ser Gly Glu Glu
              420               425               430

Gln Arg Tyr Thr Cys His Val Gln His Glu Gly Leu Pro Glu Pro Val
              435               440               445

Thr Leu Arg Trp Lys Pro Ala Ser Gln Pro Thr Ile Pro Ile Val Gly
              450               455               460

Ile Ile Ala Gly Leu Val Leu Leu Gly Ser Val Val Ser Gly Ala Val
465               470               475               480

Val Ala Ala Val Ile Trp Arg Lys Lys Ser Ser Gly Gly Lys Gly Gly
              485               490               495

Ser Tyr Tyr Lys Ala Glu Trp Ser Asp Ser Ala Gln Gly Ser Glu Ser
              500               505               510

His Ser Leu
      515

<210> SEQ ID NO 19
<211> LENGTH: 2410
<212> TYPE: DNA
<213> ORGANISM: Artificial
<220> FEATURE:
<223> OTHER INFORMATION: HLA-E Trimer Sequence including Target Antigen
      Peptide

<400> SEQUENCE: 19
acagcaaact cacccagtct agtgcatgcc ttcttaaaca tcacgagact ctaagaaaag      60
gaaactgaaa acgggaaagt ccctctctct aacctggcac tgcgtcgctg gcttggagac     120
aggtgacggt ccctgcgggc cttgtcctga ttggctgggc acgcgtttaa tataagtgga     180
ggcgtcgcgc tggcgggcat tcctgaagct gacagcattc gggccgagat gtctcgctcc     240
gtggccttag ctgtgctcgc gctactctct ctttctggcc tgggaagcgg agagggcaga     300
ggaagtcttc taacatgcgg tgacgtggag gagaatcccg cccaatgtc acgatctgtt      360 gcgctggccg tgttggctct tctgtccctg agcggcctcg aggctgttat ggctccgcgg     420
actttaattt taggtggtgg cggatccggt ggtggcggtt ctggtggtgg cggctccatc     480
cagcgtacgc caaagattca ggtttactca cgtcatccag cagagaatgg aaagtcaaat     540
ttcctgaatt gctatgtgtc tgggtttcat ccatccgaca ttgaagttga cttactgaag     600
aatggagaga gaattgaaaa agtggagcat tcagacttgt cttttcagcaa ggactggtct     660 ttctatctct tgtactacac tgaattcacc cccactgaaa aagatgagta tgcctgccgt     720
gtgaaccatg tgactttgtc acagcccaag atagttaagt gggatcgcga catgggtggt     780
ggcggttctg gtggtggcgg tagtggcggc ggaggaagcg gtggtggcgg ttccggatct     840
cactccttga agtatttcca cacttccgtg tcccggcccg gcgcggggga gccccgcttc     900
atctctgtgg gctacgtgga cgacacccag ttcgtgcgct tcgacaacga cgccgcgagt     960
ccgaggatgg tgccgcgggc gccgtggatg gagcaggagg ggtcagagta ttgggaccgg    1020
gagacacgga gcgccaggga caccgcacag atttttcgag tgaacctgcg gacgctgcgc    1080
ggctactaca atcagagcga ggccgggtct cacacccctgc agtggatgca tggctgcgag    1140
ctggggcccg acaggcgctt cctccgcggg tatgaacagt tcgcctacga cggcaaggat    1200
```

```
tatctcaccc tgaatgagga cctgcgctcc tggaccgcgg tggacacggc ggctcagatc   1260
tccgagcaaa agtcaaatga tgcctctgag gcggagcacc agagagccta cctggaagac   1320
acatgcgtgg agtggctcca caaatacctg agaagggga aggagacgct gcttcacctg   1380 gagccccaa agacacacgt gactcaccac cccatctctg accatgaggc caccctgagg   1440
tgctgggctc tgggcttcta ccctgcggag atcacactga cctggcagca ggatggggag   1500
ggccataccc aggacacgga gctcgtggag accaggcctg caggggatgg aaccttccag   1560
aagtgggcag ctgtggtggt gccttctgga gaggagcaga gatacacgtg ccatgtgcag   1620
catgaggggc tacccgagcc cgtcaccctg agatggaagc cggcttccca gcccaccatc   1680
cccatcgtgg gcatcattgc tggcctggtt ctccttggat ctgtggtctc tggagctgtg   1740
gttgctgctg tgatatggag gaagaagagc tcaggtggaa aaggaggag ctactataag   1800 gctgagtgga gcgacagtgc ccagggggtct gagtctcaca gcttgtaagc ctcgactgtg   1860
ccttctagtt gccagccatc tgttgttgc ccctcccccg tgccttcctt gaccctggaa   1920
ggtgccactc ccactgtcct ttcctaataa aatgaggaaa ttgcatcgca ttgtctgagt   1980
aggtgtcatt ctattctggg gggtgggtg gggcaggaca gcaaggggga ggattgggaa   2040
gacaatagca ggcatgctgg ggataaggct atccagcgtg agtctctcct accctccgc   2100 tctggtcctt cctctcccgc tctgcaccct ctgtggccct cgctgtgctc tctcgctccg   2160
tgacttccct tctccaagtt ctccttggtg gcccgccgtg gggctagtcc agggctggat   2220
ctcggggaag cggcggggtg gcctgggagt ggggaagggg gtgcgcaccc gggacgcgcg   2280
ctacttgccc ctttcggcgg ggagcagggg agacctttgg cctacggcga cgggagggtc   2340
gggacaaagt ttagggcgtc gataagcgtc agagcgccga ggttggggga gggtttctct   2400
tccgctcttt                                                           2410
```

<210> SEQ ID NO 20
<211> LENGTH: 479
<212> TYPE: PRT
<213> ORGANISM: Artificial
<220> FEATURE:
<223> OTHER INFORMATION: HLA-E Trimer includinge target peptide antigen

<400> SEQUENCE: 20

```
Met Ala Pro Arg Thr Leu Ile Leu Gly Gly Gly Ser Gly Gly Gly
1               5                   10                  15

Gly Ser Gly Gly Gly Gly Ser Ile Gln Arg Thr Pro Lys Ile Gln Val
            20                  25                  30

Tyr Ser Arg His Pro Ala Glu Asn Gly Lys Ser Asn Phe Leu Asn Cys
        35                  40                  45

Tyr Val Ser Gly Phe His Pro Ser Asp Ile Glu Val Asp Leu Leu Lys
    50                  55                  60

Asn Gly Glu Arg Ile Glu Lys Val Glu His Ser Asp Leu Ser Phe Ser
65                  70                  75                  80

Lys Asp Trp Ser Phe Tyr Leu Leu Tyr Tyr Thr Glu Phe Thr Pro Thr
                85                  90                  95

Glu Lys Asp Glu Tyr Ala Cys Arg Val Asn His Val Thr Leu Ser Gln
            100                 105                 110

Pro Lys Ile Val Lys Trp Asp Arg Asp Met Gly Gly Gly Gly Ser Gly
        115                 120                 125

Gly Gly Gly Ser Gly Gly Gly Gly Ser Gly Gly Gly Gly Ser Gly Ser
    130                 135                 140
```

His Ser Leu Lys Tyr Phe His Thr Ser Val Ser Arg Pro Gly Arg Gly
145                 150                 155                 160

Glu Pro Arg Phe Ile Ser Val Gly Tyr Val Asp Thr Gln Phe Val
            165                 170                 175

Arg Phe Asp Asn Asp Ala Ala Ser Pro Arg Met Val Pro Arg Ala Pro
                180                 185                 190

Trp Met Glu Gln Glu Gly Ser Glu Tyr Trp Asp Arg Glu Thr Arg Ser
            195                 200                 205

Ala Arg Asp Thr Ala Gln Ile Phe Arg Val Asn Leu Arg Thr Leu Arg
210                 215                 220

Gly Tyr Tyr Asn Gln Ser Glu Ala Gly Ser His Thr Leu Gln Trp Met
225                 230                 235                 240

His Gly Cys Glu Leu Gly Pro Asp Arg Arg Phe Leu Arg Gly Tyr Glu
            245                 250                 255

Gln Phe Ala Tyr Asp Gly Lys Asp Tyr Leu Thr Leu Asn Glu Asp Leu
            260                 265                 270

Arg Ser Trp Thr Ala Val Asp Thr Ala Ala Gln Ile Ser Glu Gln Lys
            275                 280                 285

Ser Asn Asp Ala Ser Glu Ala Glu His Gln Arg Ala Tyr Leu Glu Asp
290                 295                 300

Thr Cys Val Glu Trp Leu His Lys Tyr Leu Glu Lys Gly Lys Glu Thr
305                 310                 315                 320

Leu Leu His Leu Glu Pro Pro Lys Thr His Val Thr His His Pro Ile
            325                 330                 335

Ser Asp His Glu Ala Thr Leu Arg Cys Trp Ala Leu Gly Phe Tyr Pro
            340                 345                 350

Ala Glu Ile Thr Leu Thr Trp Gln Gln Asp Gly Glu Gly His Thr Gln
            355                 360                 365

Asp Thr Glu Leu Val Glu Thr Arg Pro Ala Gly Asp Gly Thr Phe Gln
            370                 375                 380

Lys Trp Ala Ala Val Val Val Pro Ser Gly Glu Glu Gln Arg Tyr Thr
385                 390                 395                 400

Cys His Val Gln His Glu Gly Leu Pro Glu Pro Val Thr Leu Arg Trp
            405                 410                 415

Lys Pro Ala Ser Gln Pro Thr Ile Pro Ile Val Gly Ile Ile Ala Gly
            420                 425                 430

Leu Val Leu Leu Gly Ser Val Val Ser Gly Ala Val Val Ala Ala Val
            435                 440                 445

Ile Trp Arg Lys Lys Ser Ser Gly Gly Lys Gly Gly Ser Tyr Tyr Lys
            450                 455                 460

Ala Glu Trp Ser Asp Ser Ala Gln Gly Ser Glu Ser His Ser Leu
465                 470                 475

<210> SEQ ID NO 21
<211> LENGTH: 29
<212> TYPE: PRT
<213> ORGANISM: Artificial
<220> FEATURE:
<223> OTHER INFORMATION: target peptide antigen

<400> SEQUENCE: 21

Met Ala Pro Arg Thr Leu Phe Leu Gly Gly Gly Ser Gly Gly Gly
1               5                   10                  15

Gly Ser Gly Gly Gly Gly Ser Ile Gln Arg Thr Pro Lys
            20                  25

```
<210> SEQ ID NO 22
<211> LENGTH: 283
<212> TYPE: DNA
<213> ORGANISM: Artificial
<220> FEATURE:
<223> OTHER INFORMATION: 5' homology arm for integration into B2M gene

<400> SEQUENCE: 22
acagcaaact cacccagtct agtgcatgcc ttcttaaaca tcacgagact ctaagaaaag      60
gaaactgaaa acgggaaagt ccctctctct aacctggcac tgcgtcgctg gcttggagac    120
aggtgacggt ccctgcgggc cttgtcctga ttggctgggc acgcgtttaa tataagtgga    180
ggcgtcgcgc tggcgggcat tcctgaagct gacagcattc gggccgagat gtctcgctcc    240
gtggccttag ctgtgctcgc gctactctct ctttctggcc tgg                      283

<210> SEQ ID NO 23
<211> LENGTH: 285
<212> TYPE: DNA
<213> ORGANISM: Artificial
<220> FEATURE:
<223> OTHER INFORMATION: 5' homology arm for integration into B2M gene

<400> SEQUENCE: 23
acagcaaact cacccagtct agtgcatgcc ttcttaaaca tcacgagact ctaagaaaag      60
gaaactgaaa acgggaaagt ccctctctct aacctggcac tgcgtcgctg gcttggagac    120
aggtgacggt ccctgcgggc cttgtcctga ttggctgggc acgcgtttaa tataagtgga    180
ggcgtcgcgc tggcgggcat tcctgaagct gacagcattc gggccgagat gtctcgctcc    240
gtggccttag ctctgtgctc gcgctactct ctctttctgg cctgg                    285

<210> SEQ ID NO 24
<211> LENGTH: 343
<212> TYPE: DNA
<213> ORGANISM: Artificial
<220> FEATURE:
<223> OTHER INFORMATION: 3' homology arm for integration into B2M gene

<400> SEQUENCE: 24
gctatccagc gtgagtctct cctaccctcc cgctctggtc cttcctctcc cgctctgcac      60
cctctgtggc cctcgctgtg ctctctcgct ccgtgacttc ccttctccaa gttctccttg    120
gtggcccgcc gtggggctag tccagggctg gatctcgggg aagcggcggg gtggcctggg    180
agtggggaag ggggtgcgca cccgggacgc gcgctacttg cccctttcgg cggggagcag    240
gggagacctt tggcctacgg cgacgggagg gtcgggacaa agtttagggc gtcgataagc    300
gtcagagcgc cgaggttggg ggagggtttc tcttccgctc ttt                      343

<210> SEQ ID NO 25
<211> LENGTH: 21
<212> TYPE: PRT
<213> ORGANISM: Artificial
<220> FEATURE:
<223> OTHER INFORMATION: T2A self-cleaving peptide

<400> SEQUENCE: 25

Gly Ser Gly Glu Gly Arg Gly Ser Leu Leu Thr Cys Gly Asp Val Glu
1               5                   10                  15

Glu Asn Pro Gly Pro
            20
```

```
<210> SEQ ID NO 26
<211> LENGTH: 20
<212> TYPE: PRT
<213> ORGANISM: Artificial
<220> FEATURE:
<223> OTHER INFORMATION: B2m targeting signal

<400> SEQUENCE: 26

Met Ser Arg Ser Val Ala Leu Ala Val Leu Ala Leu Leu Ser Leu Ser
1               5                   10                  15

Gly Leu Glu Ala
            20

<210> SEQ ID NO 27
<211> LENGTH: 218
<212> TYPE: DNA
<213> ORGANISM: Artificial
<220> FEATURE:
<223> OTHER INFORMATION: pBHGA element

<400> SEQUENCE: 27
gcctcgactg tgccttctag ttgccagcca tctgttgttt gcccctcccc cgtgccttcc      60
ttgaccctgg aagtgccac tcccactgtc ctttcctaat aaaatgagga aattgcatcg     120
cattgtctga gtaggtgtca ttctattctg gggggtgggg tggggcagga cagcaagggg    180
gaggattggg aagacaatag caggcatgct ggggataa                            218

<210> SEQ ID NO 28
<211> LENGTH: 30
<212> TYPE: DNA
<213> ORGANISM: Artificial
<220> FEATURE:
<223> OTHER INFORMATION: part of Exon 1 of B2M
<220> FEATURE:
<221> NAME/KEY: misc_feature
<222> LOCATION: (28)..(30)
<223> OTHER INFORMATION: n is a, c, g, or t

<400> SEQUENCE: 28
cctggaggct atccagcgtg agtctctnnn                                      30

<210> SEQ ID NO 29
<211> LENGTH: 60
<212> TYPE: DNA
<213> ORGANISM: Artificial
<220> FEATURE:
<223> OTHER INFORMATION: 5' homology arm
<220> FEATURE:
<221> NAME/KEY: misc_feature
<222> LOCATION: (1)..(3)
<223> OTHER INFORMATION: n is a, c, g, or t

<400> SEQUENCE: 29
nnnatgtctc gctccgtggc cttagctctg tgctcgcgct actctctctt tctggcctgg     60

<210> SEQ ID NO 30
<211> LENGTH: 23
<212> TYPE: DNA
<213> ORGANISM: Artificial
<220> FEATURE:
<223> OTHER INFORMATION: 3' homology arm
<220> FEATURE:
<221> NAME/KEY: misc_feature
<222> LOCATION: (21)..(23)
<223> OTHER INFORMATION: n is a, c, g, or t
```

```
<400> SEQUENCE: 30
gctatccagc gtgagtctct nnn                                      23
```

NON-IMMUNOGENIC ENGINEERED TISSUE AND METHODS OF PRODUCING AND USING THE SAME

CROSS-REFERENCE TO RELATED APPLICATIONS IDC-A1_Sub

The present invention is filed under 35 U.S.C. § 371 as the U.S. national phase of International Application No. PCT/EP2019/068944, filed 15 Jul. 2019, which designated the U.S. and claims the benefit of priority of European Patent Application No. 18183294.0 filed 13 Jul. 2018, the content of which is hereby incorporated by reference it its entirety for all purposes.

SEQUENCE LISTING

The instant application contains a Sequence Listing which has been submitted in ASCII format via EFS-Web and is hereby incorporated by reference in its entirety. Said ASCII copy, created on Jan. 12, 2021, is named SCH-6700-US_SeqListing.txt and is 24 kilobytes in size.

TECHNICAL FIELD OF THE INVENTION

The invention provides a method of producing a non-immunogenic engineered tissue from pluripotent stem cells, the pluripotent stem cells being deficient of MHC class I molecules and comprising an immunomodulatory protein on their surface, wherein the method comprises forming the engineered tissue in the presence of at least one cell type that is essential for the function of the engineered tissue under conditions that allow the formation of the engineered tissue, wherein said at least one cell type has been obtained by inducing the differentiation of the pluripotent stem cells into said at least one cell type that is essential for the function of the engineered tissue under conditions that also allow the formation of the engineered tissue, thereby rendering the engineered tissue to be non-immunogenic to a recipient of the engineered tissue. The present invention further relates to an engineered tissue, a pharmaceutical composition comprising the engineered tissue, medical treatments using the engineered tissue and uses of the engineered tissue.

BACKGROUND ART

The lack of suitable organs or tissues to replace dysfunctional organs or tissues is still a major problem in modern medicine, in particular given that the supply of organ donations is insufficient to cover the medical need and cannot be properly planned.

One approach to overcome is to engineer pluripotent stem cells, in particular human pluripotent stem cells (hPSCs) in functional tissue. This field has recently seen various very promising results. For example, International Patent Application WO2015/025030 describes methods for the production of engineered heart muscle while International Patent Application WO2015/040142 describes improved differentiation protocols to heart tissue. Rao et al, "Engineering human pluripotent stem cells into functional skeletal muscle tissue" Nature Communications, (2018) 9:126, derive induced myogenic progenitor cells (iMPCs) via transient overexpression of Pax7 in paraxial mesoderm cells differentiated from hPSCs. Rao et al report that in 2D culture, iMPCs readily differentiate into spontaneously contracting multinucleated myotubes and a pool of satellite-like cells endogenously expressing Pax7. The review of Lancaster and Knoblich, "Organogenesis in a dish: Modeling development and disease using organoid technologies" Science 345, 1247125 (2014) describes inter alia organoids (stem cell-derived three-dimensional cultures) derived from human PSCs of gut, kidney, brain, and retina tissue. Similarly, the review of Llonch et al "Organoid technology for retinal repair" Developmental Biology 433 (2018) 132-143 discusses PSC-derived retinal organoids as an important tool for generating retinal tissue in vitro that is widely used to generate high amounts of photoreceptors that can be further developed towards potential cell-based therapies. Finally, Pagliuca et al, "Generation of Functional Human Pancreatic b Cells In Vitro" Cell 159, 428-439 (2014) report a scalable differentiation protocol that can generate hundreds of millions of glucose-responsive b cells from hPSC in vitro.

However, the methods described above, while resulting, for example, in a functioning heart tissue or functional skeletal tissue, still face the problem of transplant rejection, if the utilized pluripotent stem cells are derived from an allogeneic donor and/or are not histologically compatible.

Accordingly, there is not only the need for a functional tissue or organoid in general for therapeutic application, like e.g. a functional heart tissue, but also for an improved functional tissue or organoid, like e.g. an improved heart tissue that is not rejected in recipients although it was derived from an allogeneic donor. The present invention aims to solve this problem.

SUMMARY OF THE INVENTION

The problem is solved by the subject-matter as defined in the claims. The invention provides a method of producing a non-immunogenic engineered tissue from pluripotent cells, an engineered tissue, a pharmaceutical composition comprising the engineered tissue, medical treatments using the engineered tissue and uses of the engineered tissue.

Accordingly, the present invention relates to a method of producing a non-immunogenic engineered tissue from pluripotent stem cells, the pluripotent stem cells being deficient of endogenous MHC class I molecules presented on the cell surface of the pluripotent stem cell and comprising an immunomodulatory protein on their surface, wherein the method comprises forming the engineered tissue in the presence of at least one cell type that is essential for the function of the engineered tissue under conditions that allow the formation of the engineered tissue, wherein said at least one cell type has been obtained by the differentiation of the pluripotent stem cells into said at least one cell type, thereby rendering the engineered tissue to be non-immunogenic to a recipient of the engineered tissue.

The present invention also relates to a method of producing a non-immunogenic engineered tissue from pluripotent stem cells, the pluripotent stem cells being deficient of endogenous MHC class I molecules presented on the cell surface of the pluripotent stem cell and comprising an immunomodulatory protein on their surface, wherein the method comprises inducing the differentiation of the pluripotent stem cells into at least one cell type that is essential for the function of the engineered tissue under conditions that also allow the formation of the engineered tissue, thereby rendering the engineered tissue to be non-immunogenic to a recipient of the engineered tissue.

In embodiments of the invention, the engineered tissue (a) is not recognized as allogenic by the recipient's effector T cells, and/or, (b) is resistant to NK-mediated lysis. Preferably, the engineered tissue does not bind anti-HLA antibodies, preferably the tissue does not bind anti-HLA-A or anti-HLA-B antibodies.

The immunomodulatory protein may be a single chain fusion HLA class I protein, wherein more preferably the single chain fusion HLA class I protein comprises at least a portion of B2M covalently linked to at least a portion of an HLA class Iα chain selected from the group consisting of HLA-A, HLA-B, HLA-C, HLA-E, HLA-F and HLA-G. Most preferably, the single chain fusion HLA class I protein comprises at least a portion of B2M and at least a portion of HLA-A, or the single chain fusion HLA class I protein comprises at least a portion of B2M and at least a portion of HLA-A0201, or the single chain fusion HLA class I protein comprises at least a portion of B2M and at least a portion of HLA-E, or the single chain fusion HLA class I protein comprises at least a portion of B2M and at least a portion of HLA-G, or the single chain fusion HLA class I protein comprises at least a portion of B2M and at least a portion of HLA-B, or the single chain fusion HLA class I protein comprises at least a portion of B2M and at least a portion of HLA-C, or the single chain fusion HLA class I protein comprises at least a portion of B2M and at least a portion of HLA-F.

In embodiments of the invention, the pluripotent stem cell further expresses a target peptide antigen that is presented by the single chain fusion HLA class I protein on the pluripotent cell surface, wherein more preferably the target peptide antigen is covalently linked to the single chain fusion HLA class I protein, wherein the target peptide antigen may comprise the sequence VMAPRTLFL (SEQ ID NO: 1).

In embodiment of the invention, essentially all copies of the beta-microglobulin 2 gene are disrupted in the pluripotent stem cells.

In embodiments of the invention, the method comprises forming the engineered tissue in the presence of at least one second cell type that forms part of the issue. The second cell type that forms part of the engineered tissue depends on the kind of tissue that is to be engineered (for example, if an engineered heart muscle tissue or liver tissue is to be formed) an may, for example, be a fibroblast, endothelial cell, a smooth muscle cell, a chondrocyte, an adipocyte, a reticular cell or a mesenchymal stem cell.

The engineered tissue may be selected from the group consisting of heart tissue, liver tissue, kidney tissue, brain tissue, pancreatic tissue, lung tissue, skeletal muscle tissue, gastrointestinal tissue, neuronal tissue, skin tissue, bone tissue, bone marrow, fat tissue, connective tissue, retinal tissue and blood vessel tissue.

Preferably, in one embodiment of the method of the invention, the engineered tissue is heart tissue, wherein the method further comprises: (i) cultivating the pluripotent stem cells in a basal medium comprising an effective amount of (a) BMP4, Activin A, FGF2, a GSK3-inhibitor, and (b) a serum-free supplement resulting in a final concentration of 0.5-50 mg/ml albumin, 1-100 µg/ml transferrin, 0.1-10 µg/ml ethanol amine, 0.003-0.3 µg/ml sodium selenite, 0.4-40 µg/ml L-Carnitine HCl, 0.1-10 µg/ml Hydrocortisone, 0.05-5 µl/ml Fatty acid supplement, 0.0001-0.1 µg/ml triodo-L-thyronine (T3), thereby inducing mesoderm differentiation of the pluripotent stem cells; (ii) cultivating the cells obtained in step (i) in a basal medium comprising an effective amount of an inhibitor of the Wnt-signaling pathway and a serum-free supplement as in (i), thereby inducing cardiac differentiation of the cells; and (iii) cultivating the cells obtained in step (ii) in a basal medium comprising an effective amount of a serum-free supplement as in (i), under mechanical stimulation, thereby promoting cardiac maturation.

In one embodiment of the method of the invention, the tissue formation is carried out in the presence of a hydrogel, preferably an extracellular matrix protein, and most preferably a collagen hydrogel.

In one embodiment of the method of the invention, the method further comprises: (iv) providing a serum-free reconstitution mixture in one or more moulds, said reconstitution mixture comprising (a) a serum-free minimum essential medium; (b) a serum-free supplement resulting in a final concentration of 0.5-50 mg/ml albumin, 1-100 µg/ml transferrin, 0.1-10 µg/ml ethanol amine, 0.003-0.3 µg/ml sodium selenite, 0.4-40 µg/ml L-Carnitine HCl, 0.1-10 µg/ml Hydrocortisone, 0.05-5 µl/ml Fatty acid supplement, 0.0001-0.1 µg/ml triodo-L-thyronine (T3) and 0.2-2 mg/ml collagen; and (c) the cells obtained in step (iii) and a cell type that forms part of the engineered tissue, preferably human non-myocytes, wherein optionally the cells that form part of the engineered tissue are derived from the pluripotent stem cells, wherein 20 to 80% of the total cell mixture are the cells obtained in step (iii); wherein the reconstitution mixture has a pH of 7.2 to 7.6; (v) culturing the serum-free reconstitution mixture in said one or more moulds, whereby the serum-free reconstitution mixture is allowed to condense for at least 15 min; (vi) culturing the mixture obtained in step (v) in said one or more moulds in a serum-free EHM culture medium until the mixture condenses to at least 50% of its original thickness, wherein said EHM culture medium comprises (a) a basal medium comprising 0.5-3 mmol/L Ca$^{2+}$; (b) a serum-free supplement as defined in (i)(b); (c) 0.5-10 mmol/L L-glutamine; (d) 0.01-1.0 mmol/L ascorbic acid; (e) 1-100 ng/ml IGF-1; and (f) 1-10 ng/ml TGFβ1; (vii) culturing the mixture obtained in step (iii) under mechanical stretching in a serum-free EHM culture medium as defined in step (iii) (a)-(f), whereby force-generating engineered heart tissue is formed.

Preferably, the pluripotent stem cells are selected from the group consisting of embryonic stem cells, induced pluripotent stem cells and parthenogenetic stem cells Preferably, the pluripotent stem cells are pluripotent stem cells of primate origin, preferably human pluripotent stem cells. Preferably, the pluripotent stem cells. Preferably, the pluripotent stem cell is ND50039 of the NINDS Human Cell and Data Repository.

Preferably, the method of the invention further comprises inducing the differentiation of the pluripotent stem cells into at least one cell type that forms part of the engineered tissue, wherein the cells that are essential for the function of the engineered tissue and the cells that form part of the engineered tissue are contacted after differentiation to form a engineered tissue. The (second) cell type that may form part of the engineered tissue may be, but is not limited to a fibroblast, endothelial cell, smooth muscle cell, a chondrocyte, an adipocyte, a reticular cell or mesenchymal stem cell, to name only a few illustrative examples.

Preferably, the disruption of B2M and/or insertion of the immunomodulatory protein is/are mediated by engineered nucleases. More preferably, the engineered nuclease is selected from the group consisting of meganucleases, zinc finger nucleases (ZFNs), transcription activator-like effector-based nucleases (TALEN), and the clustered regularly interspaced short palindromic repeats (CRISPR/Cas9). Most preferably, the engineered nuclease is CRISPR/Cas9 and the crRNA is selected from the group consisting of ACTCACGCTGGATAGCCTCC (SEQ ID NO: 2), GAGTAGCGCGAGCACAGCTA (SEQ ID NO: 3) GGCCGAGATGTCTCGCTCCG (SEQ ID NO: 4), ACT-CACGCTGGATAGCCTCCAGG (SEQ ID NO: 5), GAGTAGCGCGAGCACAGCTAAGG (SEQ ID NO: 6) and GGCCGAGATGTCTCGCTCCGTGG (SEQ ID NO: 7).

In one embodiment, the pluripotent stem cells are differentiated into said at least one cell type while the engineered tissue is formed.

The present invention also relates to a engineered tissue comprising, pluripotent stem cells, the pluripotent stem cells being deficient of MHC class I molecules and comprising an immunomodulatory protein on their surface, wherein the pluripotent stem cells are differentiated into a cell type that is essential for the function of the engineered tissue under conditions that also allow the formation of the engineered tissue, thereby rendering the engineered tissue to be non-immunogenic to a recipient of the engineered tissue.

The present invention also relates to an engineered tissue obtainable by the method of the invention. The present invention further relates to an engineered tissue obtained by the method of the invention.

Preferably, the engineered tissue further comprises extracellular matrix biomaterial. More preferably, the extracellular matrix biomaterial is alginate, a hydrogel, a collagen hydrogel, a fibrin hydrogel, or synthetic matrices such as polylactic acid, polyglycolic acid, and polyglycerol sebacate (biorubber), and poly(octamethylene maleate (anhydride) citrate, most preferably the extracellular matrix biomaterial is Collagen type I.

Preferably, the engineered tissue (a) is not recognized as allogenic by the recipient's effector T cells, (b) does not bind anti-HLA antibodies, and/or (c) is resistant to NK-mediated lysis.

The present invention further relates to a pharmaceutical composition comprising the engineered tissue of the invention.

The present invention further relates to the engineered tissue of the invention or the pharmaceutical composition of the invention for use in a method of treatment of a disease condition.

The present invention further relates to a method of treating a disease condition, comprising administering to a subject in need thereof an effective amount of the engineered tissue of the invention or the pharmaceutical composition of the invention.

The engineered tissue or the pharmaceutical composition for use of the invention or the method of treatment of the invention, wherein the disease condition is selected from the group consisting of diabetes, an autoimmune disease, cancer, infection, myocardial infarction, heart failure, skeletal or joint condition, osteogenesis imperfecta, burns, liver failure, kidney failure, brain damage or soft tissue damage.

The present invention further relates to the use of the engineered tissue of anyone of the invention in (a) an in vitro-model for drug toxicity screening; and/or (b) as a research tool.

The present invention further relates to a nucleic acid comprising the at least one of SEQ ID NOs: 2-7.

The present invention also relates to the use of the nucleic acid for disrupting (the expression) of the B2M gene.

The invention will be better understood with reference to the detailed description when considered in conjunction with the drawings, the non-limiting examples and the accompanying claims

BRIEF DESCRIPTION OF THE DRAWINGS

FIG. 1 depicts a section surrounding exon 1 (grey, positions 201 to 327) of the sequence of the B2M gene. The 550 base pairs shown in FIG. 1 correspond, e.g. to sequence positions 4811 to 5360 of NCBI GenBank entry NG_012920, version NG_012920.2 of 3 Jun. 2018, which shows the complete gene. Underlined are the binding sites of the three crRNAs shown below the gene sequence. SEQ ID NO: 6 (B2M_CR1) binds to positions 287 to 299 to the complementary strand, SEQ ID NO: 5 (B2M_CR2) binds to positions 311 to 333 of the complementary strand and SEQ ID NO: 7 (B2M_CR3) binds to positions 254 to 276. The relevant PAMs are shown in bold and italic. Further highlighted is the translation start signal ATG (double underlined).

FIG. 2 depicts the resulting sequences of 4 different PSC clones after gene editing by the CRISPR/Cas9 nuclease at sequence positions 201 to 350 of the B2M gene section shown in FIG. 1. For each clone, the resulting sequence of both alleles is shown. Underlined are the binding sites of the three crRNAs. SEQ ID NO: 6 (B2M_CR1) binds to positions 287 to 299 to the complementary strand, SEQ ID NO: 5 (B2M_CR2) binds to positions 311 to 333 of the complementary strand and SEQ ID NO: 7 (B2M_CR3) binds to positions 254 to 276. Further highlighted are the start codon (double underlined), the PAM (bold and italic) and mutations (waves). Deletions are marked by "-".

FIG. 4 depicts exemplary DNA sequences that allow an overexpression of an immunomodulatory protein on the surface of the pluripotent stem cells and may be incorporated into a suitable vector. In general, an immunomodulatory protein may comprise a functional B2M fused to HLA gene. In the exemplary embodiments shown in FIG. 4, a human B2M is fused to a human HLA-E gene. The open reading frame of the "dimer" marked in grey translates to a protein shown in SEQ ID NO: 18. This dimer comprises B2M and HLA-E fused by a $(G_4S)_4$. The open reading frame of the "trimer" marked in grey translates to a protein shown in SEQ ID NO: 20. This protein comprises in addition to B2M and HLA-E also a target peptide antigen with the sequence MAPRTLFLGGGGSGGGGSGGGGSIQRTPK (SEQ ID NO: 21). Using such an exemplary target peptide antigen fused to the single chain B2M-HLA-E dimer may increase the stability of the complex. Accordingly, SEQ ID NOs: 18 and 20 are exemplary embodiments of the immunomodulatory protein. The sequences not marked in grey before and after the open reading frames are homology arms that mediate the integration into the B2M gene.

FIG. 5A shows a schematic representation of Crispr/Cas9 targeting induced HDR mediated HLA-E Dimer and Trimer knock-in in B2M KO hIPSCs. FIG. 5B shows brightfield image of hIPSCs untransfected (Ctrl), and transfected with the plasmids containing HLA-E Dimer and Trimer donor sequences at 48 hours after transfection. FIG. 5C shows hIPSCs expressing GFP after transfection with pmaxGFP plasmid (left) and flow cytometry analysis of GFP+ cells (right).

FIG. 6A shows a schematic representation of B2M locus and the primers encompassing the 5'-homology arm and donor sequence for PCR amplification. Agarose gel electrophoresis demonstrates Crispr/Cas9 induced HDR mediated gene integration in hIPSCs transfected with HLA-E Dimer and Trimer donor plasmids. FIG. 6B shows genotyping of clones for HLA-E Dimer and FIG. 6C shows genotyping for HLA-E Trimer insertion. WT: Wild type, PD: Plasmid DNA, HLA-E: hIPSC pool transfected with HLA-E donor plasmid.

FIG. 7A is a schematic representation of B2M locus, primers encompassing the 5' and 3'-homology arm and donor sequence for PCR amplification. FIG. 7B shows genotyping of clones for HLA-E Dimer and FIG. 7C shows genotyping for HLA-E Trimer insertion.

FIG. 10A shows a brightfield image of hIPSCs and their subsequent differentiation into CMs expressing α-actinin, cTnT and Nuclei. Highly pure CMs >90% α-actinin+ as measured by flow cytometry (Right). Isotype control tracing is shown as unfilled area. FIG. 10B shows a flow cytometry analysis of CMs derived from WT, B2M KO, HLA-E Dimer Clone #5 and 78, HLA-E Trimer Clone #66 and 100 hIPSC lines for the expression of B2M, HLA-B, C and HLA-E detected at APC-A, PE-A and Pacific Blue-A channels respectively. Scale bar: 50 μm.

FIG. 11A shows a schematic representation of the EHM manufacturing process; hiPSC-derived cardiomyocytes (CMs) from naïve GMP hiPSC line ND50039 (also known as TC1133 and available from Lonza) and from the hiPSC line TC1133 genetically modified as described herein were mixed with human dermal fibroblasts in collagen type I according to Tiburcy et al. 2017 to form ring-shaped EHM. FIG. 11B shows the consolidation phase of EHM for 3 days in casting molds, functional maturation under mechanical loading on flexible stretchers up to 4 weeks and measurement of force of contraction (FOC) under isometric conditions in a thermostatted organ bath. FIG. 11C shows the force of contraction (FOC) recorded under electrical stimulation in genetically naïve (wild-type) EHM and EHM comprising B2M KO, HLAE Dimer and Trimer KI iPSC-derived cardiomyocytes. FOC responses were recorded under increasing calcium concentrations (n=4/group).

DETAILED DESCRIPTION OF THE INVENTION

Figure 3:
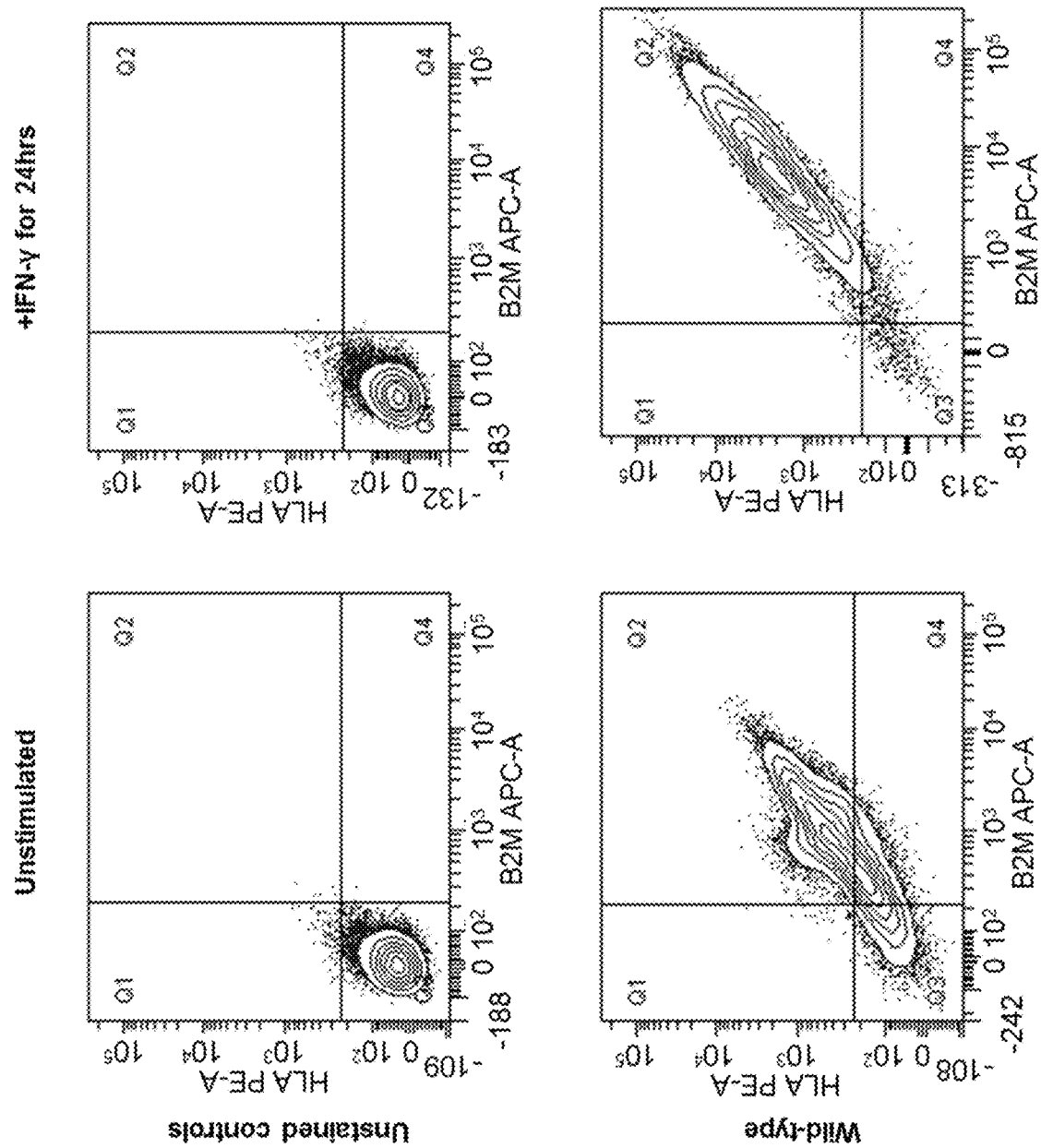
FIG. 3 depicts the results of a flow cytometry analysis of 4 different PSC clones after gene editing by the CRIPSR/Cas9 nuclease in comparison to a wild type PSC and a non-stained control. The cell surface expression of B2M (APC, x axis) and HLA (PE, y axis) were analyzed in unstimulated PSC (left) and PSC (right) that were stimulated with interferon γ for 24 h.
Figure 3:
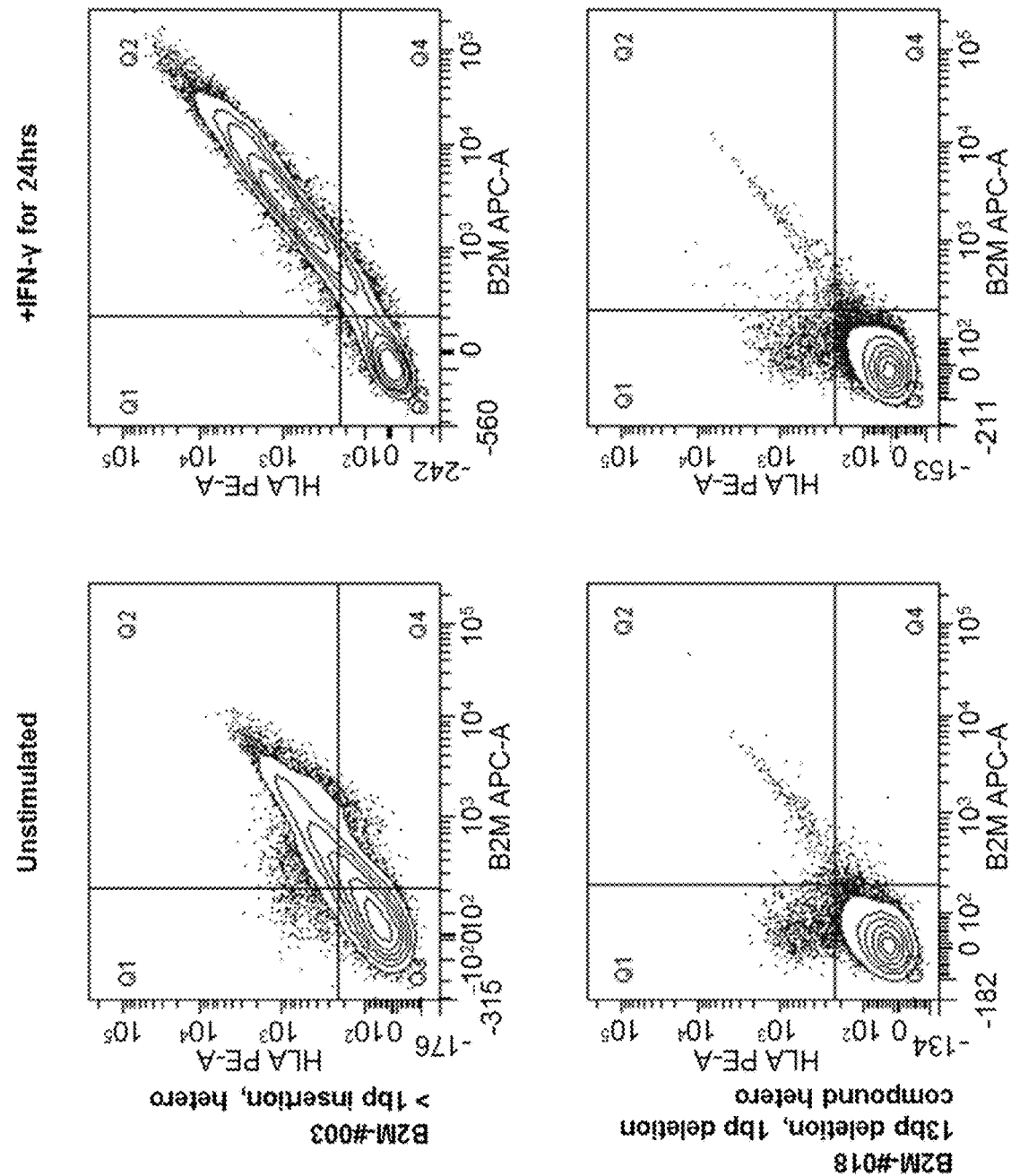
Figure 3:
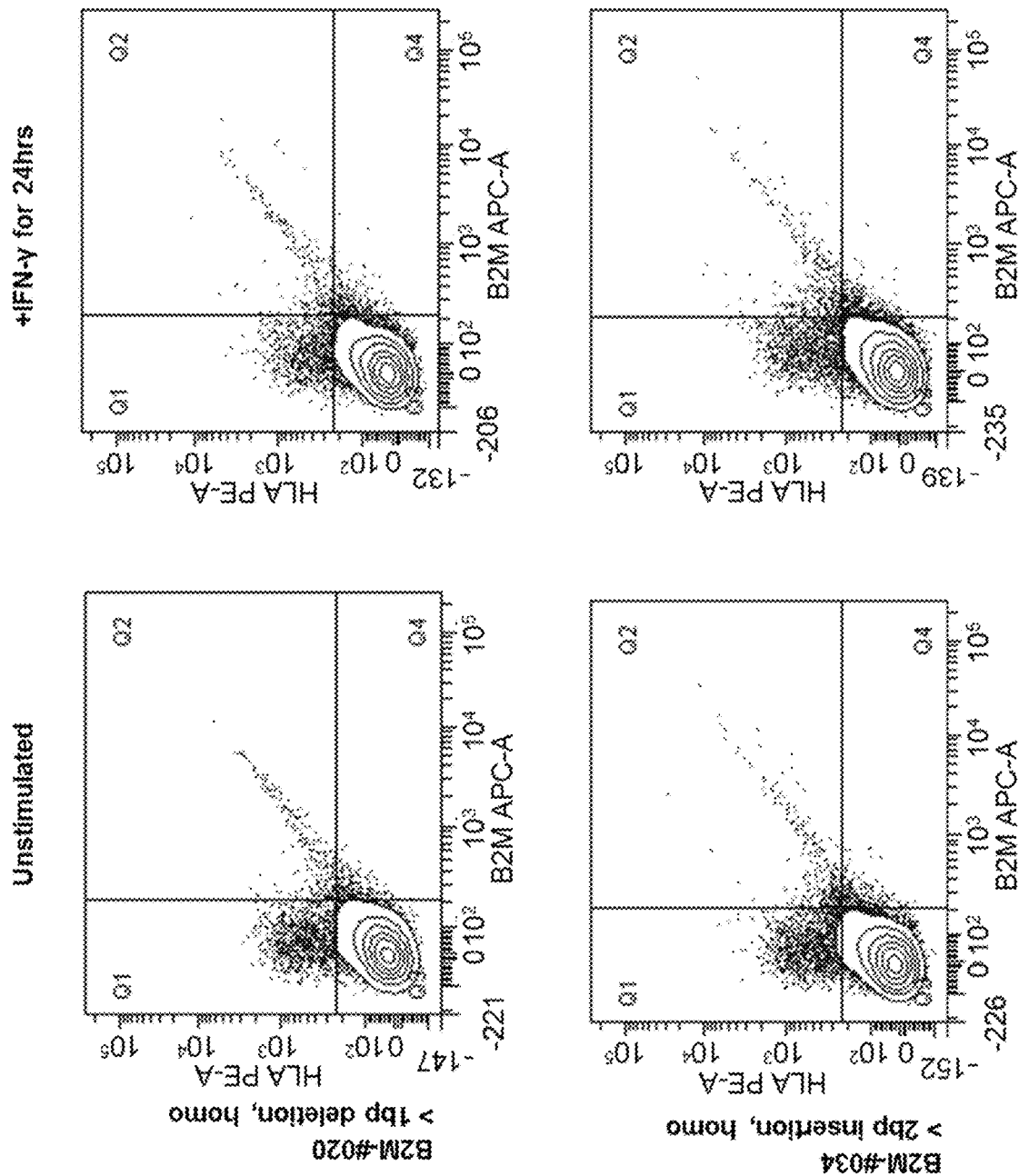

The invention is based on the surprising finding that pluripotent stem cells that lack expression of functional β2-microglobulin (B2M), thereby being deficient of MHC class I molecules, but express HLA-E, i.e. an immunomodulatory protein, can be used for the production of a engineered tissue that is non-immunogenic to a recipient of the engineered tissue. The use of such pluripotent stem cells that are deficient of MHC class I molecules and comprise an immunomodulatory protein on their surface has the advantage that it provides an allogeneic engineered tissue that is however no longer recognized as allogeneic by the recipient's immune system. Therefore, and importantly, the so obtained allogeneic engineered tissue (that is also referred herein as "robotic tissue or "stealth tissue" with respect to the immune system of the recipient) that is obtained by means of a stem cell that is differentiated into a cell that is essential to the function of the tissue does not require a recipient (patient) of the tissue to be subjected to immunosuppression in order to either completely avoid or at least decrease the risk of tissue rejection or complications such as graft-versus host disease. This makes the robotic tissue of the present invention an ideal candidate for therapeutic applications of functional tissues such as engineered heart tissue, liver tissue, retinal tissue or renal tissue, for example, in organ or tissue replacement transplantations. In this context, it is noted that disruption of the β2-microglobulin (B2M) gene to eliminate surface expression of MHC class I molecules to provide cells deficient of MHC class I (HLA class I) has already been described in 1992 by International Patent Application WO 92/09688 (cf. also International Patent Application see WO 2012/145384), however this approach leaves the cells vulnerable to lysis by natural killer (NK) cells as reported by Gornalusse et al "HLA-E-expressing pluripotent stem cells escape allogeneic responses and lysis by NK cells" (2017), Nature Biotechnology, 35(8):765-772. In order to address this "missing-self" response, Gornalusse et al use forced expression of minimally polymorphic HLA-E molecules. By this approach, Gornalusse et al generate pluripotent stem cells that are able to be differentiated into CD45+ hematopoietic cells that were able to escape allogeneic responses and lysis by NK cells.

In the method of the present invention, the pluripotent stem cells are differentiated into at least one cell type that is essential for the function of the desired engineered tissue. This differentiation may take place before the engineered tissue is formed (see in this context, Example 3 and FIG. 10A, for instance) or the differentiation of the pluripotent stem cells may be performed while forming the engineered tissue. In other words, the pluripotent stem cells may be differentiated before the actual production of the engineered tissue starts or the differentiation of the pluripotent stem cells can be performed at the same time (concurrently) with the production of the engineered tissue. Such an engineered tissue may comprise only one cell type, for example, only insulin-producing pancreatic beta cells or, for example, as described by Rao et al, Nature Communications, (2018), supra, induced myogenic progenitor cells (iMPCs) differentiated from hPSCs, wherein the iMPCs can readily differentiate into spontaneously contracting multinucleated myotubes which under 3D culture conditions, can reproducibly form functional skeletal muscle tissues (iSKM bundles) containing aligned multinucleated myotubes that exhibit positive force-frequency relationship and robust calcium transients in response to electrical or acetylcholine stimulation. In accordance with the above, it is also possible that the engineered tissue comprise two or more cell types that are essential for the function of the desired engineered tissue. An illustrative example of such a tissue is pancreatic tissue, more specifically the pancreatic islets, comprising Alpha cells producing glucagon (20% of total islet cells), Beta cells producing insulin and amylin (≈70%), Delta cells producing somatostatin (<10%), PP cells (gamma cells or F cells) producing pancreatic polypeptide (<5%) and Epsilon cells producing ghrelin (<1%). Alternatively, the engineered tissue may comprise two or more cell types, for example, one cell type that is essential for the function of the engineered tissue and a supporting (second) cell type that also forms part of the (engineered) tissue. An illustrative example for an engineered tissue that comprises such at least two different cell types is heart tissue, which mainly comprises cardiomyocytes (as the first or at least one cell type) exerting the function of the tissue being a muscle, and fibroblasts, which (as the second cell type) provide connective tissue (see WO 2015/025030, for example). In illustrative examples of such heart tissue being formed in accordance with WO 2015/025030, an engineered heart tissue of the present invention may be formed from a mixture of mixture of human cardiac myocytes and human non-myocytes, wherein 20 to 80% of the total cell mixture are cardiac myocytes (that have been differentiated from the pluripotent stem cell of the present invention) and the remaining cells are non-cardiomyocytes such as fibroblasts (i.e. cells of the second cell type that forms part of the tissue of the invention).

Accordingly, the present invention relates to a method of producing a non-immunogenic engineered tissue from pluripotent stem cells, the pluripotent stem cells being deficient of endogenous MHC class I molecules presented on the cell surface of the pluripotent stem cell and comprising an immunomodulatory protein on their surface, wherein the method comprises forming the engineered tissue in the presence of at least one cell type that is essential for the function of the engineered tissue under conditions that allow the formation of the engineered tissue, wherein said at least one cell type has been obtained by the differentiation of the pluripotent stem cells into said at least one cell type, thereby rendering the engineered tissue to be non-immunogenic to a recipient of the engineered tissue.

The present invention further relates to a method of producing a non-immunogenic engineered tissue from pluripotent stem cells, the pluripotent stem cells being deficient of MHC class I molecules and comprising an immunomodulatory protein on their surface, wherein the method comprises inducing the differentiation of the pluripotent stem cells into at least one, or, for example, two, three, four, or five cell type(s) that is/are essential for the function of the engineered tissue under conditions that also allow the formation of the engineered tissue, thereby rendering the engineered tissue to be non-immunogenic to a recipient of the engineered tissue.

The term "pluripotent stem cell" (PSC) as used herein refers to cells that are able to differentiate into every cell type of the body. As such, pluripotent stem cells offer the unique opportunity to be differentiated into essentially any tissue or organ. Currently, the most utilized pluripotent cells are embryonic stem cells (ESC) or induced pluripotent stem cells (iPSC). Human ESC-lines were first established by Thomson and coworkers (Thomson et al. (1998), Science 282:1145-1147). Human ESC research recently enabled the development of a new technology to reprogram cells of the body into an ES-like cell. This technology was pioneered by Yamanaka and coworkers in 2006 (Takahashi & Yamanaka (2006), Cell, 126:663-676). Resulting induced pluripotent cells (iPSC) show a very similar behavior as ESC and, importantly, are also able to differentiate into every cell of the body. Moreover, it was reported that also parthenogenetic stem cells are suitable for EHM-production in a mouse model (Didié et al. (2013), J Clin Invest., 123:1285-1298); the use of human parthenogenetic stem cells according to WO 2015/025030 will likely yield human EHM. Accordingly, the pluripotent stem cells used herein can, for example, be selected from embryonic stem cells, induced pluripotent stem cells, and parthenogenetic stem cells. In the context of the present invention, these pluripotent stem cells are however preferably not produced using a process which involves modifying the germ line genetic identity of human beings or which involves use of a human embryo for industrial or commercial purposes. Preferably, the pluripotent stem cells are of primate origin, more preferably human. Suitable PSC's, including induced PSCs, can for example, be obtained from the NIH human embryonic stem cell registry, the European Bank of Induced Pluripotent Stem Cells (EBiSC), the Stem Cell Repository of the German Center for Cardiovascular Research (DZHK), or ATCC, to name only a few sources. Pluripotent stem cells are also available for commercial use, for example, from the NINDS Human Sequence and Cell Repository (stemcells.nindsgenetics.org) which is operated by the U.S. National Institute of Neurological Disorders and Stroke (NINDS) and distributes human cell resources broadly to academic and industry researchers. One illustrative example of a suitable cell line that can be used in the present invention is the cell line ND50039, an induced (unedited) pluripotent stem cell that has been derived from a cord blood stem cell. Further exemplary iPSC cell lines that can be used in the present invention, include but are not limited to, the Human Episomal iPSC Line of Gibco™ (order number A18945, Thermo Fisher Scientific), or the iPSC cell lines ATCC ACS-1004, ATCC ACS-1021, ATCC ACS-1025, ATCC ACS-1027 or ATCC ACS-1030 available from ATTC. Alternatively, any person skilled in the art of reprogramming can easily generate suitable iPSC lines by known protocols such as the one described by Okita et al, "A more efficient method to generate integration-free human iPS cells" Nature Methods, Vol. 8 No. 5, May 2011, pages 409-411 or by Lu et al "A defined xeno-free and feeder-free culture system for the derivation, expansion and direct differentiation of transgene-free patient-specific induced pluripotent stem cells", Biomaterials 35 (2014) 2816e2826.

As explained above, the (induced) pluripotent stem cell that is used in the present invention can be derived from any suitable cell type (for example, from a stem cell such as a mesenchymal stem cell, or an epithelial stem cell or a differentiated cells such as fibroblasts) and from any suitable source (bodily fluid or tissue). Examples of such sources (body fluids or tissue) include cord blood, skin, gingiva, urine, blood, bone marrow, any compartment of the umbilical cord (for example, the amniotic membrane of umbilical cord or Wharton's jelly), the cord-placenta junction, placenta or adipose tissue, to name only a few. In one illustrative example, is the isolation of CD34-positive cells from umbilical cord blood for example by magnetic cell sorting using antibodies specifically directed against CD34 followed by reprogramming as described in Chou et al. (2011), Cell Research, 21:518-529. Baghbaderani et al. (2015), Stem Cell Reports, 5(4):647-659 show that the process of iPSC generation can be in compliance with the regulations of good manufacturing practice to generate cell line ND50039. Accordingly, the pluripotent stem cell preferably fulfils the requirements of the good manufacturing practice.

A cell or pluripotent stem cell, which is "deficient of endogenous MHC class I molecules presented on the cell surface" does not present a functional MHC class I molecule on its surface, i.e. the surface of the cell or the pluripotent stem cell, nor comprises a functional MHC class I molecule in its cell membrane. In this context, the term "endogenous" relates to any MHC class protein I, which naturally is comprised in the cell or pluripotent stem cell and not artificially introduced. However, this increases the risk of a rejection reaction of the immune system of the recipient because a lack of MHC class I molecules on the cell surface might be interpreted as a "missing self"-signal by the immune system. Accordingly, the limitation that the cell or pluripotent stem cells is deficient of MHC class I molecules on their surface, does not apply to any immunomodulatory protein, which may be introduced into the pluripotent stem cell and/or a recombinant immunomodulatory protein. In one embodiment, the deficiency of MHC class I molecules on the cell surface can be achieved by disrupting all copies of the beta 2-microglobulin gene in the pluripotent stem cells. The MHC complex is a heterodimer of alpha-microglobulin and beta 2-microglobulin. Hence, if beta 2-microglobulin is missing, no functional MHC class I complex can be assembled and consequently, no MHC class I molecule is present on the cell membrane and/or cell surface.

Many possible ways are known to the person skilled in the art to modify the genome of the pluripotent stem cell in such a way that they are deficient of MHC class I molecules and comprise an immunomodulatory protein. It should be noted that a pluripotent stem cell of the invention, which is deficient of MHC class I molecules, may express an immunomodulatory protein, even if it is an MHC class I molecule such as HLA-E described herein. Accordingly, the term "deficient of MHC class I molecules" may relate to endogenous MHC class I molecules and does not exclude the presence of a (recombinant) immunomodulatory protein.

In the pluripotent stem cells of the invention the B2M gene may be disrupted so that no functional endogenous B2M protein is produced from the disrupted genetic loci. In certain embodiments, the disruption results in expression of non-functional B2M proteins, including but not limited to truncations, deletions, point mutations and insertions. In other embodiments, the disruption results in no protein expression from the B2M gene.

Pluripotent stem cells deficient in B2M expression are unable to express HLA class I proteins on the cell surface. HLA class I-deficiency provides further benefits; for example, cells without HLA class I expression cannot present auto-antigens that would otherwise prevent successful cell therapies for autoimmune diseases such as diabetes and rheumatoid arthritis. Similarly, therapeutic gene products introduced by the inventive cell therapies (e.g., dystrophin) that are missing in patients with certain genetic diseases (e.g., muscular dystrophy) will not be presented and recognized by the immune system as neo-antigens in replacement therapies.

Any suitable technique for disrupting one, two or all copies of the B2M gene can be used; exemplary techniques are disclosed throughout the application and are within the level of skill in the art based on the teachings herein and the teachings known in the art. Exemplary other techniques can be found, for example, in U.S. Patent Application Publication Number US 2008/0219956, published Sep. 11, 2008. These techniques may optionally include steps to remove non-human DNA sequences from the cells after B2M gene disruption.

An exemplary embodiment of this method is using an adeno-associated virus (AAV) gene targeting vector, optionally including removing the transgene used for targeting via techniques such as those described below, or by removing the transgene used for targeting by Cre-mediated loxP recombination, or other suitable recombination techniques. See Khan et al. (2011), Protocol, 6:482-501. It is within the level of those of skill in the art, based on the teachings herein and known in the art, to utilize a variety of techniques for making the B2M−/− pluripotent stem cells, i.e. pluripotent stem cells being deficient of MHC class I molecules, preferably human cells, of the invention.

The disruption of B2M and/or the insertion of the gene encoding the immunomodulatory protein may also be performed by the use of engineered nucleases. These nucleases are able to introduce single and/or double strand breaks in DNA. The engineered nuclease may be selected from the group consisting of meganucleases, zinc finger nucleases (ZFN), transcription activator-like effector-based nucleases (TALEN), and the clustered regularly interspaced short palindromic repeats (CRISPR/Cas9).

CRISPR describes a family of DNA sequences in bacteria. The sequences contain snippets of DNA from viruses that have attacked the bacterium. These snippets are used by the bacterium to detect and destroy DNA from similar viruses during subsequent attacks. These sequences play a key role in a bacterial defense system, and form the basis of a technology known as CRISPR/Cas9 that effectively and specifically changes genes within organisms. The CRISPR/Cas system is originally a prokaryotic immune system that confers resistance to foreign genetic elements such as those present within plasmids and phages that provides a form of acquired immunity. RNA harboring the spacer sequence helps Cas (CRISPR associated) proteins recognize and cut exogenous DNA. Other RNA-guided Cas proteins cut foreign RNA. A simple version of the CRISPR/Cas system, CRISPR/Cas9, has been modified to edit genomes. By delivering the Cas9 nuclease complexed with a synthetic guide RNA (gRNA) into a cell, the genome of the cell can be cut at a desired location, allowing existing genes to be removed and/or new ones added.

There is also a CRISPR system from Streptococcus pyogenes that relies on the protein Cas9. The Cas9 endonuclease is a four-component system that includes two small RNA molecules named CRISPR RNA (crRNA) and trans-activating CRISPR RNA (tracrRNA). It was shown that Cas9 from the S. thermophilus CRISPR system can be reprogrammed to target a site of their choosing by changing the sequence of its crRNA. Accordingly, the present invention also relates to the method of the invention, wherein the disruption of B2M and/or insertion of the immunomodulatory protein is/are mediated by engineered nucleases and wherein the engineered nuclease is CRISPR/Cas9. In this method, the crRNA may be selected from the group consisting of ACTCACGCTGGATAGCCTCC (SEQ ID NO: 2), GAGTAGCGCGAGCACAGCTA (SEQ ID NO: 3) and GGCCGAGATGTCTCGCTCCG (SEQ ID NO: 4). The Cas9 endonuclease of Streptococcus pyogenes requires a proto-spacer adjacent motif" (PAM) in the crRNA 3' to the recognition sequence to enable the binding to this specified DNA sequence. This PAM has the consensus sequence XGG, wherein X can be any nucleic acid. Accordingly, SEQ ID NOs: 2-4 may additionally have the sequence XGG at the 3' prime end, wherein X can be any nucleic acid. Accordingly, the crRNA may also be ACTCACGCTGGATAGCCTCCAGG (SEQ ID NO: 5), GAGTAGCGCGAGCACAGCTAAGG (SEQ ID NO: 6) and GGCCGAGATGTCTCGCTCCGTGG (SEQ ID NO: 7).

To determine whether a pluripotent stem cell is deficient of MHC class I molecules lies within the abilities of a person skilled in the art. The analysis may be performed on the level of the genome, transcription and/or translation. E.g., when the deficiency of MHC class I molecules was achieved by disrupting a gene that is essential for forming a MHC class I molecule such as the B2M gene by nucleases such as CRIPSR, mutations preventing the expression of a functional B2M protein within the B2M gene can be analyzed by sequencing of the respective nucleotide sequence. Examples for sequencing technologies include Sanger sequencing and next generation sequencing such as single-molecule real-time sequencing (Pacific Biosciences), Ion semiconductor (Ion Torrent sequencing), Pyrosequencing, Sequencing by synthesis (Illumina), Sequencing by ligation (SOLiD sequencing) and nanopore sequencing. Alternatively, a PCR with primers binding in the region to be mutated or a Southern Blot analysis could be performed. The transcription of a gene encoding for at least a part of the MHC class I molecule can e.g. be analyzed by quantitative PCR making use of a primer pair that spans the region to be mutated. Finally, analysis of the protein expression or translation may be performed. Exemplary methods to analyze whether a pluripotent stem cells is deficient of MHC class I molecules may thus include immunoassays such as Western Blot, flow cytometry, surface plasmon resonance and the like.

The present invention also relates to a nucleic acid comprising at least one of the sequences of SEQ ID NOs: 2-7. In one embodiment, the nucleic acid may be operably linked to an expression control sequence which allows overexpression of the nucleic acid in a host cell. Exemplary expression control sequences include a promoter, such as a U6 promoter or a CMV promoter. The nucleic acid of the present invention may also be comprised in a vector. The vector may further encode a transactivating crRNa (tracrNA) and/or a Cas9 nuclease. The present invention also relates to the use of the nucleic acid or the vector of the invention for disrupting B2M.

The term "non-immunogenic" as used herein refers to a tissue that essentially does not elicit an immune response, i.e. a tissue that is not rejected by a recipient. Further characteristics of a non-immunogenic engineered tissue may include that the tissue is not recognized as allogenic by effector T cells, and/or does not bind anti-HLA antibodies and/or is resistant to NK-mediated (natural killer cells) lysis. Assays to examine these characteristics are well known to a person skilled in the art and are exemplified in Gornalusse et al. (2017), Nature Biotechnology, 35(8):765-772 and WO 2012/145384.

The recognition of the tissue as being allogenic by effector T cells and the resistance towards NK-mediated lysis may be, e.g., analyzed by performing a chromium release assay with NK cells. Such an assay is based on a exposure of the tissue or cell that is to be analyzed to $^{51}$Cr, subsequent contacting of the tissue or cell with CD8$^+$ T cells or NK cells and a final measurement of the radioactivity in the supernatant by scintillation (see again e.g. Gornalusse et al (2017), Nature Biotechnology, 35(8):765-772 and WO 2012/145384).

The term "Effector T cells" as used herein relates to the various T cell types that actively respond immediately to a stimulus, such as co-stimulation. This includes helper and killer T cells. T helper cells (TH cells) assist other white blood cells in immunologic processes, including maturation of B cells into plasma cells and memory B cells, and activation of cytotoxic T cells and macrophages. These cells are also known as CD4$^+$ T cells because they express the CD4 glycoprotein on their surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. Cytotoxic T cells (TC cells, CTLs, T-killer cells, killer T cells) destroy virus-infected cells and tumor cells, and are also implicated in transplant rejection. These cells are also known as CD8$^+$ T cells since they express the CD8 glycoprotein at their surfaces. These cells recognize their targets by binding to antigen associated with MHC class I molecules, which are present on the surface of all nucleated cells. Through IL-10, adenosine, and other molecules secreted by regulatory T cells, the CD8+ cells can be inactivated to an anergic state, which prevents autoimmune diseases.

The binding of anti-HLA antibodies, preferably anti-HLA-A or anti-HLA-B antibodies, to the tissue of the invention relates to the complement-dependent cytotoxicity (CDC). Cells expressing a HLA-A or HLA-B molecule are prone to detection by anti-HLA-A or anti-HLA-B. In an environment that includes all components of the complement system and anti-HLA-A and/or anti-HLA-B antibodies, tissues expressing HLA-A and/or HLA-B on their surface are killed by the complement system if their HLA is not compatible with that of the recipient. Such tissues are likely to be rejected in a recipient. An example for such an assay can again be found in Gornalusse et al. (2017), Nature Biotechnology, 35(8):765-772.

An "immunomodulatory protein" as described herein refers to any protein, which is able to prevent an immune reaction targeted against the engineered tissue. In context with a missing functional B2M on the cell surface, the cells of the engineered tissue do not present any MHC I molecule on their surface, which is a "missing self"-signal leading to their destruction by the immune system of a recipient, mainly due to the actions of natural killer cells. Suitable immunomodulatory genes include without limitation a gene encoding a viral protein that inhibits antigen presentation, and preferably a gene that encodes a single chain (SC) fusion human leukocyte antigen (HLA) class I protein as described herein. The immunomodulatory protein of the invention may be recombinant and/or not naturally-occurring in the pluripotent stem cell. Accordingly, the pluripotent stem cell may express a recombinant immunomodulatory protein.

A fusion protein of a SC-HLA class I fusion protein used in the invention may be expressed by the pluripotent stem cells and/or the cells forming the engineered tissue. The advantage of the fusion protein is that a functional HLA class I protein may be presented on the cell surface of the cells of the engineered tissue without the need to express B2M, which would also associate with other HLA monomers, which then would again induce a rejection reaction. While the cells used in the present invention lack expression of functional B2M, such a SC-HLA class I fusion protein may comprise, in accordance with the disclosure of Gornalusse et al. (2017), Nature Biotechnology, 35(8):765-772 (see, for example, FIG. 1 thereof) a portion of B2M covalently linked to at least a portion of an HLA class Iα chain selected group consisting of HLA-A, HLA-B, HLA-C, HLA-E, HLA-F and HLA-G. In one embodiment, the single chain fusion HLA class I protein comprises (at least) a portion of B2M and at least a portion of HLA-A. In one embodiment, the single chain fusion HLA class I protein comprises at least a portion of B2M and at least a portion of HLA-A0201 (see also WO 2012/145384 in this respect). In one embodiment, the single chain fusion HLA class I protein comprises at least a portion of B2M and at least a portion of HLA-E. In one embodiment, the single chain fusion HLA class I protein comprises at least a portion of B2M and at least a portion of HLA-G. In one embodiment, the single chain fusion HLA class I protein comprises at least a portion of B2M and at least a portion of HLA-B. In one embodiment, the single chain fusion HLA class I protein comprises at least a portion of B2M and at least a portion of HLA-C. In one embodiment, the single chain fusion HLA class I protein comprises at least a portion of B2M and at least a portion of HLA-F. In one embodiment, the immunomodulatory protein is a fusion protein of B2M and HLA-E and/or comprises SEQ ID NO: 18. A vector for the expression of a fusion protein of B2M and HLA-E may comprise SEQ ID NO: 17.

The pluripotent stem cell may further express a target peptide antigen that is presented by the single chain fusion HLA class I protein on the cell surface. Such a target peptide antigen may stabilize the HLA class I protein and may also strengthen the "self"-signal. In certain particular embodiments, the target peptide antigen is covalently linked to the single chain fusion HLA class I protein. The HLA-E single-chain dimer may consist of an HLA-E heavy chain covalently fused to B2M through a flexible $(G_4S)_4$ linker, such that it can bind a normal repertoire of peptides for antigen presentation (cf., for example, FIG. 1C of Gornalusse et al. (2017), Nature Biotechnology, 35(8):765-772). Such an HLA-E dimer is exemplified in SEQ ID NO: 18. The "HLA-E dimer" may bind different or "normal" peptides for antigen presentation. However, additionally or alternatively, a peptide may be fused to the HAL-E dimer. As an illustrative example, the HLA-E single-chain trimer may contain an additional $(G_4S)_3$ linker fused to a peptide comprising the sequence VMAPRTLFL (SEQ ID NO: 1) derived from the signal sequence of HLA-G (another HLA class I molecule), which is a non-polymorphic peptide normally presented by HLA-E that inhibits NK cell-dependent lysis through its binding to CD94/NGK2A. In one embodiment, the immunomodulatory protein is a fusion protein of the target peptide antigen VMAPRTLFL (SEQ ID NO: 1) fused via a $(G_4S)_3$ linker to a fusion protein of B2M and HLA-E and/or comprises SEQ ID NO: 20.

For CRISPR-mediated Knock-In of a gene sequence, the homologous recombination DNA repair system of the host cell may be exploited. Here, a nucleic acid comprising the sequence to be inserted is flanked by "homology arms" may be introduced into the host cell simultaneously with the CRISPR/Cas9 nuclease and the crRNA. The nuclease may then induce a double-strand break, which may be repaired by the host cell's DNA repair system. In case of homologous recombination, the DNA repair system uses a homologous sequence, usually the second allele. By introducing the nucleic acid comprising the homology arms, the_DNA repair system of the host cell uses the introduced nucleic acid as template instead of the second genomic allele and thereby integrates the sequence to be inserted. "Homology arms" as used herein relate to nucleic acid sequences, whose DNA sequence is identical to the target genome sequence. Typically, the gene sequence to be inserted is flanked by one homology arms each on the 3' and the 5' end. The "left" homology arm, i.e. the homology arm 3' of the sequence to be inserted, may have a sequence as shown in SEQ ID NO: 22 or 23. The "right" homology arm, i.e. the homology arm 5' of the sequence to be inserted may have a sequence as shown in SEQ ID NO: 24. These exemplified homology arms mediate an integration into the human B2M gene (see also FIG. 5A).

The gene sequence to be inserted that me be flanked by one homology arm on each the 3' and the 5' end and that encodes the HLA-E dimer or HLA-E trimer may include further elements that may facilitate the expression and/or function. These additional elements include, but are not limited to, a T2A self-cleaving peptide, e.g. as depicted in SEQ ID NO: 25, a B2M targeting signal, e.g. as depicted in SEQ ID NO: 26 or a pBHGA element (SEQ ID NO: 27).

An exemplary vector for the integration of the HLA-E dimer may comprise SEQ ID NO: 17 (comprising a fusion protein of B2M and HLA-E) and of the HLA-E trimer (comprising a fusion protein of target peptide antigen, $(G_4S)_3$ linker, B2M and HLA-E) may comprise SEQ ID NO: 19. Both, SEQ ID NO: 17 and 19 comprise homology arms that are directed to integration into the B2M gene, which is knocked-out as described herein. All the exemplified vectors for integration comprise all additional elements as described herein.

Various tissues may be produced with the method of the invention. Examples include, but are not limited to, heart tissue, liver tissue, kidney tissue, brain tissue, pancreatic tissue, lung tissue, muscle tissue, gastrointestinal tissue, neuronal tissue, skin tissue, bone tissue, bone marrow, fat tissue, connective tissue or blood vessel tissue. Exemplary methods to differentiate pluripotent stem cells to a cell type that is essential for the function of the engineered tissue under conditions that optionally also allow the formation of the engineered tissue can be found in the following example section. Differentiation of the pluripotent stem cells and the formation of the engineered tissue may take place at the same time or the differentiation can be performed before the formation begins.

Different approaches to produce engineered tissues are known to a person skilled in the art. The following technologies may, for example, be used in the present invention: 1) Tissue engineering: cells differentiated from pluripotent stem cells are mixed at defined ratios in a hydrogel environment, see e.g. Tiburcy et al. (2017), Circulation, 135: 1832-1847; 2) Organoid technologies: starting material are typically undifferentiated pluripotent stem cells (HES, iPSC or PaSC), which are either aggregated to so called micro tissues (see Ewart et al. (2018), Annu Rev Pharmacol Toxicol, 58:65-82), which may in principle further be fused to macro tissues or embedded in a hydrogel/matrix environment (see Lancaster et al. 2013, Nature, 501:373-379 and WO2015/040142); 3) 3D printing: 3D printing of tissues, in the end similar to cast molding technologies (see also Sudo (2014), Organogenesis, 10(2):216-224; Tiburcy et al. (2017), Circulation, 135:1832-1847); 4) Recellularization of decellularized organs: the concept is to use porcine organs to recellularize for human use (see also Ott et al. (2008), Nature medicine, 14(2):213-221 for heart, but the concept is tried for many other organs; 5) Cell sheet technology: basically, several monolayers of cells are stacked and form an organ (see e.g. Shimizu et al. (2002), Circ Res 90:e40-e48; Sawa et al. (2015), Circ J 79:991-999).

Turning to the production of functional heart tissue as a first illustrative example, International Patent Application WO 2015/040142 (herein termed "bioengineered heart muscle") discloses a method to produce engineered heart tissue from pluripotent stem cells. The conditions described in WO 2015/040142 are thus, with respect to the formation of functional heart tissue, conditions to obtain pluripotent stem cells that have been differentiated into said at least one cell type that is essential for the function of the engineered tissue. These conditions described in WO 2015/040142 may with respect to the formation of functional heart tissue, also be seen as conditions for differentiation of the pluripotent stem cells into a cell type that is essential for the function of the engineered tissue that also allow the formation of the engineered tissue. Accordingly, for the formation of engineered heart tissue the method of the invention may comprise the following steps: (i) cultivating the pluripotent stem cells in a basal medium comprising an effective amount of (a) BMP4, Activin A, FGF2, a GSK3-inhibitor, and (b) a serum-free supplement resulting in a final concentration of 0.5-50 mg/ml albumin, 1-100 µg/ml transferrin, 0.1-10 µg/ml ethanol amine, 0.003-0.3 µg/ml sodium selenite, 0.4-40 µg/ml L-Carnitine HCl, 0.1-10 µg/ml Hydrocortisone, 0.05-5 µl/ml Fatty acid supplement, 0.0001-0.1 µg/ml triodo-L-thyronine (T3), thereby inducing mesoderm differentiation of the pluripotent stem cells; (ii) cultivating the cells obtained in step (i) in a basal medium comprising an effective amount of an inhibitor of the Wnt-signaling pathway and a serum-free supplement as in (i), thereby inducing cardiac differentiation of the cells; and (iii) cultivating the cells obtained in step (ii) in a basal medium comprising an effective amount of a serum-free supplement as in (i), under mechanical stimulation, thereby promoting cardiac maturation. In this context, see also Example 2 of the Examples Section of the present application. Other publications that relate to the generation of heart tissues and that provide conditions for differentiation of the pluripotent stem cells into a cell type that is essential for the function of the engineered tissue and that optionally also allow the formation of the engineered (heart) tissue include, but are not limited to, Ogle et al. (2016), Sci Trans Med, 8(342), 1-7; Tiburcy et al. (2017), Circulation, 135:1832-1847; Ye et al. (2013), Cir Res, 113:922-932; Zimmermann (2009), Antioxidant & Redox Signaling, 11(8):2011-2023; Ott et al. (2008), Nature Medicine, 14(2):213-221; or Shimizu et al. (2002), 90:e40-e48. Differentiation of the pluripotent stem cells and the formation of the engineered tissue may take place at the same time or the differentiation can be performed before the formation begins. The cardiomyocytes obtained by the method of WO 2015/040142 may subsequently be processed by the method of producing engineered heart tissue (also known as engineered heart muscle (EHM)) that is described in International Patent Application WO 2015/025030. Accordingly, the method of the invention may further comprise (iv) providing a serum-free reconstitution mixture in one or more moulds, said reconstitution mixture comprising (a) a serum-free minimum essential medium; (b) a serum-free supplement resulting in a final concentration of 0.5-50 mg/ml albumin, 1-100 µg/ml transferrin, 0.1-10 µg/ml ethanol amine, 0.003-0.3 µg/ml sodium selenite, 0.4-40 µg/ml L-Carnitine HCl, 0.1-10 µg/ml Hydrocortisone, 0.05-5 µl/ml Fatty acid supplement, 0.0001-0.1 µg/ml triodo-L-thyronine (T3) and 0.2-2 mg/ml collagen; and (c) the cells obtained in step (iii) and a cell type that forms part of the engineered tissue, preferably human non-myocytes, optionally derived from the pluripotent stem cells, wherein 20 to 80% of the total cell mixture are the cells obtained in step (iii); wherein the reconstitution mixture has a pH of 7.2 to 7.6; (v) culturing the serum-free reconstitution mixture in said one or more moulds, whereby the serum-free reconstitution mixture is allowed to condense for at least 15 min; (vi) culturing the mixture obtained in step (v) in said one or more moulds in a serum-free EHM culture medium until the mixture condenses to at least 50% of its original thickness, wherein said EHM culture medium comprises (a) a basal medium comprising 0.5-3 mmol/L $Ca^{2+}$; (b) a serum-free supplement as defined in (i)(b); (c) 0.5-10 mmol/L L-glutamine; (d) 0.01-1.0 mmol/L ascorbic acid; (e) 1-100 ng/ml IGF-1; and (f) 1-10 ng/ml TGFβ1; (vii) culturing the mixture obtained in step (iii) under mechanical stretching in a serum-free EHM culture medium as defined in step (iii) (a)-(f), whereby force-generating engineered heart tissue is formed. This engineered heart tissue is also known as engineered heart muscle (EHM) Alternatively, the method of WO 2015/040142 can be carried out with the pluripotent stem cells of the invention, wherein the pluripotent stem cells have colonized a hydrogel such as Collagen type I before. This approach leads to the generation of a so-called bioengineered heart muscle (BHM) that may be described as an organoid.

A person skilled in the art is also aware of producing other engineered tissues such as liver tissue, kidney tissue, brain tissue, pancreatic tissue, lung tissue, muscle tissue, gastrointestinal tissue, neuronal tissue, skin tissue, bone tissue, bone marrow, fat tissue, connective tissue or blood vessel tissue under conditions for differentiation of the pluripotent stem cells into a cell type that is essential for the function of the engineered tissue that optionally also allow the formation of the engineered tissue. Differentiation of the pluripotent stem cells and the formation of the engineered tissue may take place at the same time or the differentiation can be performed before the formation begins. Examples of such conditions for the generation of liver tissues are disclosed in WO 2013/047639 or Sudo (2014), Organogenesis, 10(2): 216-224. Examples for suitable conditions the generation of kidney tissues are disclosed in Morizane et al. (2017), Stem Cells, 35:2209-2217. Examples for suitable conditions for the generation of brain tissue or neuronal tissue are disclosed in Yang et al. (2011), Cell Stem Cell 9:517-525 or Lancaster et al. (2013), Nature, 501:373-379 (see also Example 4 of the present application). Examples for suitable conditions for the generation of pancreatic tissues are disclosed in Pagliuca et al. (2014), Cell, 159:428-439 (see also Example 6 of the present application). Examples for the generation of functional skeletal muscle tissues are disclosed in Rao et al. (2018), Nature Communications, 9(126):1-12 (see also Example 5 of the present application). Examples of suitable conditions for the generation of blood vessel tissues are disclosed in Song et al. (2018), Cell Stem Cell, 22:340-354, for instance. Finally, examples for suitable conditions for the generation of retina tissues are, for instance, described in Llonch et al, Developmental Biology 433 (2018) 132-143.

Many biological tissues do not only comprise one single cell type. E.g., heart muscle comprises cardiomyocytes and in cell abundance a larger non-myocytes component comprising mainly fibroblasts and endothelial cells. While the cardiomyocytes are the cell type that is essential for the function of the tissue, i.e. for the heartbeat, the fibroblasts provide extracellular matrix that stabilizes the tissue, i.e. can be seen as cells that form part of the tissue. Endothelial and smooth muscle cells are involved in the hearts vasculature. Accordingly, the method of the present invention may further comprise inducing the differentiation of the pluripotent stem cells into at least one second cell type, wherein the second cell type forms part of the engineered tissue. The cells that are essential for the function of the tissue and the cells that form part of the tissue can be combined after differentiation to form an engineered tissue. Such a method is e.g. described in WO 2015/025030. Here, human cardiac myocytes and human non-myocytes, such as fibroblasts, endothelial cells, smooth muscle cells or mesenchymal stem cells are examples for cells that form part of the tissue and cardiomyocytes are the cells that are essential for the function of the tissue. By using the same pluripotent stem cells as source for the cells that are essential for the function of the tissue and for the (second) cells that form part of the tissue, the cells have the same genetic modifications, i.e. lack B2M and express an immunomodulatory protein on the cell surface, rendering the combined engineered tissue non-immunogenic.

The present invention not only relates to methods of producing a non-immunogenic engineered tissue but also relates to a non-immunogenic engineered tissue itself. Accordingly, the present invention relates to an engineered tissue comprising, a cell type that is essential for the function of the engineered tissue, wherein said cell type has been obtained by differentiating pluripotent stem cells into said cell type under conditions suitable for differentiation of the pluripotent stem cells into said type, wherein the pluripotent stem cells are deficient of MHC class I molecules and comprise an immunomodulatory protein on their surface, thereby rendering the engineered tissue to be non-immunogenic to a recipient of the engineered tissue. The present invention also refers to an engineered tissue obtainable by the method of the invention. In one such embodiment, the present invention relates to a engineered tissue, comprising pluripotent stem cells, the pluripotent stem cells being deficient of MHC class I molecules and comprising an immunomodulatory protein on their surface, wherein the pluripotent stem cells are differentiated into a cell type that is essential for the function of the engineered tissue under conditions that also allow the formation of the engineered tissue, thereby rendering the engineered tissue to be non-immunogenic to a recipient of the engineered tissue.

The engineered tissue may further comprise an extracellular matrix material. The extracellular matrix (ECM) is a collection of extracellular molecules secreted by support cells that provides structural and biochemical support to the surrounding cells. Because multicellularity evolved independently in different multicellular lineages, the composition of ECM varies between multicellular structures; however, cell adhesion, cell-to-cell communication and differentiation are common functions of the ECM. The extracellular matrix includes the interstitial matrix and the basement membrane. Interstitial matrix is present between various cells (i.e., in the intercellular spaces). Gels of polysaccharides and fibrous proteins fill the interstitial space and act as a compression buffer against the stress placed on the ECM. Basement membranes are sheet-like depositions of ECM, which surround for example cardiomyocytes and endothelial cells for anchorage within the tissue and to enable communication with the extracellular environment. Each type of tissue has a particular type of ECM: collagen fibers and bone mineral comprise the ECM of bone tissue; reticular fibers and ground substance comprise the ECM of loose connective tissue; and blood plasma is the ECM of blood. The main ECM components of the heart are collagen type I and III with further contribution of and hyaluronic acid as well as laminin, collagen type IV, proteoglycans, fibronectin, and nidogen, the latter being key components of the basal membranes. Collagen type I is the most abundant ECM material and thus a preferred material in tissue engineering and bioengineering. Thus, the extracellular matrix biomaterial preferably is Collagen type 1. In one embodiment, the tissue formation is carried out in the presence of a hydrogel, preferably an extracellular matrix protein containing hydrogel such as a fibrin hydrogel or a collagen hydrogel, and most preferably a collagen hydrogel.

The ECM material may also comprise materials, which normally are not part of a naturally occurring ECM. Such non-naturally occurring ECM material preferably is biocompatible, i.e. is not toxic and does not induce an immune response. Examples for such non-naturally occurring ECM material include, but are not limited to, alginate, a hydrogel, or synthetic matrices such as polylactic acid, polyglycolic acid, and polyglycerol sebacate (biorubber), and poly(octamethylene maleate (anhydride) citrate.

The engineered tissue may also have the same properties as the product of the method of the invention. Preferably, the engineered tissue is not recognized as allogenic by $CD8^+$ T cells, does not bind anti-HLA antibodies and/or is resistant to NK-mediated lysis. Such an engineered tissue may replace at least a part of a damaged tissue in a subject. Preferably, the engineered tissue does not bind anti-HLA-A or anti-HLA-B antibodies.

The present invention further relates to a pharmaceutical composition that contains the engineered tissue of the invention. The pharmaceutical composition may also contain materials such as buffers to stabilize the engineered tissue.

The engineered tissue or the pharmaceutical compositions of the invention are useful in the treatment of various diseases. It is particularly preferred for use in the treatment of diseases that are characterized by failure or dysfunction of a tissue. However, the present invention relates also to the engineered tissue or the pharmaceutical composition of the invention for use in a method of treatment of a disease condition. The present invention also relates to a method of treating a disease condition, comprising administering b a subject in need thereof an effective amount of the engineered tissue or the pharmaceutical composition of the invention.

As pluripotent stem cells carry the risk of forming teratoma, the engineered tissue preferably does not contain any pluripotent stem cells, particularly if the engineered tissue of the invention is for therapeutic applications.

The disease condition may, for example, be diabetes, an autoimmune disease, cancer, an infectious disease, a heart disease such as myocardial infarction or heart failure, a skeletal or joint condition, muscle dystrophy, osteogenesis imperfecta, a burn, liver failure, kidney failure, brain damage, or soft tissue damage. Here, the engineered tissue may replace tissues that have been affected or destroyed by autoimmune reactions, trauma, insufficient blood supply, or a burn to name only a few illustrative examples.

The present invention further relates to the use of the engineered tissue of the invention in an in vitro model for drug toxicity screening and/or as a research tool. In this regard, the engineered tissue could serve for example as a surrogate of organs or tissues of humans to avoid using animal models.

A better understanding of the present invention and of its advantages will be available from the following examples, offered for illustrative purposes only. The examples are not intended to limit the scope of the present invention in any way.

EXAMPLES

Example 1: Generation of Pluripotent Stem Cells being Deficient of MHC Class I Molecules and Comprising an Immunomodulatory Protein on their Surface Knock Out of β2-Microglobulin (B2M)

Pluripotent stem cell line 50039 was obtained from the NINDS Human Cell and Data Repository. This cell line is also available from Lonza and was characterized in Baghbaderani et al. (2015), Stem Cell Reports, 5:647-6659. Baghbaderani et al. also disclose standard conditions for maintain this cell line. Differing from this, the pluripotent cells were maintained in StemMACS™ iPS-Brew medium. For the provision of an extracellular matrix, CTG Laminin-521 (Biolamina) or Geltrex (Thermo Scientific) was used.

To disrupt all copies of the B2M gene, the Alt-R® CRISPR/Cas technology of Integrated DNA Technologies was used according to the instructions of the manufacturer. Depending on the sequence of the CRISPR-Cas9 crRNA, the Alt-R Cas9 nuclease is capable of specifically introducing double strand breaks, which may result in non-homologous end joining, which eventually introduces mutations that disrupt the function of the gene. Three different crRNA were used: ACTCACGCTGGATAGCCTCC (SEQ ID NO: 2), GAGTAGCGCGAGCACAGCTA (SEQ ID NO: 3) and GGCCGAGATGTCTCGCTCCG (SEQ ID NO: 4). FIG. 1A shows an overview of the B2M gene surrounding Exon 1 and the binding sites of the different crRNAs (underlined). All three crRNAs were designed to bind close to the region that will form the N-terminus of the B2M translation product of the B2M gene. Using one of these crRNA, the Alt-R Cas9 nuclease and the Alt-R Cas9 electroporation enhancer, a ribonucleoprotein complex is formed, which was electroporated into the PSC. For each of the different crRNA, the crRNA:tracRNA:Cas9 RNP complex was prepared according to the instructions of the manufacturer. The crRNA:tracRNA:Cas9 RNP complex was transfected into the PSC using a Lonza 4D nucleofector system (X-unit) and P3 solution kit (Lonza, V4XP-3012) using the program CB-150. After transfection, PSCs were plated and cultured until colonies appeared. Individual colonies were picked by hand and passage using standard protocols. Genome editing was confirmed by sequencing. From 60 sequenced colonies, 15 showed mutations within exon 1 of B2M.

Table 1 shows an overview of the results. Only 4 colonies were confirmed to be clonal (clones 3, 18, 20, and 34). As shown in FIG. 2, the genome edited resulted in a frame shift in one (clone 3) or two alleles (clones 18, 20 and 34).

TABLE 1

Summary of sequencing results.

| Clone | Result |
| --- | --- |
| B2M-#001 | 4 sequences w/o WT, resolving not possible, mixed clone |
| B2M-#002 | 1 bp deletion, homo, low (mut) background seq |
| B2M-#003 | 1 bp insertion, hetero |
| B2M-#004 | 4 sequences w/o WT, resolving not possible, mixed clone |
| B2M-#005 | 3 sequences w/o WT, resolving not possible, mixed clone |
| B2M-#016 | 3 sequences w/o WT, resolving not possible, mixed clone |
| B2M-#017 | 3 sequences w/o WT, mixed clone |
| B2M-#018 | 13 bp deletion, 1 bp deletion, compound hetero |
| B2M-#019 | 3 sequences w/o WT, resolving not possible, mixed clone |
| B2M-#020 | 1 bp deletion, homo |
| B2M-#031 | 3 bp deletion and 34 bp deletion, compound hetero |
| B2M-#032 | 4 sequences with WT, resolving not possible, mixed clone |
| B2M-#033 | WT and mut in background, resolving not possible, mixed clone |
| B2M-#034 | 2 bp insertion, homo |
| B2M-#035 | 3 sequences w/o WT, resolving not possible, mixed clone |

Clones 3, 18, 20 and 34 showing successful deletion are highlighted in bold and underlining.

A FACS analysis of clones 3, 18, 20 and 34 and comparison to wild type iPSC cell line 50039 was performed (FIG. 3). Here the expression of B2M (APC-labeled anti-human B2M, Biolegend) and HLA-A,B,C (PE-labeled anti-human HLA-,B,C, Biolegend) was analyzed. As can be seen from FIG. 3, wildtype and the heterozygous clone 3 show HLA and B2M on the cell surface, both unstimulated and after 24 h stimulation with interferon γ. The three other clones 18, 20 and 34, which comprise a mutation on both alleles, do not show any HLA and B2M on their cell surface even after 24 h stimulation with interferon γ, thereby confirming that all clones are suitable starting cells for the knock in of a HLA fusion protein as described in the following.

Knock in of HLA-E Fusion Protein

The knock in of the HLA-E fusion protein may be performed analogous to International Patent Application WO 2012/145384 starting from any of the clones 18, 20 and 34 described above. Using an integrating foamy virus vector, the single chain B2M/HLA-E fusion protein may be expressed in human PSC. The foamy virus vector may include an expression cassette with a promoter driving a B2M/HLA-E single chain fusion construct ("dimer"). The B2M/HLA-E single chain fusion protein ("dimer") may have an amino acid sequence as depicted in SEQ ID NO: 18. The vector for integration of the dimer may comprise SEQ ID NO: 17. A trimeric single chain fusion construct may additionally include a covalently attached HLA-G peptide MAPRTLFLGGGGSGGGGSGGGGSIQRTPK (SEQ ID NO: 21) ("trimer"). The vector for integration of the trimer may comprise SEQ ID NO: 19. Clones overexpressing a B2M/HLA-E fusion protein may be isolated by the use of flow cytometry with an antibody binding the fusion protein.

Such an approach was performed here. B2M KO TC1133 hIPSC Clone #34 in which Crispr/Cas9 targeting resulted with 2 bp (CT) insertions in both alleles creating a frame shift in the gene expression was selected as the parental B2M KO line to knock-in HLA-E gene.

Figure 5:
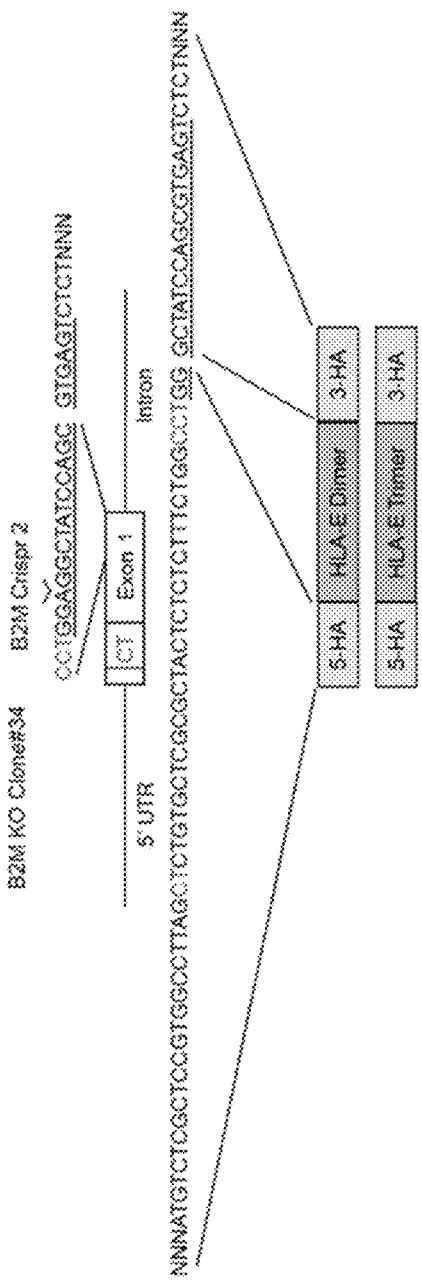
FIGS. 5A-C depict the generation of an HLA-E KI TC1133 hIPSC line.
Figure 5:
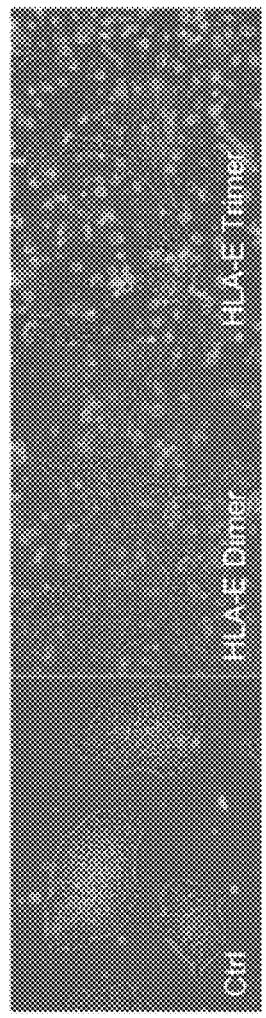
Figure 5:
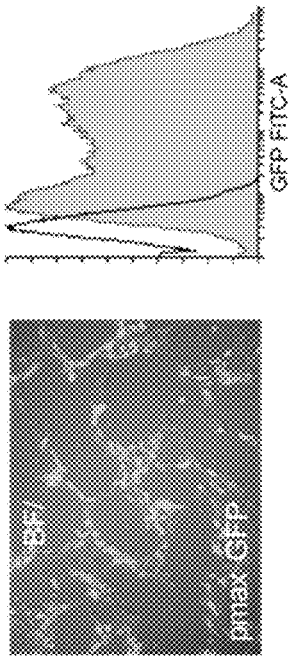

Having the proof of concept that the B2M gene can also be successfully targeted with B2M Crispr 2/Cas9, exon 1 region in B2M KO Clone #34 was next targeted herein with B2M Crispr 2/Cas9 and the donor plasmid containing HLA-E-Dimer (SEQ ID NO: 17) and HLAE-Trimer (SEQ ID NO: 19) sequences with homology arms designed according to the modified genomic sequence of the KO line as described (FIG. 5A). A relatively higher cell death was observed after electroporation as expected when compared to untreated wild-type cells. However, hIPCSs retained their proper morphology (FIG. 5B). More than 80% transfection efficiency was obtained as demonstrated by flow cytometry analysis of GFP+ cells in parallel transfected with pmaxGFP plasmid (FIG. 5C).

Figure 6:
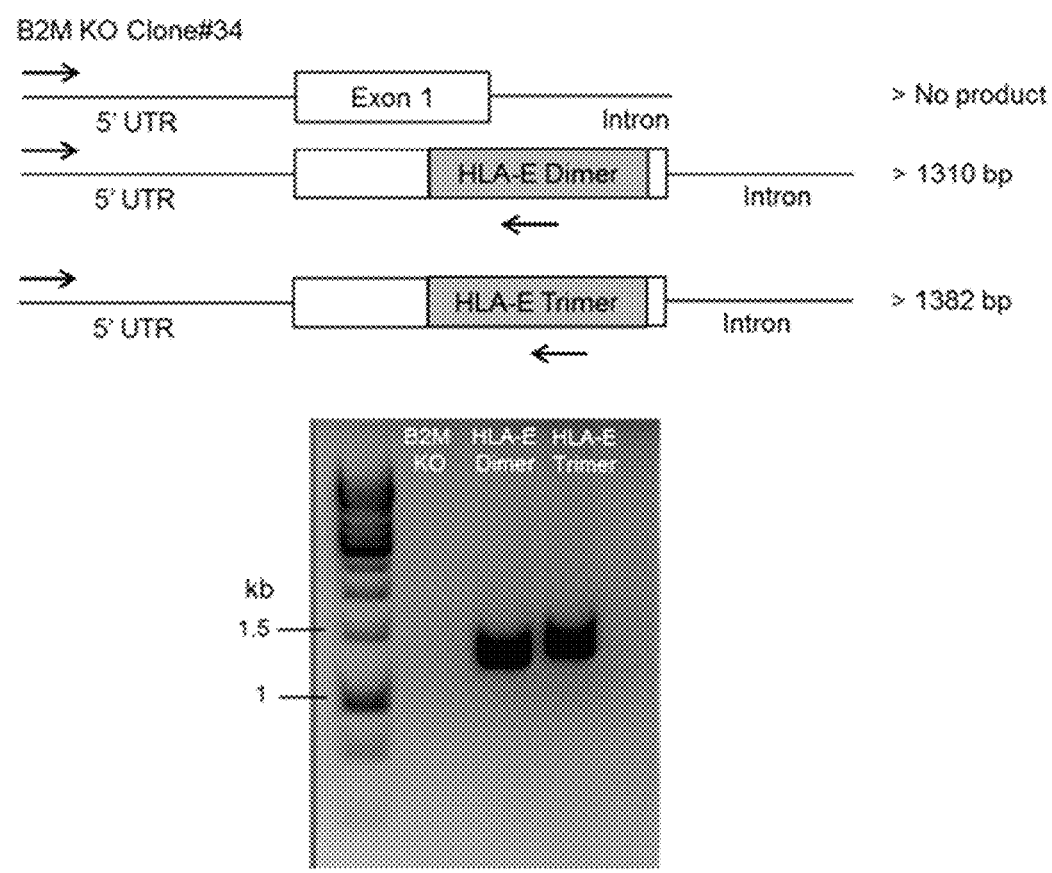
FIGS. 6A-C depicts the Knock-in of HLA-E upstream in B2M locus.
Figure 6B:
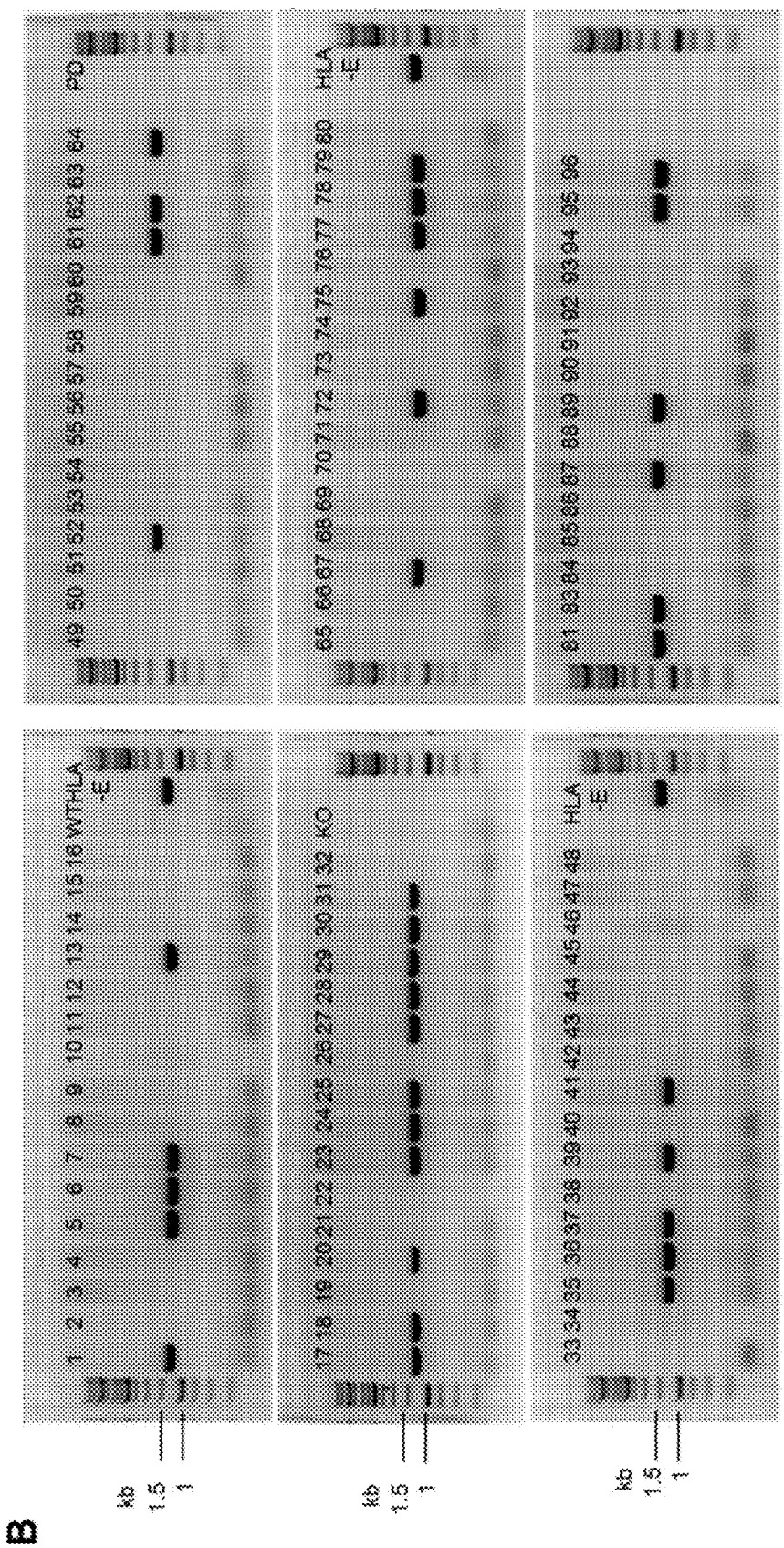
Figure 6C:
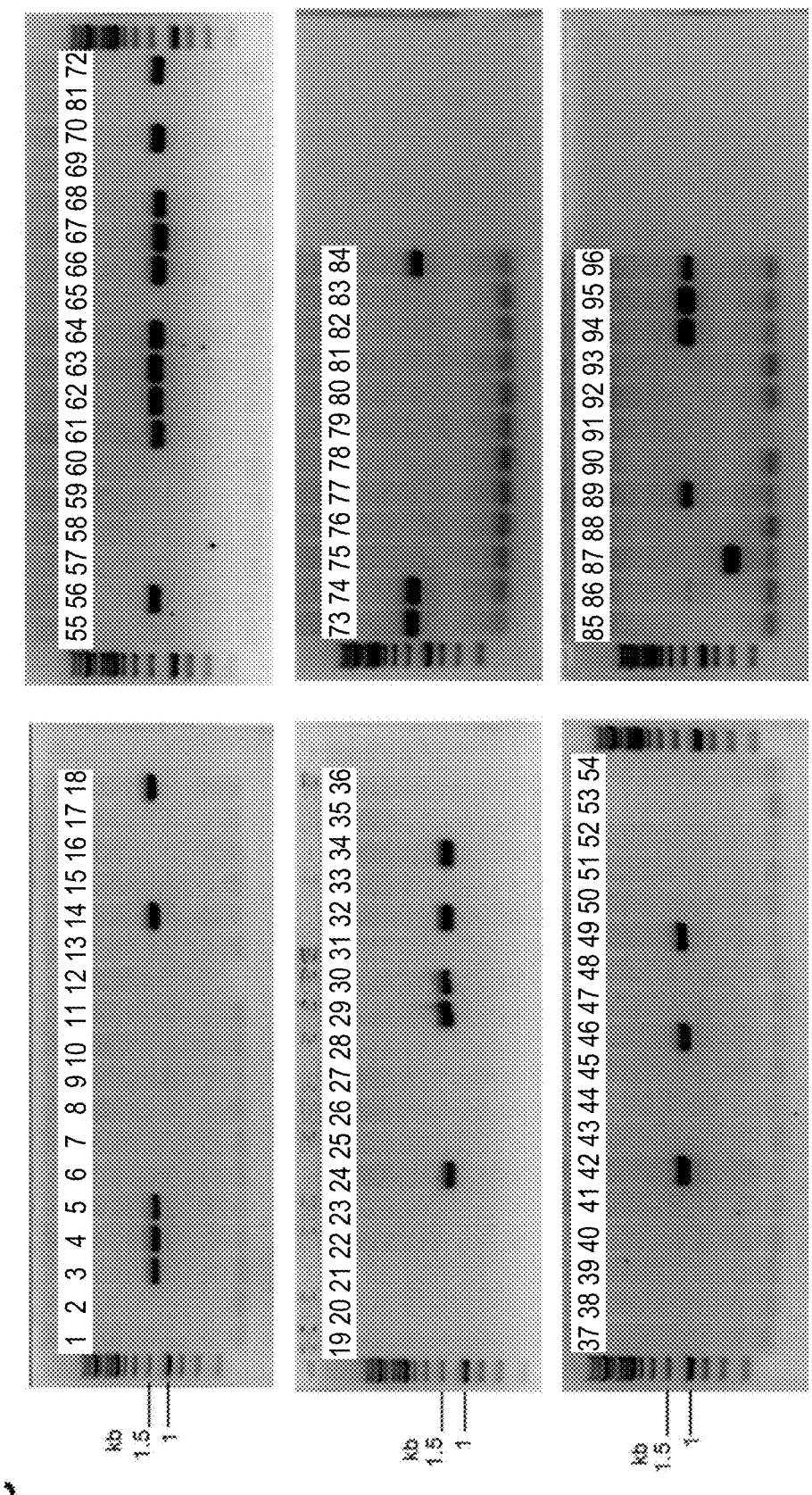

Characterization of HLA-E KI hIPSC Clones hIPSCs transfected with HLA-E Dimer and Trimer plasmids were seeded in single cells into a 96-well plate for colony formation. In addition, genomic DNA from transfected hIPSC pools were simultaneously isolated. Next, PCR was performed with the primers inside 5'-homology arm and donor sequence as demonstrated (FIG. 6A). Expectedly, no product was detected in the parental B2M KO line, while the corresponding regions were specifically amplified in the transfected pools indicating for successful gene integration in the B2M locus (FIG. 6A). Given the preliminary data, up to hundred clones were screened, and around fifty out of them were found to be positive for the upstream of both HLA-E Dimer (FIG. 6B) and Trimer integration (FIG. 6C).

Figure 7A:
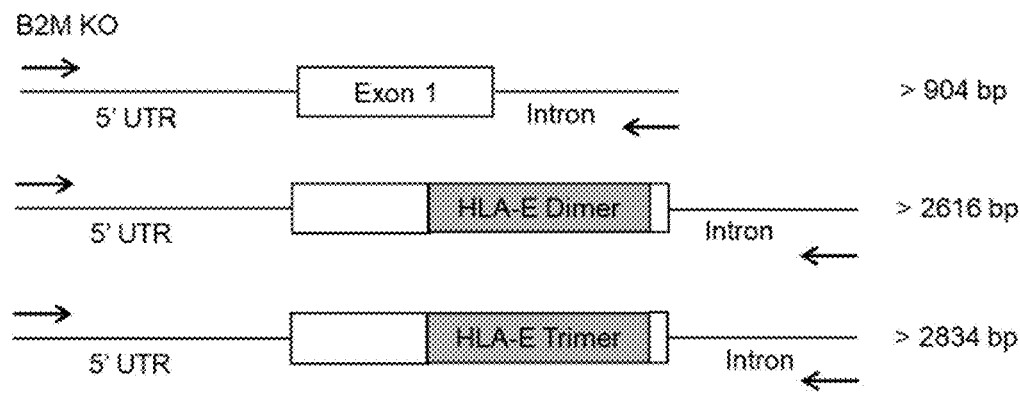
FIGS. 7A-C depicts the Knock-in of HLA-E complete sequence in B2M locus.
Figure 7B:
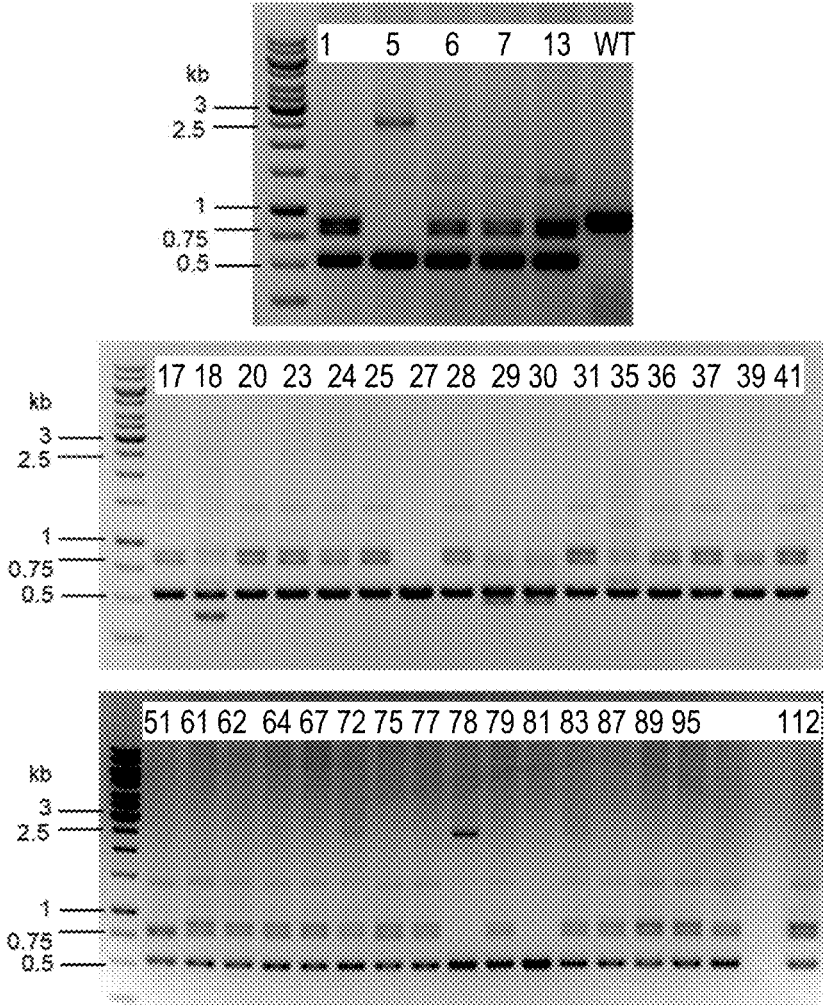
Figure 7:
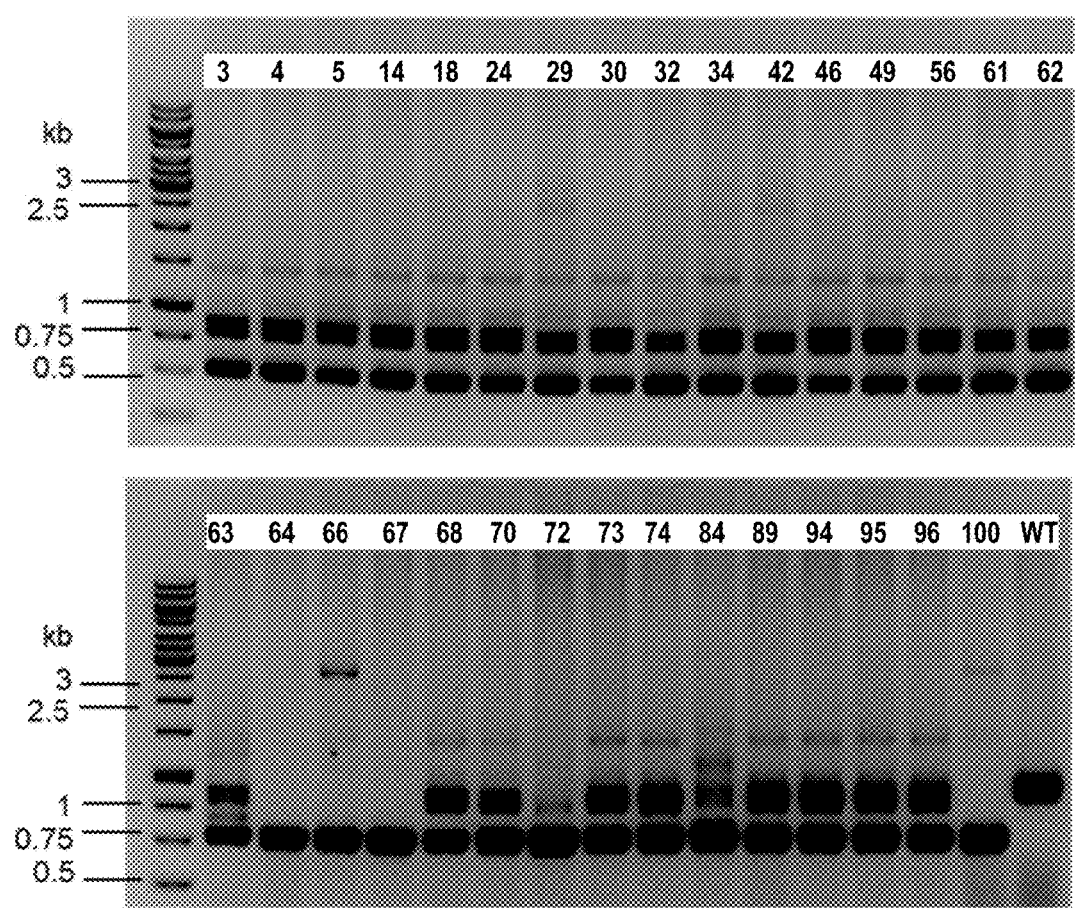

Next, the clones were genotyped that were potentially positive for HLA-E insertion. PCR amplification from 5' to 3' homology arms was supposed to demonstrate the integration of the complete sequence (FIG. 7A). Interestingly, the correct amplification (HLA-E Dimer: 2.6 kb and HLA-E Trimer: 2.8 kb) was detected in a limited number of clones out of which HLA-E Dimer Clone #5 and 78 as well as HLA-E Trimer Clone #66 and 100 represented a clear band with the displacement of the wild-type allele at 0.9 kb (FIGS. 7B and C).

HLA Expression in HLA-E KI hIPSCs

Figure 8:
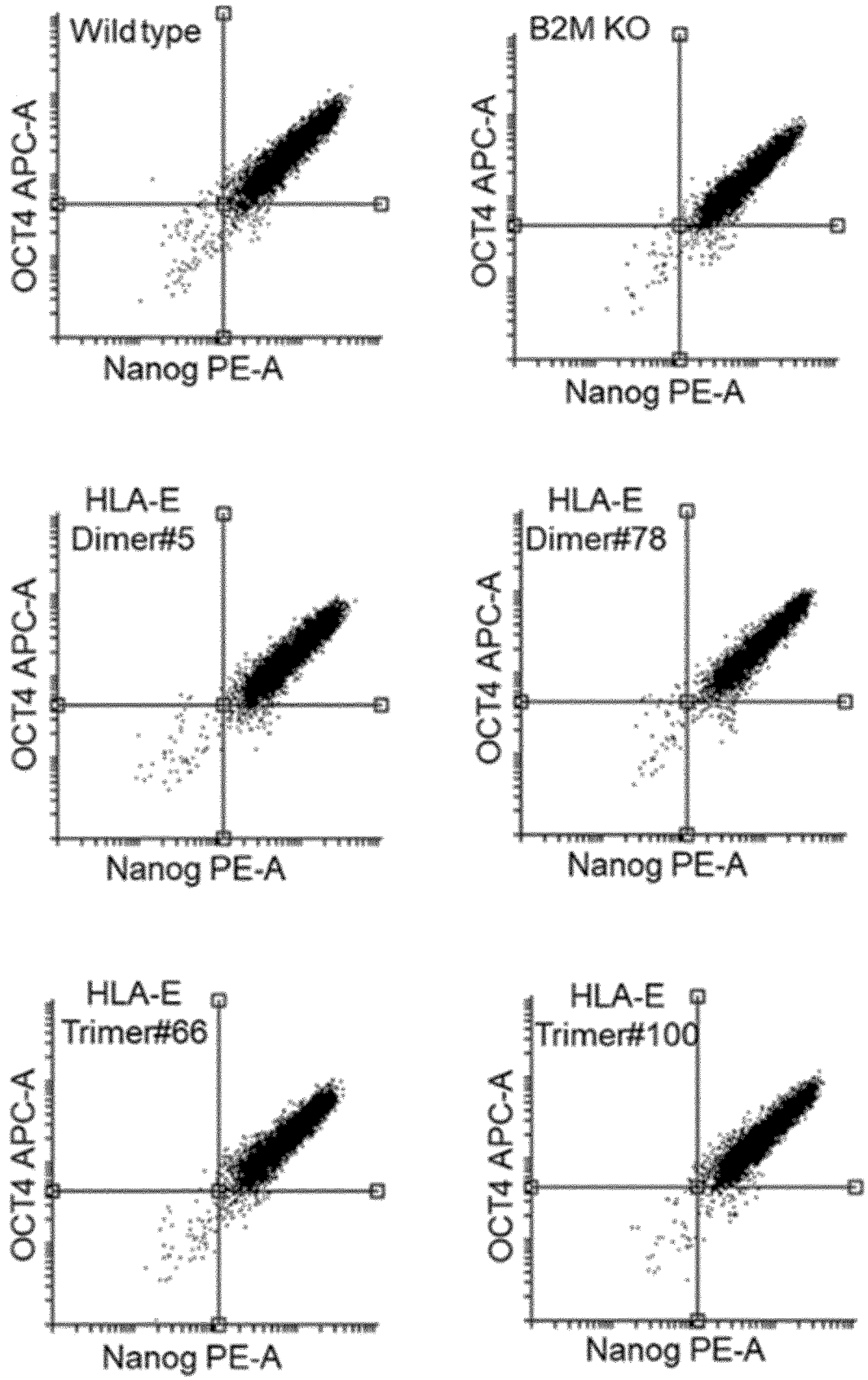
FIG. 8 depicts the pluripotency of HLA-E KI hIPSCs. Flow cytometry analysis of WT, B2M KO, HLA-E Dimer Clone #5 and 78, HLA-E Trimer Clone #66 and 100 for the expression of pluripotency markers; OCT4A and Nanog detected at APC-A and PE-A channels respectively.

Next, HLA-E Dimer Clone #5 and 78 as well as HLA-E Trimer Clone #66 and 100 were cultured and first analyzed them for the expression of pluripotency markers (OCT4A and Nanog). All clones including WT and B2M KO line were found to be more than 90% double positive for the expression of both OCT4A and Nanog as demonstrated by flow cytometry analysis (FIG. 8).

Figure 9:
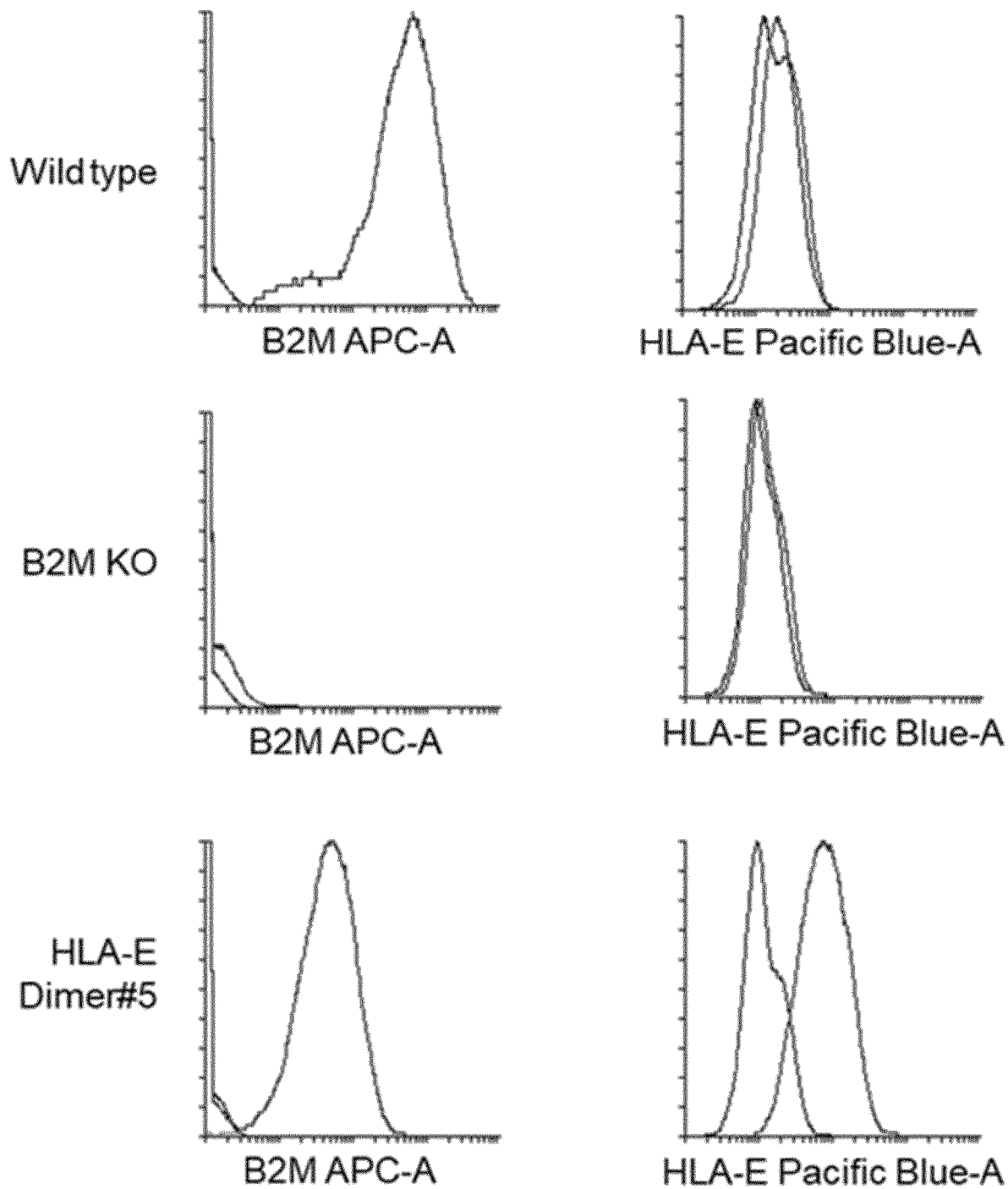
FIG. 9 depicts the HLA expression in HLA-E KI hIPSCs. Flow cytometry analysis of WT, B2M KO, HLA-E Dimer Clone #5 and 78, HLA-E Trimer Clone #66 and 100 for the expression of B2M and HLA-E detected at APC-A and Pacific Blue-A channels respectively. No stain tracings are shown in dark.
Figure 9:
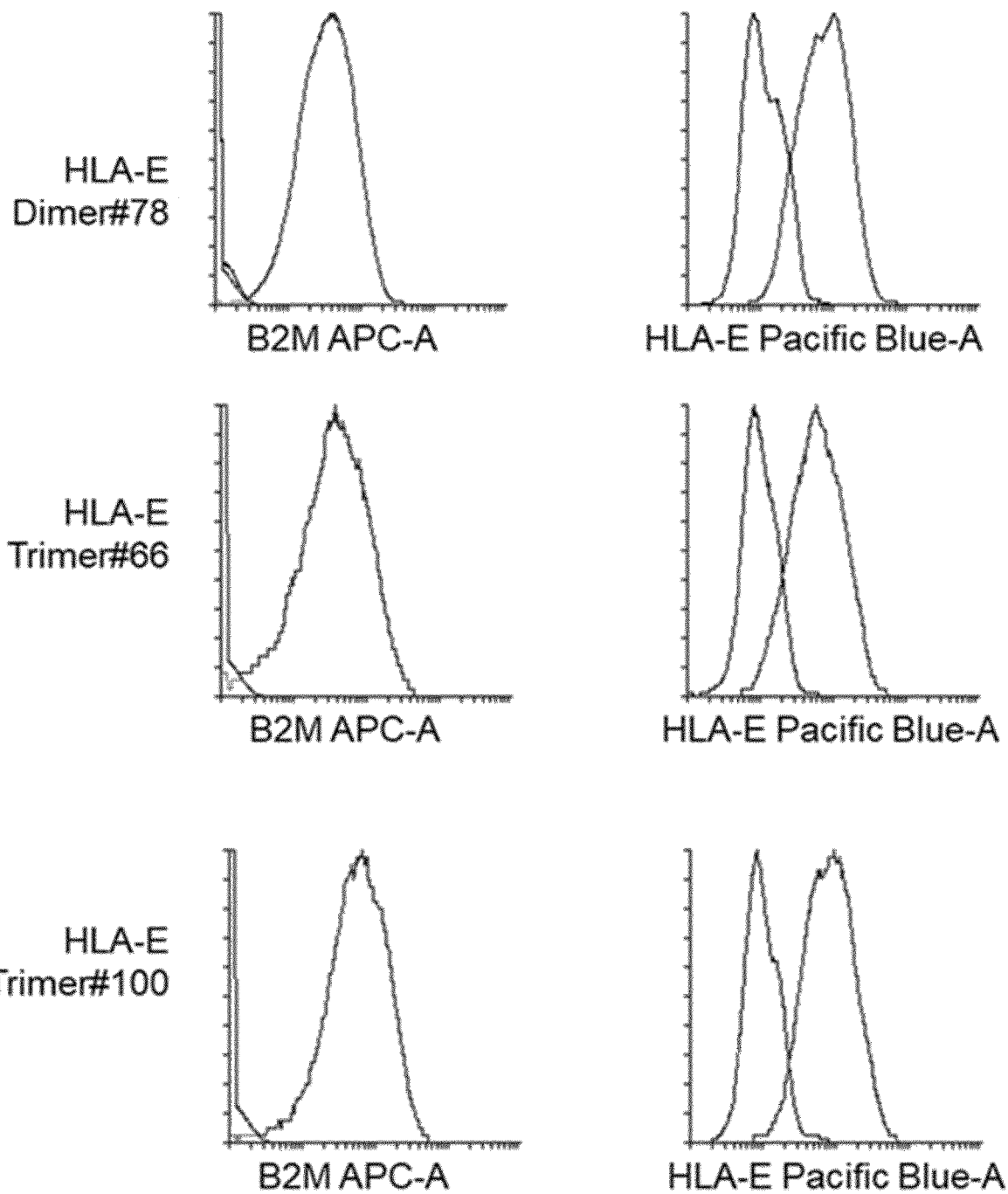

Subsequently, hIPSCs were analyzed for B2M and HLA-E protein expression upon stimulation with interferon (IFN)-γ for 24 hrs. WT cells expressed B2M as a positive control, whereas B2M KO hIPSCs were negative for B2M and HLA-E as expected. In addition, >95% of HLA-E Dimer (#5 and #78) and Trimer clones (#66 and #100) were positive for B2M and HLA-E expression (FIG. 9).

Example 2: Use of Modified PSC to Generate Bioengineered Heart Muscle Tissue

Engineered heart muscle can be generated starting from PSC using the protocol described in WO 2015/040142 and Tiburcy et al. (2017), Circulation, 135:1832-1847 as well as WO 2015/025030. The pluripotent stem cells, particularly clones 18, 20 and 34, of Example 1 may be used in this example. This protocol comprises the steps of inducing mesoderm differentiation, cardiac differentiation and cardiac maturation as described in WO 2015/040142 followed by directed tissue formation in a collagen type I hydrogel as described in WO 2015/025030.

In a first step, the PSC have to be differentiated to cardiomyocytes. This can be done as e.g. described in Tiburcy et al. (2017), Circulation, 135:1832-1847 and originally disclosed in WO 2015/040142. The pluripotent stem cells (PSCs) of Example 1 may be plated at $5 \times 10^4$ to $1 \times 10^5$ cells/cm$^2$ on 1:30 Matrigel in phosphate-buffered saline (PBS)-coated plates and cultured in Knockout DMEM, 20% Knock-out Serum Replacement, 2 mmol/L glutamine, 1% nonessential amino acids, 100 U/mL penicillin, and 100 µg/mL streptomycin (all Life Technologies) mixed 1:1 with irradiated human foreskin fibroblast (HFF)-conditioned medium with 10 ng/mL fibroblast growth factor-2 (FGF2) or TeSR-E8 (STEMCELL Technologies). After 1 day the cells may be rinsed with Roswell Park Memorial Institute (RPMI) medium and then treated with RPMI, 2% B27, 200 µmol/L I-ascorbic acid-2-phosphate sesquimagnesium salt hydrate (Sigma-Aldrich), 9 ng/mL Activin A (R&D Systems), 5 ng/mL BMP4 (R&D Systems), 1 µmol/L CHIR99021 (Stemgent), and 5 ng/mL FGF-2 (Miltenyi Biotec) for 3 days. Following another wash with RPMI medium, cells may be cultured from day 4 to 13 with 5 µmol/L IWP4 (Stemgent) followed by RPMI, 2% B27, 200 µmol/L I-ascorbic acid-2-phosphate sesquimagnesium salt hydrate. Where indicated, cardiomyocytes can be metabolically purified by glucose deprivation from day 13 to 17 in RPMI without glucose and glutamine (Biological Industries), 2.2 mmol/L sodium lactate (Sigma-Aldrich), 100 µmol/L β-mercaptoethanol (Sigma-Aldrich), 100 U/mL penicillin, and 100 µg/mL streptomycin.

Figure 12:
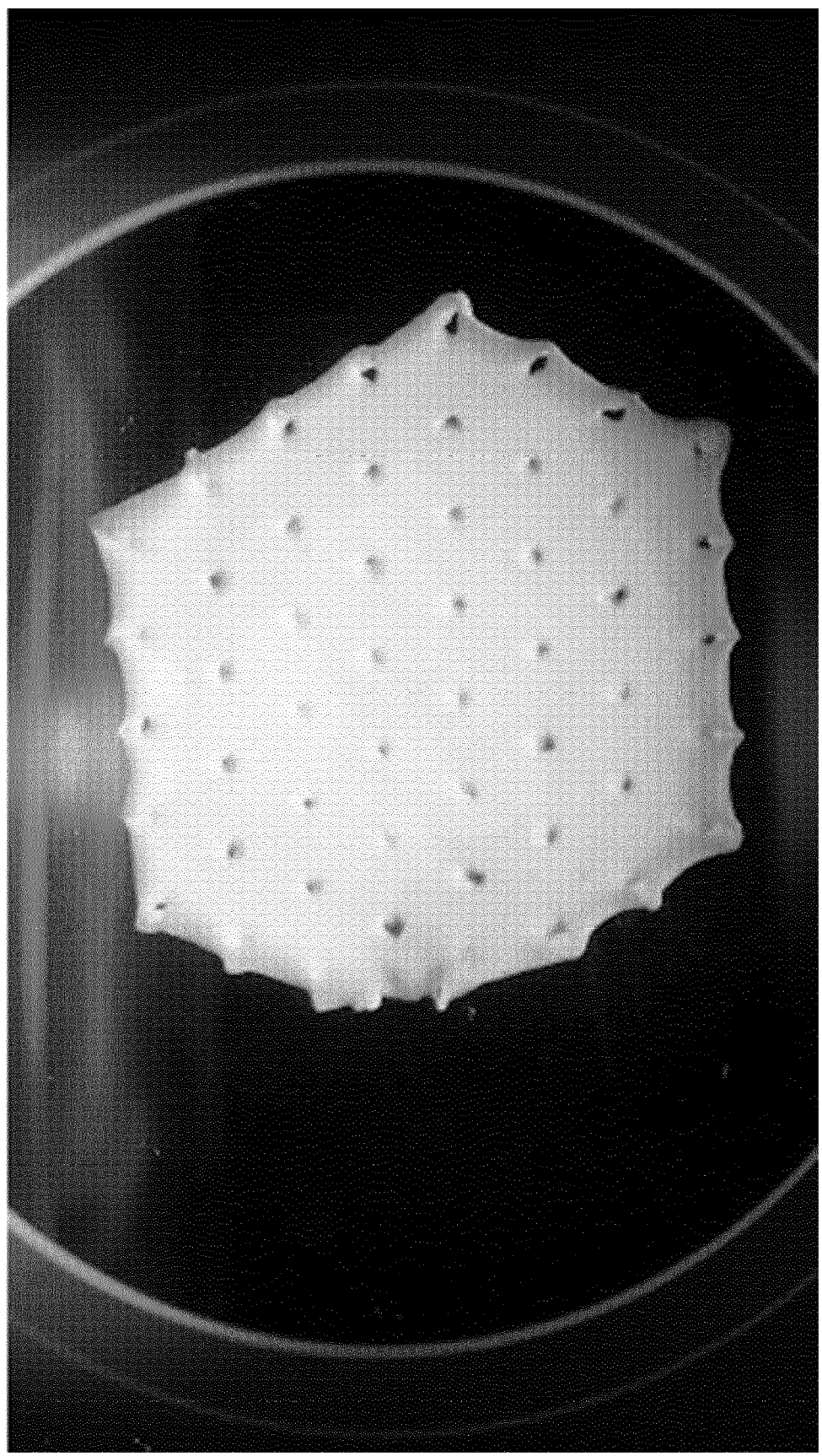
FIG. 12 shows an exemplary engineered tissue that can be produced by the method of the present invention. Here, cardiomyocytes and fibroblasts were formed into heart tissue also known as "EHM patch".

To generate defined, serum-free EHM as described in Tiburcy et al. (2017), Circulation, 135:1832-1847 and originally disclosed in WO 2015/025030, cells can be reconstituted in a mixture of pH-neutralized medical grade bovine collagen (LLC Collagen Solutions, 0.4 mg/EHM), concentrated serum-free medium (2× RPMI, 8% B27 without insulin, 200 U/ml penicillin, and 200 µg/ml streptomycin) and cultured in Iscove-Medium with 4% B27 without insulin, 1% non-essential amino acids, 2 mmol/l glutamine, 300 µmol/l ascorbic acid, 100 ng/ml IGF1 (AF-100-11), 10 ng/ml FGF-2 (AF-100-18B), 5 ng/ml VEGF165 (AF-100-20), 5 ng/ml TGFβ1 (AF-100-21C; mandatory during culture days 0-3), 100 U/ml penicillin, and 100 µg/ml streptomycin (Serum-free Protocol, Table 2). All growth factors may be purchased from Peprotech as "animal-free recombinant human growth factors" and transferred in circular molds (inner/outer diameter: ⅔ mm; height: 5 mm). Human heart muscle tissue then can condense quickly within the casting molds and may be transferred onto preferably flexible stretch devices to facilitate auxotonic contractions (Zimmermann et al. (2006), Nat Med, 12:452-458; Soong et al. (2012), Curr Protoc Cell Biol 55:23.8.1.-23.8.21; Tiburcy et al. (2014) Methods Mol Biol 1181:167-176; incorporated herein by reference and disclosed in WO 2007/054286) on culture day 3. Medium is changed every other day. Heart muscle tissue culture under stretch is performed for at least 7 days. FIG. 12 shows an exemplary result of this protocol.

TABLE 2

Overview of EHM Protocols

| Component | Starting Protocol | Matrix Protocol | Serum-Free Protocol |
|---|---|---|---|
| EHM reconstitution mixture | | | |
| Collagen rat (research grade), mg/EHM | 0.4 | | |
| Collagen bovine (medical grade), mg/EHM | | 0.4 | 0.4 |
| Matrigel, %, v/v | 10 | | |
| Base medium | DMEM | DMEM | RPMI |
| Horse serum, % | 10 | | |
| Chick embryo extract, % | 2 | | |
| Fetal bovine serum, % | | 20 | |
| B27 (without insulin), % | | | 4 |
| EHM culture medium | | | |
| Base medium | Iscove | Iscove | Iscove* |
| Fetal bovine serum, % | 20 | 20 | |
| B27 (without insulin), % | | | 4 |
| IGF-1, ng/mL | | | 100 |
| FGF-2, ng/mL | | | 10 |
| VEGF165, ng/mL | | | 5 |
| TGF-β1, ng/mL | | | 5 |
| Nonessential amino acids, % | 1% | 1% | 1% |
| Glutamine, mmol/L | 2 | 2 | 2 |
| Penicillin, U/mL | 100 | 100 | 100 |
| Streptomycin, µg/mL | 100 | 100 | 100 |
| β-Mercaptoethanol, µmol/L | 100 | 100 | |

DMEM indicates Dulbecco modified Eagle medium; EHM, engineered human myocardium; FGF-2, fibroblast growth factor-2; IGF-1, insulin-like growth factor 1; RPMI, Roswell Park Memorial Institute medium; TGF-β1, transforming growth factor-β1; and VEGF165, vascular endothelial growth factor 165.
*Alternatively other basal medium with ≥1.2 mmol/L calcium.

Example 3: Use of Modified PSC to Generate Bioengineered Heart Muscle Tissue

Figure 10:
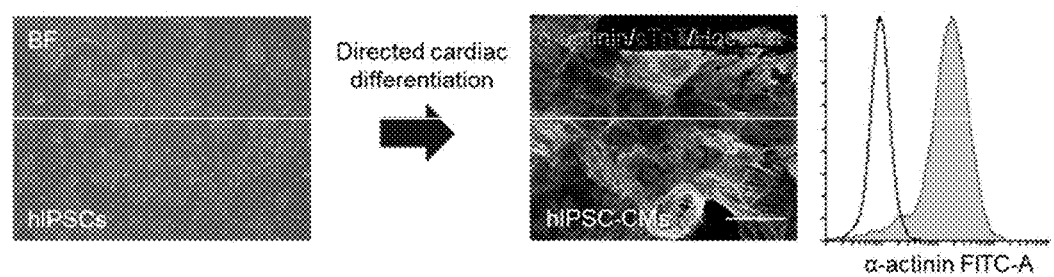
FIGS. 10A-B depict HLA expression in HLA-E KI CMs.
Figure 10:
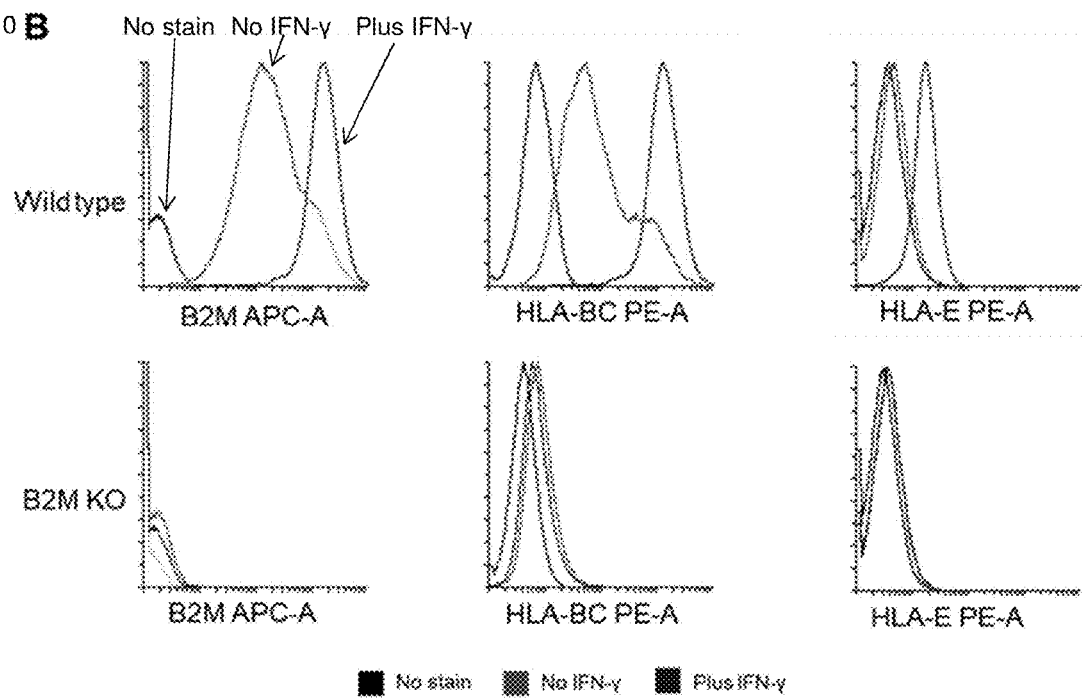

The hIPSCs obtained herein (see Example 1) were differentiated into cardiomyocytes (CMs) based on the protocol described above in Example 2 (Tiburcy et al. 2017 as well as WO 2015/025030). HLA-E KI hIPSC-derived CMs showed expression of sarcomeric proteins; alpha-actinin and cardiac Troponin T (cTnT) with a high purity of >90% actinin+ cells (FIG. 10A).

Figure 10B:
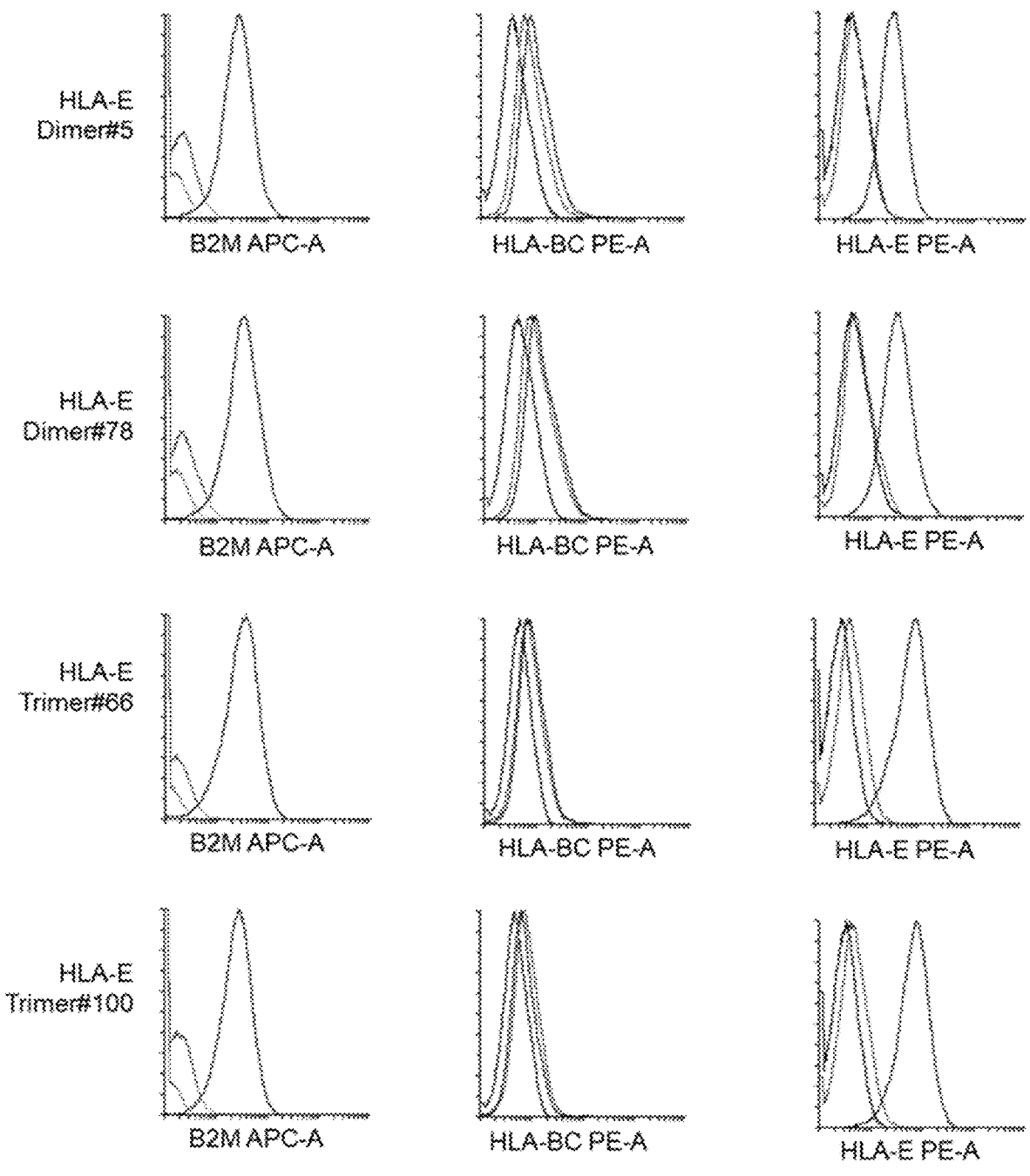

Flow cytometry analysis revealed that WT CMs express B2M and HLA Class I molecules; HLA-B and C, but HLA-E under basal conditions. IFN-γ treatment induced even stronger expression in B2M and HLA-B, C molecules and slightly less HLA-E expression (~60%). As a negative control, B2M KO CMs showed no HLA expression as expected. HLA-E KI Clones (both Dimer and Trimer) expressed B2M and HLA-E only after IFN-γ treatment, and did not show any other HLA Class I expression. CMs differentiated from HLA-E Trimer hIPSC lines presented slightly higher expression of HLA-E as compared to their counterparts in HLA-E Dimer for the initial analysis (HLA-E Dimer CMs: >85% and HLA-E Trimer CMs: >95% HLA-E positive; FIG. 10B).

Thus, in this Example cardiomyocytes (as a cell type that is essential for the function of the engineered heart tissue) have been experimentally provided from pluripotent stem cells that are deficient of endogenous MHC class I molecules presented on the cell surface of the pluripotent stem cell and comprise an immunomodulatory protein on their surface.

Figure 11:
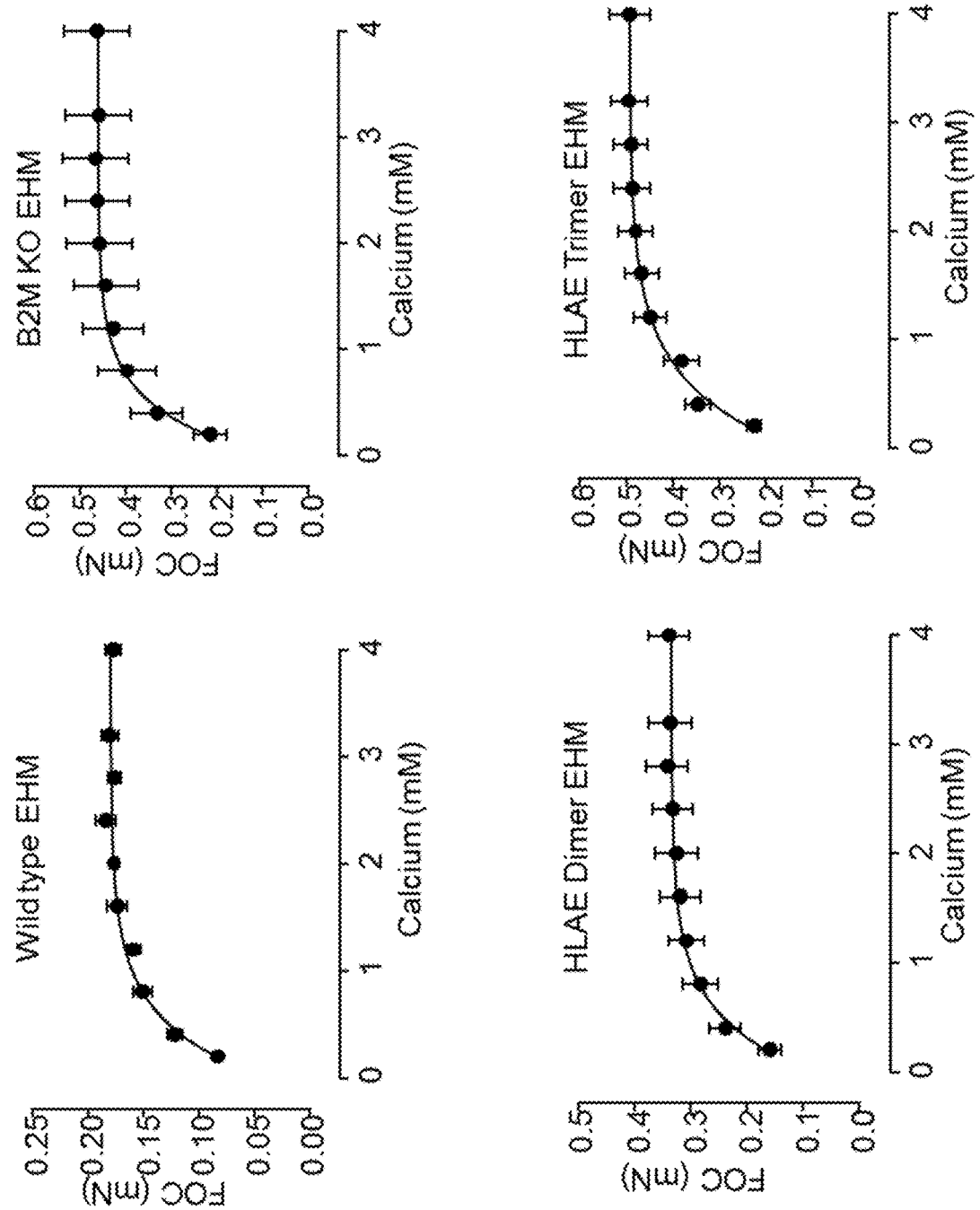
FIGS. 11A-C depict hypo-immunogeneic Engineered Human Myocardium (EHM) of the invention.

This Example further aimed at generating a non-immunogenic engineered heart tissue from the obtained cardiomyocytes as described herein and made use of the protocol of Tiburcy et al. 2017 and WO 2015/025030 described herein (see Example 2). FIG. 11A shows a schematic illustration of the approach taken and FIG. 11B shows images of the EHM during the production process. FIG. 12 is a photograph of an exemplary EHM.

Fibroblasts were used as second cell type that forms part of the engineered tissue. These cells provide connective tissue. In this Example, non-modified fibroblasts, i.e. without modification of the immunogenicity, were used. For use in treatments, the fibroblasts that form part of the engineered tissue, could also be obtained from the pluripotent stem cells that are deficient of endogenous MHC class I molecules presented on the cell surface of the pluripotent stem cell and comprise an immunomodulatory protein on their surface.

After completion of the production of the EHM as described herein, a comparison of the force of contraction (FOC) of wild type EHM, B2M knockout EHM, HLA-E dimer EHM and HLA-E trimer EHM was performed (see FIG. 10C). As apparent from the results, all analyzed EHM show an increase of the contractile force with increased $Ca^{2+}$ concentrations. Interestingly, the EHM derived from PSCs that were genetically modified showed a higher contractile force than the non-modified (WT) EHM.

In sum, the present Example shows that EHM (as an illustrative example of a non-immunogenic engineered tissue of the invention) can be produced from cardiomyocytes that were obtained by the differentiation of the pluripotent stem cells into said at least one cell type, wherein the pluripotent stem cells are deficient of endogenous MHC class I molecules (B2M knockout) presented on the cell surface of the pluripotent stem cell and comprising an immunomodulatory protein (HLA-E dimer/trimer) on their surface.

Example 4: Use of Modified PSC to Generate Engineered Brain Tissue/Neurons

An example for the generation of human brain tissue is disclosed in Lancaster et al. 2013, Nature, 501:373-379. Here, cerebral organoids are generated. The pluripotent stem cells of Example 1 may be used in this Example.

PSC may be maintained on CF-1-gamma-irradiated mouse embryonic stem cells (MEFs) (Global Stem) according to WiCell protocols. On day 0 of organoid culture, PSC at less than passage 50 may be dissociated from MEFs by dispase treatment and MEFs can be removed by gravity separation of stem cell colonies before trypsinization of PSC to generate single cells. In total, 4,500 cells may then be plated in each well of an ultra-low-binding 96-well plate (Corning) in human ES media with low concentration basic fibroblast growth factor (4 ng/ml) and 50 mM Rho-associated protein kinase (ROCK) inhibitor (Calbiochem). Embryoid bodies may be fed every other day for 6 days then transferred to low adhesion 24-well plates (Corning) in neural induction media containing Dulbecco's modified eagle medium (DMEM)/F12, 1:100 N2 supplement (Invitrogen), Glutamax (Invitrogen), minimum essential media-nonessential amino acids (MEM-NEAA) and 1 mg/ml heparin 50 (Sigma). The cell then may begin forming neuroepithelial tissues, which were fed every other day for 5 days. On day 11 of the protocol, tissues may be transferred to droplets of Matrigel (BD Biosciences) by pipetting into cold Matrigel on a sheet of Parafilm with small 3 mm dimples. These droplets may be allowed to gel at 37° C. and were subsequently removed from the Parafilm and grown in differentiation media containing a 1:1 mixture of DMEM/F12 and Neurobasal containing 1:200 N2 supplement (Invitrogen), 1:100 B27 supplement without vitamin A (Invitrogen), 3.5 µl/l 2-mercaptoethanol, 1:4,000 insulin (Sigma), 1:100 Glutamax (Invitrogen) and 1:200 MEM-NEAA. After 4 days of stationary growth, the tissue droplets may be transferred to a spinning bioreactor containing differentiation media as above except B27 supplement with vitamin A (Invitrogen) may be used. Because retinoic acid has been shown to be important for neuronal differentiation in vivo, it may be included in the final media used to differentiate the cerebral organoids.

Example 5: Use of Modified PSC to Generate Engineered Skeletal Muscle Tissue

An exemplary method to induce differentiation of PSC into skeletal muscle tissue is disclosed in Rao et al. (2018), Nature Communications, 9(126):1-12. The pluripotent stem cells of Example 1 may be used in this Example. The differentiation protocol is divided into several steps:
Myogenic Differentiation of hPSCs into iMPCs.

PSC may be maintained in feeder-free conditions in E8 medium (Stemcell Technologies). PSC colonies may be dissociated into single cells with Accutase (Stemcell Technologies) and seeded onto Matrigel (Corning) coated 6-well plates at a cell density of $1\times10^3/cm^2$. PSC may be kept in E8 for expansion, then dissociated into single cells with Accutase and seeded onto matrigel coated 6-well plates in E8 supplemented with Y27632 (5 µM, Tocris) at 3.3×104 cells/$cm^2$. The following day, E8 media may be replaced with E6 media and cells may be cultured for 2 days supplemented with CHIR99021 (10 µM, Selleck Chemical), after which CHIR99021 may be removed and E6 media supplemented with 1 µg/mL Dox (Sigma) for 18 days until induced myogenic progenitor cells (iMPCs) may be sorted by FACS as described below.
Flow Cytometry Analysis Cells may be dissociated with 0.25% Trypsin-EDTA, counted and washed with PBS, then resuspended in flow buffer at a concentration of $2\times10^6$ to $1\times10^7$ cells/ml. To count cells expressing Tra-1-81 or CD56, anti-Tra-1-81 (Stemgent, 09-0011) or anti-CD56 (PE, R&D, FAB2408P) antibodies and isotype matched controls may be applied according to manufacturer's instructions and cells may be analyzed using FACSCanto™ II flow cytometer (BD Biosciences). Cell population of interest may be first gated for cell size and granularity, and then for the expression level of Tra-1-81 or CD56.
Sorting of iMPCs At differentiation day 20, cells may be dissociated with 0.25% Trypsin-EDTA (Thermo) and washed in neutralizing media. Detached cells may be centrifuged at 300 g for 5 min, then may be resuspended in sorting solution and filtered through 30 μM filter (SYSMEX) to remove clusters and debris. Single cell suspensions may be kept on ice until sorting, with undifferentiated hPSCs used as negative control. Cells may be sorted for GFP using MoFlo® Astrios™ cell sorter (Beckman Coulter).

Expansion of iMPCs

After sorting, iMPCs may be kept on ice in collecting solution, spun down at 300 g for 5 min, and resuspended in fresh E6 media supplemented with Y27632, Dox, and bFGF, then may be seeded at $4 \times 10^4/cm^2$ in Matrigel-coated flasks. After 24-48 h of post sorting, cells may be incubated in expansion media (EM), supplemented with Dox and bFGF, and passaged at a 1:3-1:6 ratio every 3-4 days after reaching 80% confluence.

2D Differentiation of iMPCs iMPCs may be seeded at the density of $1 \times 10^5/cm^2$ on Matrigel-coated dishes and after reaching 100% confluence, EM may be washed out with PBS and switched to differentiation media (DM) that may be changed every other day.

Fabrication and Differentiation of iSKM Bundles

Three-dimensional engineered skeletal muscle (iSKM bundles) may be formed within polydimethylsiloxane (PDMS) molds containing two semi-cylindrical wells (7 mm long, 2 mm diameter), cast from 3D-machined Teflon masters. PDMS molds may be coated with 0.2% (w/v) pluronic (Invitrogen) for 1 h at room temperature to prevent hydrogel adhesion. Laser-cut Cerex® frames ($9 \times 9$ mm$^2$, 1 mm wide rim) positioned around the 2 wells serve to anchor bundle ends and facilitate handling and implantation. Cell/hydrogel mixture may be injected into the PDMS wells and polymerized at 37° C. for 30 min. Formed iSKM bundles may be kept on rocking platform in EM supplemented with 1 μg/mL Dox and 1.5 mg/mL 6-aminocaproic acid (ACA, Sigma) for 4 days. Media may then be switched to DM supplemented with 2 mg/mL ACA and 50 μg/mL ascorbic acid (Sigma), with media changed daily.

Example 6: Use of Modified PSC to Generate Engineered Pancreatic Tissue

An exemplary method to create pancreatic tissue, or to be more specific, insulin-secreting beta cells, is disclosed in Pagliuca et al. (2014), Cell, 159:428-439. Here, pluripotent stem cells are differentiated to insulin-producing pancreatic beta cells (SC-β):

For initiation of SC-β cell differentiation, pluripotent stem cells may be seeded at $6 \times 10^5$ cells/ml in mTeSR1 media +10 mM Y27632. The differentiation may be started by changing media to Day media. Media changes were as follows. Day 1: S1+100 ng/ml ActivinA (R&D Systems)+3 mMChir99021 (Stemgent). Day 2: S1+100 ng/ml ActivinA. Days 4, 6: S2+50 ng/ml KGF (Peprotech). Days 7, 8: S3+50 ng/ml KGF+0.25 mM Sant1 (Sigma)+2 mM RA (Sigma)+ 200 nM LDN193189 (only Day 7) (Sigma)+500 nM PdBU (EMD Millipore). Days 9, 11, 13: S3+50 ng/ml KGF+0.25 mM Sant1+100 nM RA. Days 14, 16: S5+0.25 mM Sant1+ 100 nM RA+1 mM XXI (EMD Millipore)+10 mM Alk5i II (Axxora)+1 mM T3 (EMD Millipore)+20 ng/ml Betacellulin (Thermo Fisher Scientific). Days 18, 20: S5+25 nM RA+1 mM XXI+10 mM Alk5i II+1 mM T3+20 ng/ml Betacellulin. Days 21-35 (change every second day): S6+10 mM Alk5i II+1 mM T3. Thereby inducing the differentiation of pluripotent stem cells into SC-β cells The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of producing a non-immunogenic engineered heart muscle tissue from pluripotent stem cells, comprising:
   modifying ND50039 pluripotent stem cells to provide modified ND50039 pluripotent stem cells comprising (i) a deletion of the β2-Microglobulin (B2M) gene endogenous to wild-type ND50039 cells, thereby preventing cell-surface expression of endogenous HLA-A, B, and C by the modified ND50039 cells, and (ii) introduction of an expression construct configured to drive cell-surface expression of an exogenous immunomodulatory fusion protein comprising at least a portion of B2M covalently linked to at least a portion of an HLA class Iα chain by the modified ND50039 cells;
   differentiating the modified ND50039 pluripotent stem cells into at least one first cell type that is essential for the function of the engineered heart muscle tissue, wherein the first cell type is a cardiomyocyte;
   differentiating the modified ND50039 pluripotent stem cells into at least one second cell type that forms a supporting component for the first cell type within the engineered heart muscle tissue as a separate cell population from the first cell type, wherein the second cell type is a fibroblast; and
   mixing the first cell type and the second cell type at a defined ratio in the presence of a biocompatible extracellular matrix to form the engineered heart muscle tissue,
   wherein the engineered heart muscle tissue is non-immunogenic to a recipient of the engineered heart muscle tissue.

2. The method of claim 1, wherein the engineered heart muscle tissue
   (a) is not recognized as allogenic by effector T cells, and/or
   (b) is resistant to NK-mediated lysis.

3. The method of claim 1, wherein the HLA class Iα chain is selected from the group consisting of HLA-A, HLA-B, HLA-C, HLA-E, HLA-F and HLA-G.

4. The method of claim 1, wherein the exogenous immunomodulatory fusion protein comprises at least a portion of B2M and at least a portion of HLA-A.

5. The method of claim 4, wherein the HLA-A is HLA-A0201.

6. The method of claim 1, wherein the modified ND50039 pluripotent stem cells further express a target peptide antigen that is presented by the immunomodulatory fusion protein on the cell surface.

7. The method of claim 6, wherein the target peptide antigen is covalently linked to the at least a portion of an HLA class Iα chain comprised within the immunomodulatory fusion protein.

8. The method of claim 7, wherein the target peptide antigen comprises the sequence VMAPRTLFL (SEQ ID NO: 1).

9. The method of claim 1, wherein the defined ratio comprises 80% of the first cell type.

10. An engineered heart muscle tissue comprising,
    a mixture comprising a first cell type, at least one second cell type, and a biocompatible extracellular matrix, wherein
    the first cell type is essential for the function of the engineered heart muscle tissue, wherein the first cell type is a cardiomyocyte, and wherein said first cell type is differentiated from a first population of modified ND50039 pluripotent stem cells comprising (i) a deletion of the β2-Microglobulin (B2M) gene endogenous to wild-type ND50039 cells, thereby preventing cell-surface expression of endogenous HLA-A, B, and C by the modified ND50039 cells, and (ii) introduction of an expression construct configured to drive cell-surface expression of an exogenous immunomodulatory fusion protein comprising at least a portion of B2M covalently linked to at least a portion of an HLA class Iα chain by the modified ND50039 cells,
    the at least one second cell type forms a supporting component for the first cell type within the engineered heart muscle tissue, wherein the second cell type is a fibroblast and wherein said at least one second cell type is differentiated from a second population of modified ND50039 pluripotent stem cells comprising (i) a deletion of the β2-Microglobulin (B2M) gene endogenous to wild-type ND50039 cells, thereby preventing cell-surface expression of endogenous HLA-A, B, and C by the modified ND50039 cells, and (ii) introduction of an expression construct configured to drive cell-surface expression of an exogenous immunomodulatory fusion protein comprising at least a portion of B2M covalently linked to at least a portion of an HLA class Iα chain by the modified ND50039 cells into said at least one second cell type, and
    the first cell type and the second cell type are mixed at a defined ratio,
    thereby rendering the engineered heart muscle tissue to be non-immunogenic to a recipient of the engineered heart muscle tissue.

11. The engineered heart muscle tissue of claim 10, wherein the defined ratio comprises 80% of the first cell type.

12. A method of treating a heart disease condition, comprising administering to a subject in need thereof an effective amount of the engineered heart muscle tissue of claim 10.

13. The method of claim 12, wherein the heart disease condition is selected from the group consisting of myocardial infarction and heart failure.

* * * * *